(12) United States Patent
Sällberg et al.

(10) Patent No.: US 7,244,715 B2
(45) Date of Patent: **\*Jul. 17, 2007**

(54) VACCINES CONTAINING RIBAVIRIN AND METHODS OF USE THEREOF

(75) Inventors: Matti Sällberg, Alvsjo (SE); Catharina Hultgren, Stockholm (SE)

(73) Assignee: Tripep AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/411,493

(22) Filed: Apr. 26, 2006

(65) Prior Publication Data

US 2006/0183699 A1    Aug. 17, 2006

Related U.S. Application Data

(63) Continuation of application No. 10/817,591, filed on Apr. 2, 2004, which is a continuation of application No. 09/929,955, filed on Aug. 15, 2001, now Pat. No. 6,858,590, said application No. 10/817,591 is a continuation-in-part of application No. 10/719,619, filed on Nov. 20, 2003, which is a continuation of application No. 10/104,966, filed on Mar. 22, 2002, now Pat. No. 6,680,059, which is a continuation of application No. 09/705,547, filed on Nov. 3, 2000, now abandoned.

(60) Provisional application No. 60/225,767, filed on Aug. 17, 2000, provisional application No. 60/229,175, filed on Aug. 29, 2000.

(51) Int. Cl.
*A61K 31/7188* (2006.01)
*A61K 48/00* (2006.01)
*A61K 39/00* (2006.01)

(52) U.S. Cl. ............... 514/44; 424/93.1; 424/228.1; 424/227.1; 424/226.1; 424/225.1

(58) Field of Classification Search ............ 424/93.1, 424/189.1, 225.1, 226.1, 227.1, 228.1; 514/44
See application file for complete search history.

(56) References Cited

U.S. PATENT DOCUMENTS

| | | | |
|---|---|---|---|
| 4,946,778 A | 8/1990 | Ladner et al. | |
| 4,950,647 A | 8/1990 | Robins et al. | |
| 5,350,671 A | 9/1994 | Houghton et al. | |
| 5,371,017 A | 12/1994 | Houghton et al. | |
| 5,372,928 A | 12/1994 | Miyamura et al. | |
| 5,585,258 A | 12/1996 | Houghton et al. | |
| 5,589,466 A | 12/1996 | Felgner et al. | |
| 5,597,691 A | 1/1997 | Houghton et al. | |
| 5,670,152 A | 9/1997 | Weiner et al. | |
| 5,670,153 A | 9/1997 | Weiner et al. | |
| 5,679,342 A | 10/1997 | Houghton et al. | |
| 5,683,864 A | 11/1997 | Houghton et al. | |
| 5,698,390 A | 12/1997 | Houghton et al. | |
| 5,712,087 A | 1/1998 | Houghton et al. | |
| 5,712,088 A | 1/1998 | Houghton et al. | |
| 5,712,145 A | 1/1998 | Houghton et al. | |
| 5,714,596 A | 2/1998 | Houghton et al. | |
| 5,728,520 A | 3/1998 | Weiner et al. | |
| 5,756,312 A | 5/1998 | Weiner et al. | |
| 5,767,097 A | 6/1998 | Tam | |
| 5,856,437 A | 1/1999 | Miyamura et al. | |
| 5,863,719 A | 1/1999 | Houghton et al. | |
| 5,871,903 A | 2/1999 | Miyamura et al. | |
| 5,885,799 A | 3/1999 | Houghton et al. | |
| 5,932,556 A | 8/1999 | Tam | |
| 5,942,234 A | 8/1999 | Ralston et al. | |
| 5,959,092 A | 9/1999 | Miyamura et al. | |
| 5,968,775 A | 10/1999 | Houghton et al. | |
| 5,989,905 A | 11/1999 | Houghton et al. | |
| 6,027,729 A | 2/2000 | Houghton et al. | |
| 6,056,961 A | 5/2000 | Lavie et al. | |
| 6,060,068 A | 5/2000 | Doyle et al. | |
| 6,063,380 A | 5/2000 | Chedid et al. | |
| 6,063,772 A | 5/2000 | Tam | |
| 6,071,693 A | 6/2000 | Cha et al. | |
| 6,074,816 A | 6/2000 | Houghton et al. | |
| 6,074,846 A | 6/2000 | Ralston et al. | |
| 6,074,852 A | 6/2000 | Ralston et al. | |
| 6,096,541 A | 8/2000 | Houghton et al. | |
| 6,130,326 A | 10/2000 | Ramasamy et al. | |
| 6,150,087 A | 11/2000 | Chien | |
| 6,150,337 A | 11/2000 | Tam | |
| 6,171,782 B1 | 1/2001 | Houghton et al. | |
| 6,190,864 B1 | 2/2001 | Cha et al. | |
| 6,194,140 B1 | 2/2001 | Houghton et al. | |
| 6,214,583 B1 | 4/2001 | Cha et al. | |
| 6,235,888 B1 | 5/2001 | Pachuk et al. | |
| 6,274,148 B1 | 8/2001 | Ralston et al. | |
| 6,297,370 B1 | 10/2001 | Cha et al. | |
| 6,303,292 B1 | 10/2001 | Weiner et al. | |
| 6,312,889 B1 | 11/2001 | Houghton et al. | |

(Continued)

FOREIGN PATENT DOCUMENTS

EP    0 388 232    9/1990

(Continued)

OTHER PUBLICATIONS

Encke et al. J. Immunol. 1998, vol. 161, pp. 4917-4923.*

(Continued)

*Primary Examiner*—Bruce R. Campell
*Assistant Examiner*—Bao Qun Li
(74) *Attorney, Agent, or Firm*—Knobbe Martens Olson & Bear LLP

(57) ABSTRACT

Compositions and methods for enhancing the effect of vaccines in animals, such as domestic, sport, or pet species, and humans are disclosed. More particularly, vaccine compositions comprising ribavirin and an antigen, preferably an antigen that has an epitope present in Hepatitis C virus (HCV), are disclosed for use in treating and preventing disease, preferably HCV infection.

18 Claims, 5 Drawing Sheets

U.S. PATENT DOCUMENTS

| | | |
|---|---|---|
| 6,514,731 B1 | 2/2003 | Valenzuela et al. |
| 6,541,011 B2 | 4/2003 | Punnonen et al. |
| 6,555,114 B1 | 4/2003 | Maertens et al. |
| 6,680,059 B2 | 1/2004 | Sallberg et al. |
| 6,762,024 B2 | 7/2004 | Maertens et al. |
| 6,858,590 B2 | 2/2005 | Sallberg et al. |
| 6,960,569 B2 | 11/2005 | Sallberg |
| 6,974,864 B2 | 12/2005 | Maertens et al. |
| 7,056,658 B2 | 6/2006 | Valenzuela et al. |
| 7,105,303 B2 | 9/2006 | Ralston et al. |
| 7,122,306 B2 | 10/2006 | Maertens et al. |
| 2002/0165172 A1 | 11/2002 | Sallberg et al. |
| 2002/0187945 A1 | 12/2002 | Tam |
| 2003/0007977 A1 | 1/2003 | Wheeler et al. |
| 2003/0008274 A1 | 1/2003 | Maeterns et al. |

FOREIGN PATENT DOCUMENTS

| | | |
|---|---|---|
| EP | 0 414 475 | 2/1991 |
| EP | 0 450 931 | 6/1996 |
| EP | 0 543 924 | 6/1997 |
| EP | 0 842 947 | 5/1998 |
| EP | 0 693 687 | 7/1999 |
| EP | 0 556 292 | 12/1999 |
| EP | 1 034 785 | 9/2000 |
| EP | 0 318 216 | 8/2001 |
| EP | 0 398 748 | 1/2002 |
| WO | WO 90/15070 | 12/1990 |
| WO | WO 91/15575 | 10/1991 |
| WO | WO 92/10092 | 6/1992 |
| WO | WO 92/19743 | 11/1992 |
| WO | WO 93/00365 | 1/1993 |
| WO | WO 93/06126 | 4/1993 |
| WO | WO 94/11530 | 5/1994 |
| WO | WO 94/12305 | 6/1994 |
| WO | WO 94/16737 | 8/1994 |
| WO | WO 95/11995 | 5/1995 |
| WO | WO 96/09805 | 4/1996 |
| WO | WO 96/28162 | 9/1996 |
| WO | WO 96/33739 | 10/1996 |
| WO | WO 97/12043 | 4/1997 |
| WO | WO 97/26883 | 7/1997 |
| WO | WO 97/29212 | 8/1997 |
| WO | WO 97/31256 | 8/1997 |
| WO | WO 97/47358 | 12/1997 |
| WO | WO 98/16184 | 4/1998 |
| WO | WO 98/16186 | 4/1998 |
| WO | WO 98/30223 | 7/1998 |
| WO | WO 98/34640 | 8/1998 |
| WO | WO 98/37180 | 8/1998 |
| WO | WO 99/04008 | 1/1999 |
| WO | WO 99/28482 | 6/1999 |
| WO | WO 00/44388 | 8/2000 |
| WO | WO 02/13855 | 2/2001 |
| WO | WO 01/38360 | 5/2001 |
| WO | WO 01/96875 | 12/2001 |
| WO | WO 02/14362 | 2/2002 |
| WO | WO 03/031588 | 4/2003 |

OTHER PUBLICATIONS

Chiang et al. Vaccine Strategies Against Microbiol Pathogogen, Apr. 20, 2000, Abstract No. 42.14.*
AASLD Abstracts 940, "Hepatitis C Virus NS5A Sequence Configuration does not Predict Response to Induction Interferon Plus Ribavinn," Hepatology, p. 394A (2000).
Abrignani et al., "Perspectives for a vaccine against hepatitis C virus," Journal of Hepatology, 31: (suppl. 1 ):259-263 (1999).
Andre et al., "Increased Immune Response Elicited by DNA Vaccination with a Synthetic gp120 Sequence with Optimized Codon Usage," Journal of Virology, 72(2):1497-1503 (1998).
Bartenschlager et al., "Substrate Determinants for Cleavage in cis and in trans by the Hapatitis C Virus NS3 Proteinase," Journal of Virology, pp. 198-205 (1995).
Bitter et al., Methods in Enzymol., 153:516-544 (1987).
BLASTN 2.2.9., May 1, 2004.
Chang et al., Aliment Pharmacol Ther. Sep. 2002; 16(9): 1623-1632.
Chen et al., "Detection of Hepatitis C Virus RNA in the Cell Fraction of Saliva Before and After Oral Surgery," J. Med. Virol., 43:223-226 (1995).
Chen et al., "Human and Murine Antibody Recognition is Focused on the ATPase/Helicase, but not the Protease Domain of the Hepatitis C Virus Nonstructural 3 Protein," Hepatalogy, 28(1):219-224 (1998).
Colberre-Garapin, et al., "A new dominant hybrid selective marker for higher eukaryotic cells," J. Mol. Biol. 150:1 (1981).
Cote et al., "Generation of human monoclonal antibodies reactive with cellular antigens" Proc Natl. Acad. Sci., 80:2026-2030 (1983).
Cotonat et al., "Pilot Study of Combination Therapy with Ribavirin and Interferon Alfa for the Retreatment of Chronic Hepatitis B e Antibody-Positive Patients", Hepatology, 31(2):502-506 (2000).
Cramp et al., "Hepatitis C Virus-Specific T-Cell Reactivity During Intereron and Ribavirin Treatment in Chronic Hepatitis C," Gastron. Enterol.,118:346-355 (2000).
Database Genbank [Online] Dec. 2, 1994, retrieved from NCBI Database accession No. IO6434, XP002278035.
Database Registry [Online] No. 511600-20-7, XP02278058 abstract & WO 03/031588A, Apr. 17, 2003, Seq ID No. 1, 10 and 11 Claims.
Davis et al., Human Gene Therapy, 4(6):733 (1993).
Diepolder et al., "Possible mechanism involving T-lymphocyte response to non-structural protein 3 in viral clearance in acute hepatitis C virus infection," Lancet, 346(8981):1006-1007, 1995.
Encke et al. Intervirology 1999, vol. 42, pp. 117-124.
Engvall, E., Meth. Enzymol, 70:419 (1980).
Fang et al., "Ribavirin enhancement of hepatitis C virus core antigen-specific type 1 T helper cell response correlates with the Increased IL-12 level," Journal of Hepatology, 33(5):791-798 (2000).
Fodor et al., Science, 251:767-773 (1991).
Forns et al. PNAS 2000, vol. 97, pp. 13318-13323.
Forns et al., "Hepatitis C virus lacking the hypervariable region 1 of the second envelope protein is infectious and causes acute resalving or persistent infection in chimpanzees," PNAS, vol. 97, No. 24, pp. 13318-113323, (2000).
Gordon et al., "Immune responses to hepatitis C virus structural and nonstructural proteins induced byplasmid DNA immunizations," Journal of Infectious Diseases, 181(1 ):42-50, 2000.
Grakoui et al., "A second hepatitis C virus-encoded proteinase," Proc. Natl. Acad. Sci USA, 90:10583-10587 (1993).
Hahm et al., "NS3-4A of Hepatitis C Virus is a Chymotrypsin-Like Protease," Journal of Virology, The American Society for Microbiology, 69(4): 2534-2539 (1995).
Heagy et al., J. Clin. Invest. 1991, vol. 87, pp. 1916-1924.
Hosoya et al., J. INF. Dis., 168:641-646 (1993).
Houghten et al., Proc. Natl. Acad. Sci. USA, 82:51:32 (1985).
Hsu et al., "Prospects for a Hepatitis C Virus Vaccine", Clin Liver Dis, 3(4):901-915 (1999).
Http://www.msi.com/life/products/cerius2/modules/analogbuilder.html, C2 Analog Builder, Jul. 6, 2000.
Huffman et al., "In vitro effect of 1-beta-D-ribofuranosyl-1,2,4-triazole-3-carboxamide (virazole, ICN 1229) on deoxyribonucleic acid and ribonucleic acid viruses," Antimicrob. Agents. Chemother., 3(2):235 (1973).
Hultgren et al. J. Gene. Virol. 1998, vol. 79, pp. 2381-2391.
Hultgren et al., Clin. Diagn. Lab. Immunol. 4:630-632 (1997).
Huse W.D. et al. Science 256:1275-1281 (1989).
Hutchison et al., Proc. Natl. Acad. Sci. USA 253:6551 (1978).
Janknecht, et al., Proc. Natl. Acad. Sci. USA 88:8972-8976 (1991).
Jin et al., "Expression, isolation, and characterization of the hepatitis C virus ATPase/RNA Helicase," Arch. Biochem. Bioplys., 323:47-53 (1995).
Kakumu et al., "Pilot Study of Ribarvirin and Interferon- for Chronic Hepatitis B," Hepatology, 18(2):258-263 (1993).
Kato, "Genome of human hepatitis C virus (HCV): gene organization, sequence diversity, and variation," Microb. Com. Genomics, 5(3):129-151 (2000).
Kozbor et al., Immunol Today 4:72 (1983).

Kumar et al, "Sequence, expression and reconstitution of an HCV genome from a British isolate derived from a single blood donation," Journal of Viral Hepatitis, 7:459-465 (2000).

Kumar et al., "Hepatitis C virus genomic RNA for polyprotein gene," Journal of Hepatology, 7:459-465 (2000).

Kwong et al., "Structure and function of hepatitis C virus NS3 helicase," Curr. Top. Microbiol. Immunol., 242:171-196 (2000).

Kwong et at., "Hepatitis C virus NS3/4A protease," Antiviral Res., 41(1):67-84 (1999).

Lawrence et al., "Advances in the treatment of hepatitis C," Adv. Intern. Med., 45:65-1 05 (2000).

Lazdina et al., "Humoral and CD4* T helper (th) cell responses to the hepatitis C virus non-structural 3 (NS3) protein: NS3 primes TH 1-like responses more effectively as a DNA-Based immunogen than as a recombinant protein," Journal of General Virology, 82:1299-1308 (2001).

Li et al., "Role of the guanosine triphosphatase Rac2 in T helper cell differentiation," Science, 288:2219-2222 (2000).

Lo, *Mol. Cell. Biol.* 3:1803-1814 (1983).

Logan & Shenk, *Proc. Natl. Acad. Sci.* USA 81:3655-3659, 1984.

Lohmann et al., "Replication of Subgenomic Hepatitis C Virus RNAs in a Hepatoma Cell Line," Science, 285:110-113, (1999).

Lowy, et al., *Cell* 22:817 (1980).

Marquardt et al., "Ribavirin inhibits mast cell mediator release," J. Pharmacol. Exp. Therapeutics, 240(1):145-149 (1987).

Marshall et al., "Detection of HCV RNA by the asymmetric gap ligase chain reaction," PCR Methods and Applications, 4(2):80-84 (1994).

Memar O. et al., "Antiviral Agents in Dermatology; Current Status and Future Prospects," Internation Journal of Dermatology, 34(9):597-606 (1995).

Missale et al., "Different clinical behaviors of acute hepatitis C virus infection are associated with different vigor of the anti-viral cell-mediated immune response," J. Clin. Invest., 98(3):706-714 (1996).

Morrison et al. *Proc. Natl. Acad. Sci.* USA 81:6851-6855 (1984).

Mulligan & Berg, *Proc. Natl. Acad. Sci. USA* 78:2072 (1981).

NCBI, Genbank, M32084. Hepatitis C Virus . . . [Gi:32987] Aug. 2, 1993.

Neuberger et al., "Recombinant antibodies possessing novel effector functions," Nature, 312:604-608 (1984).

O'Hare, et al., *Proc. Natl. Acad. Sci. USA* 78:1527 (1981).

Orlandi et al., Proc. Natl. Acad. Sci. 86: 3833-3837 (1989).

Pape et al., "Role of the specific T-cell response for clearance and control of hepatitis C virus," J. Viral. Hepat., Supp. 6, 1:36-40 (1999).

Peavy at al., "Inhibition of murine plaque-forming cell responses in vivo by ribavirin," J. Immunology, 126(3):861-864 (1981).

Powers et al., "Selective Inhibition of functional lymphocyte subpoputations by ribavirin," Antimicrob. Agents. Chemother., 22(1):108-114 (1982).

Proust B. et al., "Two Successive Hepatitis C Virus Infections in an Intravenous Drug User," Journal of Clinical Microbiology, 38(8):3125-3127 (2000).

Ramasamy et al., "Monocyclic L-Nucleosides with Type 1 Cytokine-Inducing Activity," Journal of Medicinal Chemistry, 43(5):1019-1028 (2000).

Rudikoff et al., Immunology 1982, vol. 79, pp. 1979-1983.

Ruther et al., *EMBO J.*, 2:1791 (1983).

Santerre et al., *Gene.* 30:147 (1984).

Schulof R. S., "Clinical, Virologic, and Immunologic Effects of Combination Therapy with Ribavirin and Isoprinosine in HIV-Infected Homosexual Men," Journal of Acquired Immune Deficiency Syndromes. 3(5):485-492 (1990).

Sidwell at al., "Broad-spectrum antiviral activity of Virazole: 1-beta-D-ribofuranosyl-1,2,4-triazole-3-carboxamide," Science, 177(50):705-706 (1972).

Smith at al., "Molecular Engineering of the Autographa californica Nuclear Polyhedrosis Virus Genome: Deletion Mutations Within the Polyhedrin Gene," Journal of Virology, 46:584 (1983).

Spector et al., "The Antviral Effect of Zidovudine and Ribavirin in Clinical Trials and the Use of p24 Antigen Levels as a Virologic Marker," Journal of Infectious Diseases, 159(5):822-828 (1989).

Steigerwald-Mullen et al., J. Virol. 2000, vol. 74, No. 15, pp. 6748-6759.

Szybalska and Szybalska, "Genetics of Human Cell Lines, IV. DNA-Mediated Heritable Transformationof a Biochemical Trait," Proc Natl Acad Sci USA, 48:2026 (1962).

Takeda et al., "Construction of chimaeric processed immunoglobulin genes containing mouse variable and human constant region sequences," Nature, 314:452-454 (1985).

Tam et al., "Ribavirin Polarizes Human T Cell Responses Towards a Type 1 Cytokine Profile," Journal of Hepatology, 30(3):376-382 (1999) (Abstract).

Tam et al., "The Immunomodulatory effects of ribavirin: Recent findings," International Antiviral News, 7/6:99-100 (1999).

Tan et al., "How hepatitis C virus counteracts the interferon response: the jury is still out on NS5A," Virology, 284(1):1-12 (2001).

Thompson et al., *Cell* 56:313-321 (1989).

Townsend et al., *J. Virol.* 71:3365 (1997).

Vaitukaitis et al., "A method for producing specific antisera with small doses of immunogen," J. Clin. Endocrinology Metab., 33(6):988-991 (1971).

Van der Putten et al., *Proc. Natl. Acad. Sci., USA* 82:6148-6152 (1985).

Walsh et al., "Update on chronic viral hepatitis", Postgrad Medical Journal, 77(910):498-505 (2001).

Wang et al., "Synthesis and Cytokine Modulation Properties of Pyrrolo[2,3,-d]-4-pyrimidone Nucleosides," J. Med. Chem., 43(13):2566.2574 (2000).

Wigler et al., Cell 11:223 (1977).

Wigler et al., *Proc. Natl. Acad. Sci. USA* 77:3567 (1980).

Winter G. and Milstein C; Nature 349:293-299 (1991).

Zhang et al., "Characterization of a monoclonal antibody and its singl-chain antibody fragment recognizing the nucleoside triphosphatase/helicase domain of the hepatitis C virus nonstructural 3 protein," Clin. Diagn. Lab. Immunol., 7(1 ):58-63 (2000).

Zhang et al., "Interferon.alpha. Treatment Induces Delayed CD4 Proliferative Responses to the Hepatitis C Virus Nonstructural Protein 3 Regardless of the Outcome of Therapy," The Journal of Infectious Diseases, 175:1294-1301 (1997).

Zhang et al., "Molecular basis for antibody cross-reactivity between the hepatitis C virs core protein and the hos-derived GOR protein," Clin. Exp. Immunol., 96(3):403-409 (1994).

* cited by examiner

Mean NS3 titer in EIA

Weeks after first immunization

SEQUENCE LISTING

```
<160> NUMBER OF SEQ ID NOS: 49

<210> SEQ ID NO 1
<211> LENGTH: 3011
<212> TYPE: PRT
<213> ORGANISM: Artificial Sequence
<220> FEATURE:
<223> OTHER INFORMATION: Hepatitis C virus sequence

<400> SEQUENCE: 1

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

```
Thr Arg Lys Thr Ser Glu Arg Ser Gln Pro Arg Gly Arg Gln Pro
         50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
        195                 200                 205

Asn Ser Ser Val Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Gly
        275                 280                 285

Gln Leu Phe Thr Phe Ser Pro Arg His His Trp Thr Thr Gln Asp Cys
        290                 295                 300

Asn Cys Ser Ile Tyr Pro Gly His Ile Thr Gly His Arg Met Ala Trp
305                 310                 315                 320

Asn Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
                340                 345                 350

Trp Gly Val Leu Ala Gly Ile Lys Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser Tyr Ala Asn Gly Ser Gly Leu
```

-continued

```
            465                 470                 475                 480
Asp Glu Arg Pro Tyr Cys Trp His Tyr Pro Pro Arg Pro Cys Gly Ile
                    485                 490                 495
Val Pro Ala Lys Ser Val Cys Gly Pro Val Tyr Cys Phe Thr Pro Ser
                500                 505                 510
Pro Val Val Gly Thr Thr Asp Arg Ser Gly Ala Pro Thr Tyr Ser
                515                 520                 525
Trp Gly Ala Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Val Gly Asn
                565                 570                 575
Asn Thr Leu Leu Cys Pro Thr Asp Cys Phe Arg Lys Tyr Pro Glu Ala
                580                 585                 590
Thr Tyr Ser Arg Cys Gly Ser Gly Pro Arg Ile Thr Pro Arg Cys Met
                595                 600                 605
Val Asp Tyr Pro Tyr Arg Leu Trp His Tyr Pro Cys Thr Ile Asn Tyr
            610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Gln Trp
                660                 665                 670
Gln Val Leu Pro Cys Ser Phe Thr Thr Leu Pro Ala Leu Ser Thr Gly
                675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Arg Trp Val Pro
            770                 775                 780
Gly Ala Val Tyr Ala Leu Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
                820                 825                 830
Pro Tyr Tyr Lys Arg Tyr Ile Ser Trp Cys Met Trp Trp Leu Gln Tyr
            835                 840                 845
Phe Leu Thr Arg Val Glu Ala Gln Leu His Val Trp Val Pro Pro Leu
            850                 855                 860
Asn Val Arg Gly Gly Arg Asp Ala Val Ile Leu Leu Thr Cys Val Val
865                 870                 875                 880
His Pro Ala Leu Val Phe Asp Ile Thr Lys Leu Leu Leu Ala Ile Phe
                885                 890                 895
```

-continued

Gly Pro Leu Trp Ile Leu Gln Ala Ser Leu Leu Lys Val Pro Tyr Phe
          900                 905                 910

Val Arg Val Gln Gly Leu Leu Arg Ile Cys Ala Leu Ala Arg Lys Ile
          915                 920                 925

Ala Gly Gly His Tyr Val Gln Met Ala Ile Ile Lys Leu Gly Ala Leu
          930                 935                 940

Thr Gly Thr Cys Val Tyr Asn His Leu Ala Pro Leu Arg Asp Trp Ala
945                 950                 955                 960

His Asn Gly Leu Arg Asp Leu Ala Val Ala Val Glu Pro Val Phe
              965                 970                 975

Ser Arg Met Glu Thr Lys Leu Ile Thr Trp Gly Ala Asp Thr Ala Ala
          980                 985                 990

Cys Gly Asp Ile Ile Asn Gly Leu Pro Val Ser Ala Arg Arg Gly Gln
          995                1000                1005

Glu Ile Leu Leu Gly Pro Ala Asp Gly Met Val Ser Lys Gly Trp Arg
         1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
         1045                1050                1055

Gly Glu Val Gln Ile Val Ser Thr Ala Thr Gln Thr Phe Leu Ala Thr
         1060                1065                1070

Cys Ile Asn Gly Val Cys Trp Thr Val Tyr His Gly Ala Gly Thr Arg
         1075                1080                1085

Thr Ile Ala Ser Pro Lys Gly Pro Val Ile Gln Thr Tyr Thr Asn Val
         1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
              1125                1130                1135

Ala Asp Val Ile Pro Val Arg Arg Arg Gly Asp Ser Arg Gly Ser Leu
         1140                1145                1150

Leu Ser Pro Arg Pro Ile Ser Tyr Leu Lys Gly Ser Ser Gly Gly Pro
         1155                1160                1165

Leu Leu Cys Pro Thr Gly His Ala Val Gly Leu Phe Arg Ala Ala Val
         1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
         1205                1210                1215

Pro Ala Val Pro Gln Ser Phe Gln Val Ala His Leu His Ala Pro Thr
         1220                1225                1230

Gly Ser Gly Lys Ser Thr Lys Val Pro Ala Ala Tyr Ala Ala Lys Gly
         1235                1240                1245

Tyr Lys Val Leu Val Leu Asn Pro Ser Val Ala Ala Thr Leu Gly Phe
         1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
              1285                1290                1295

Gly Lys Phe Leu Ala Asp Ala Gly Cys Ser Gly Gly Ala Tyr Asp Ile
         1300                1305                1310

```
Ile Ile Cys Asp Glu Cys His Ser Thr Asp Ala Thr Ser Ile Ser Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
        1365                1370                1375

Gly Lys Ala Ile Pro Leu Glu Val Ile Lys Gly Gly Arg His Leu Ile
        1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
        1445                1450                1455

Cys Val Thr Gln Thr Val Asp Phe Ser Leu Asp Pro Thr Phe Thr Ile
        1460                1465                1470

Glu Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
        1525                1530                1535

Val Arg Leu Arg Ala Tyr Met Asn Thr Pro Gly Leu Pro Val Cys Gln
        1540                1545                1550

Asp His Leu Gly Phe Trp Glu Gly Val Phe Thr Gly Leu Thr His Ile
        1555                1560                1565

Asp Ala His Phe Leu Ser Gln Thr Lys Gln Ser Gly Glu Asn Phe Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Arg Lys Cys Leu Ile Arg Leu Lys Pro
        1605                1610                1615

Thr Leu His Gly Pro Thr Pro Leu Leu Tyr Arg Leu Gly Ala Val Gln
        1620                1625                1630

Asn Glu Val Thr Leu Thr His Pro Ile Thr Lys Tyr Ile Met Thr Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
        1685                1690                1695

Asp Arg Glu Val Leu Tyr Gln Glu Phe Asp Glu Met Glu Glu Cys Ser
        1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala Glu
```

-continued

```
        1730                1735                1740
Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
                1780                1785                1790

Phe Thr Ala Ala Val Thr Ser Pro Leu Thr Thr Gly Gln Thr Leu Leu
                1795                1800                1805

Phe Asn Ile Leu Gly Gly Trp Val Ala Gln Leu Ala Ala Pro Gly
    1810                1815                1820

Ala Ala Thr Ala Phe Val Gly Ala Gly Leu Ala Gly Ala Ala Leu Asp
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
                1875                1880                1885

Pro Gly Ala Leu Ala Val Gly Val Val Phe Ala Ser Ile Leu Arg Arg
                1890                1895                1900

Arg Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
                1940                1945                1950

Val Thr Gln Leu Leu Arg Arg Leu His Gln Trp Ile Ser Ser Glu Cys
                1955                1960                1965

Thr Thr Pro Cys Ser Gly Ser Trp Leu Arg Asp Ile Trp Asp Trp Ile
                1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Lys Asn Met Trp Ser Gly Thr Phe Phe Ile Asn Ala
                2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
                2100                2105                2110

Pro Cys Gln Ile Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
                2130                2135                2140

Val Ser Phe Arg Val Gly Leu His Glu Tyr Pro Val Gly Ser Gln Leu
2145                2150                2155                2160
```

-continued

```
Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
            2180                2185                2190

Gly Ser Pro Pro Ser Met Ala Ser Ser Ala Ser Gln Leu Ser Ala
            2195                2200                2205

Pro Ser Leu Lys Ala Thr Cys Thr Ala Asn His Asp Ser Pro Asp Ala
            2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Val Ser Val Pro Ala
            2260                2265                2270

Glu Ile Leu Arg Lys Ser Arg Arg Phe Ala Pro Ala Leu Pro Val Trp
            2275                2280                2285

Ala Arg Pro Asp Tyr Asn Pro Leu Leu Val Glu Thr Trp Lys Lys Pro
            2290                2295                2300

Asp Tyr Glu Pro Pro Val Val His Gly Cys Pro Leu Pro Pro Pro Arg
2305                2310                2315                2320

Ser Pro Pro Val Pro Pro Arg Lys Lys Arg Thr Val Val Leu Thr
            2325                2330                2335

Glu Ser Thr Leu Pro Thr Ala Leu Ala Glu Leu Ala Thr Lys Ser Phe
            2340                2345                2350

Gly Ser Ser Ser Thr Ser Gly Ile Thr Gly Asp Asn Thr Thr Thr Ser
            2355                2360                2365

Ser Glu Pro Ala Pro Ser Gly Cys Pro Pro Asp Ser Asp Val Glu Ser
            2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Gly Ala Asp Thr Glu Asp
            2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
            2435                2440                2445

Ser Leu Leu Arg His His Asn Leu Val Tyr Ser Thr Thr Ser Arg Ser
            2450                2455                2460

Ala Cys Gln Arg Lys Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Ala
            2500                2505                2510

Pro Pro His Ser Ala Lys Ser Lys Phe Gly Tyr Gly Ala Lys Asp Val
            2515                2520                2525

Arg Cys His Ala Arg Lys Ala Val Ala His Ile Asn Ser Val Trp Lys
            2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
            2565                2570                2575
```

-continued

```
Ala Arg Leu Ile Val Phe Pro Asp Leu Gly Val Arg Val Cys Glu Lys
        2580                2585                2590
Met Ala Leu Tyr Asp Val Val Ser Lys Leu Pro Leu Ala Val Met Gly
            2595                2600                2605
Ser Ser Tyr Gly Phe Gln Tyr Ser Pro Gly Gln Arg Val Glu Phe Leu
    2610                2615                2620
Val Gln Ala Trp Lys Ser Lys Lys Thr Pro Met Gly Leu Ser Tyr Asp
2625                2630                2635                2640
Thr Arg Cys Phe Asp Ser Thr Val Thr Glu Ser Asp Ile Arg Thr Glu
            2645                2650                2655
Glu Ala Ile Tyr Gln Cys Cys Asp Leu Asp Pro Gln Ala Arg Val Ala
                2660                2665                2670
Ile Lys Ser Leu Thr Glu Arg Leu Tyr Val Gly Gly Pro Leu Thr Asn
            2675                2680                2685
Ser Arg Gly Glu Asn Cys Gly Tyr Arg Arg Cys Arg Ala Ser Arg Val
    2690                2695                2700
Leu Thr Thr Ser Cys Gly Asn Thr Leu Thr Arg Tyr Ile Lys Ala Arg
2705                2710                2715                2720
Ala Ala Cys Arg Ala Ala Gly Leu Gln Asp Cys Thr Met Leu Val Cys
            2725                2730                2735
Gly Asp Asp Leu Val Val Ile Cys Glu Ser Ala Gly Val Gln Glu Asp
            2740                2745                2750
Ala Ala Ser Leu Arg Ala Phe Thr Glu Ala Met Thr Arg Tyr Ser Ala
            2755                2760                2765
Pro Pro Gly Asp Pro Pro Gln Pro Glu Tyr Asp Leu Glu Leu Ile Thr
        2770                2775                2780
Ser Cys Ser Ser Asn Val Ser Val Ala His Asp Gly Ala Gly Lys Arg
2785                2790                2795                2800
Val Tyr Tyr Leu Thr Arg Asp Pro Thr Thr Pro Leu Ala Arg Ala Ala
                2805                2810                2815
Trp Glu Thr Ala Arg His Thr Pro Val Asn Ser Trp Leu Gly Asn Ile
            2820                2825                2830
Ile Met Phe Ala Pro Thr Leu Trp Ala Arg Met Ile Leu Met Thr His
    2835                2840                2845
Phe Phe Ser Val Leu Ile Ala Arg Asp Gln Leu Glu Gln Ala Leu Asn
2850                2855                2860
Cys Glu Ile Tyr Gly Ala Cys Tyr Ser Ile Glu Pro Leu Asp Leu Pro
2865                2870                2875                2880
Pro Ile Ile Gln Arg Leu His Gly Leu Ser Ala Phe Ser Leu His Ser
            2885                2890                2895
Tyr Ser Pro Gly Glu Ile Asn Arg Val Ala Ala Cys Leu Arg Lys Leu
    2900                2905                2910
Gly Val Pro Pro Leu Arg Ala Trp Arg His Arg Ala Trp Ser Val Arg
    2915                2920                2925
Ala Arg Leu Leu Ala Arg Gly Gly Lys Ala Ala Ile Cys Gly Lys Tyr
        2930                2935                2940
Leu Phe Asn Trp Ala Val Arg Thr Lys Leu Lys Leu Thr Pro Ile Thr
2945                2950                2955                2960
Ala Ala Gly Arg Leu Asp Leu Ser Gly Trp Phe Thr Ala Gly Tyr Ser
                2965                2970                2975
Gly Gly Asp Ile Tyr His Ser Val Ser His Ala Arg Pro Arg Trp Phe
            2980                2985                2990
Trp Phe Cys Leu Leu Leu Leu Ala Ala Gly Val Gly Ile Tyr Leu Leu
```

```
                2995             3000            3005

Pro Asn Arg
    3010

<210> SEQ ID NO 2
<211> LENGTH: 182
<212> TYPE: PRT
<213> ORGANISM: Artificial Sequence
<220> FEATURE:
<223> OTHER INFORMATION: Hepatitis C virus core protein sequence

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu
            180

<210> SEQ ID NO 3
<211> LENGTH: 197
<212> TYPE: PRT
<213> ORGANISM: Artificial Sequence
<220> FEATURE:
<223> OTHER INFORMATION: Hepatitis C virus E1 protein sequence

<400> SEQUENCE: 3

Ser Cys Leu Thr Val Pro Ala Ser Ala Tyr Gln Val Arg Asn Ser Ser
1               5                   10                  15

Gly Leu Tyr His Val Thr Asn Asp Cys Pro Asn Ser Ser Val Val Tyr
            20                  25                  30

Glu Ala Ala Asp Ala Ile Leu His Thr Pro Gly Cys Val Pro Cys Val
        35                  40                  45

Arg Glu Gly Asn Ala Ser Arg Cys Trp Val Ala Val Thr Pro Thr Val
    50                  55                  60

Ala Thr Arg Asp Gly Lys Leu Pro Thr Thr Gln Leu Arg Arg His Ile
65                  70                  75                  80

Asp Leu Leu Val Gly Ser Ala Thr Leu Cys Ser Ala Leu Tyr Val Gly
                85                  90                  95
```

-continued

```
Asp Leu Cys Gly Ser Val Phe Leu Val Gly Gln Leu Phe Thr Phe Ser
            100                 105                 110

Pro Arg His His Trp Thr Thr Gln Asp Cys Asn Cys Ser Ile Tyr Pro
        115                 120                 125

Gly His Ile Thr Gly His Arg Met Ala Trp Asn Met Met Met Asn Trp
    130                 135                 140

Ser Pro Thr Ala Ala Leu Val Val Ala Gln Leu Leu Arg Ile Pro Gln
145                 150                 155                 160

Ala Ile Met Asp Met Ile Ala Gly Ala His Trp Gly Val Leu Ala Gly
                165                 170                 175

Ile Lys Tyr Phe Ser Met Val Gly Asn Trp Ala Lys Val Leu Val Val
            180                 185                 190

Leu Leu Leu Phe Ala
        195

<210> SEQ ID NO 4
<211> LENGTH: 350
<212> TYPE: PRT
<213> ORGANISM: Artificial Sequence
<220> FEATURE:
<223> OTHER INFORMATION: Hepatitis C virus E2 protein sequence

<400> SEQUENCE: 4

Gly Val Asp Ala Glu Thr His Val Thr Gly Gly Asn Ala Gly Arg Thr
 1               5                  10                  15

Thr Ala Gly Leu Val Gly Leu Leu Thr Pro Gly Ala Lys Gln Asn Ile
            20                  25                  30

Gln Leu Ile Asn Thr Asn Gly Ser Trp His Ile Asn Ser Thr Ala Leu
        35                  40                  45

Asn Cys Asn Glu Ser Leu Asn Thr Gly Trp Leu Ala Gly Leu Phe Tyr
    50                  55                  60

Gln His Lys Phe Asn Ser Ser Gly Cys Pro Glu Arg Leu Ala Ser Cys
65                  70                  75                  80

Arg Arg Leu Thr Asp Phe Ala Gln Gly Trp Gly Pro Ile Ser Tyr Ala
                85                  90                  95

Asn Gly Ser Gly Leu Asp Glu Arg Pro Tyr Cys Trp His Tyr Pro Pro
            100                 105                 110

Arg Pro Cys Gly Ile Val Pro Ala Lys Ser Val Cys Gly Pro Val Tyr
        115                 120                 125

Cys Phe Thr Pro Ser Pro Val Val Val Gly Thr Thr Asp Arg Ser Gly
    130                 135                 140

Ala Pro Thr Tyr Ser Trp Gly Ala Asn Asp Thr Asp Val Phe Val Leu
145                 150                 155                 160

Asn Asn Thr Arg Pro Pro Leu Gly Asn Trp Phe Gly Cys Thr Trp Met
                165                 170                 175

Asn Ser Thr Gly Phe Thr Lys Val Cys Gly Ala Pro Pro Cys Val Ile
            180                 185                 190

Gly Gly Val Gly Asn Asn Thr Leu Leu Cys Pro Thr Asp Cys Phe Arg
        195                 200                 205

Lys Tyr Pro Glu Ala Thr Tyr Ser Arg Cys Gly Ser Gly Pro Arg Ile
    210                 215                 220

Thr Pro Arg Cys Met Val Asp Tyr Pro Tyr Arg Leu Trp His Tyr Pro
225                 230                 235                 240

Cys Thr Ile Asn Tyr Thr Ile Phe Lys Val Arg Met Tyr Val Gly Gly
                245                 250                 255
```

-continued

Val Glu His Arg Leu Glu Ala Ala Cys Asn Trp Thr Arg Gly Glu Arg
            260                 265                 270

Cys Asp Leu Glu Asp Arg Asp Arg Ser Glu Leu Ser Pro Leu Leu Leu
        275                 280                 285

Ser Thr Thr Gln Trp Gln Val Leu Pro Cys Ser Phe Thr Thr Leu Pro
    290                 295                 300

Ala Leu Ser Thr Gly Leu Ile His Leu His Gln Asn Ile Val Asp Val
305                 310                 315                 320

Gln Tyr Leu Tyr Gly Val Gly Ser Ser Ile Ala Ser Trp Ala Ile Lys
                325                 330                 335

Trp Glu Tyr Val Val Leu Leu Phe Leu Leu Leu Ala Asp Ala
                340                 345                 350

<210> SEQ ID NO 5
<211> LENGTH: 315
<212> TYPE: PRT
<213> ORGANISM: Artificial Sequence
<220> FEATURE:
<223> OTHER INFORMATION: Hepatitis C virus NS2 protein sequence

<400> SEQUENCE: 5

Arg Val Cys Ser Cys Leu Trp Met Met Leu Leu Ile Ser Gln Ala Glu
1               5                   10                  15

Ala Ala Leu Glu Asn Leu Val Ile Leu Asn Ala Ala Ser Leu Ala Gly
            20                  25                  30

Thr His Gly Leu Val Ser Phe Leu Val Phe Phe Cys Phe Ala Trp Tyr
        35                  40                  45

Leu Lys Gly Arg Trp Val Pro Gly Ala Val Tyr Ala Leu Tyr Gly Met
    50                  55                  60

Trp Pro Leu Leu Leu Leu Leu Ala Leu Pro Gln Arg Ala Tyr Ala
65                  70                  75                  80

Leu Asp Thr Glu Val Ala Ala Ser Cys Gly Gly Val Val Leu Val Gly
                85                  90                  95

Leu Met Ala Leu Thr Leu Ser Pro Tyr Tyr Lys Arg Tyr Ile Ser Trp
            100                 105                 110

Cys Met Trp Trp Leu Gln Tyr Phe Leu Thr Arg Val Glu Ala Gln Leu
        115                 120                 125

His Val Trp Val Pro Pro Leu Asn Val Arg Gly Gly Arg Asp Ala Val
    130                 135                 140

Ile Leu Leu Thr Cys Val Val His Pro Ala Leu Val Phe Asp Ile Thr
145                 150                 155                 160

Lys Leu Leu Leu Ala Ile Phe Gly Pro Leu Trp Ile Leu Gln Ala Ser
                165                 170                 175

Leu Leu Lys Val Pro Tyr Phe Val Arg Val Gln Gly Leu Leu Arg Ile
            180                 185                 190

Cys Ala Leu Ala Arg Lys Ile Ala Gly Gly His Tyr Val Gln Met Ala
        195                 200                 205

Ile Ile Lys Leu Gly Ala Leu Thr Gly Thr Cys Val Tyr Asn His Leu
    210                 215                 220

Ala Pro Leu Arg Asp Trp Ala His Asn Gly Leu Arg Asp Leu Ala Val
225                 230                 235                 240

Ala Val Glu Pro Val Val Phe Ser Arg Met Glu Thr Lys Leu Ile Thr
                245                 250                 255

Trp Gly Ala Asp Thr Ala Ala Cys Gly Asp Ile Ile Asn Gly Leu Pro
            260                 265                 270

-continued

```
Val Ser Ala Arg Arg Gly Gln Glu Ile Leu Leu Gly Pro Ala Asp Gly
            275                 280                 285

Met Val Ser Lys Gly Trp Arg Leu Leu Ala Pro Ile Thr Ala Tyr Ala
        290                 295                 300

Gln Gln Thr Arg Gly Leu Leu Gly Cys Ile Ile
305                 310                 315

<210> SEQ ID NO 6
<211> LENGTH: 613
<212> TYPE: PRT
<213> ORGANISM: Artificial Sequence
<220> FEATURE:
<223> OTHER INFORMATION: Hepatitis C virus NS3 protein sequence

<400> SEQUENCE: 6

Thr Ser Leu Thr Gly Arg Asp Lys Asn Gln Val Glu Gly Glu Val Gln
  1               5                  10                  15

Ile Val Ser Thr Ala Thr Gln Thr Phe Leu Ala Thr Cys Ile Asn Gly
             20                  25                  30

Val Cys Trp Thr Val Tyr His Gly Ala Gly Thr Arg Thr Ile Ala Ser
         35                  40                  45

Pro Lys Gly Pro Val Ile Gln Thr Tyr Thr Asn Val Asp Gln Asp Leu
     50                  55                  60

Val Gly Trp Pro Ala Pro Gln Gly Ser Arg Ser Leu Thr Pro Cys Thr
 65                  70                  75                  80

Cys Gly Ser Ser Asp Leu Tyr Leu Val Thr Arg His Ala Asp Val Ile
                 85                  90                  95

Pro Val Arg Arg Arg Gly Asp Ser Arg Gly Ser Leu Leu Ser Pro Arg
            100                 105                 110

Pro Ile Ser Tyr Leu Lys Gly Ser Ser Gly Gly Pro Leu Leu Cys Pro
        115                 120                 125

Thr Gly His Ala Val Gly Leu Phe Arg Ala Ala Val Cys Thr Arg Gly
    130                 135                 140

Val Ala Lys Ala Val Asp Phe Ile Pro Val Glu Asn Leu Glu Thr Thr
145                 150                 155                 160

Met Arg Ser Pro Val Phe Thr Asp Asn Ser Ser Pro Pro Ala Val Pro
                165                 170                 175

Gln Ser Phe Gln Val Ala His Leu His Ala Pro Thr Gly Ser Gly Lys
            180                 185                 190

Ser Thr Lys Val Pro Ala Ala Tyr Ala Ala Lys Gly Tyr Lys Val Leu
        195                 200                 205

Val Leu Asn Pro Ser Val Ala Ala Thr Leu Gly Phe Gly Ala Tyr Met
    210                 215                 220

Ser Lys Ala His Gly Val Asp Pro Asn Ile Arg Thr Gly Val Arg Thr
225                 230                 235                 240

Ile Thr Thr Gly Ser Pro Ile Thr Tyr Ser Thr Tyr Gly Lys Phe Leu
                245                 250                 255

Ala Asp Ala Gly Cys Ser Gly Gly Ala Tyr Asp Ile Ile Ile Cys Asp
            260                 265                 270

Glu Cys His Ser Thr Asp Ala Thr Ser Ile Ser Gly Ile Gly Thr Val
        275                 280                 285

Leu Asp Gln Ala Glu Thr Ala Gly Ala Arg Leu Val Val Leu Ala Thr
    290                 295                 300

Ala Thr Pro Pro Gly Ser Val Thr Val Ser His Pro Asn Ile Glu Glu
305                 310                 315                 320
```

-continued

```
Val Ala Leu Ser Thr Thr Gly Glu Ile Pro Phe Tyr Gly Lys Ala Ile
                325                 330                 335

Pro Leu Glu Val Ile Lys Gly Gly Arg His Leu Ile Phe Cys His Ser
            340                 345                 350

Lys Lys Lys Cys Asp Glu Leu Ala Ala Lys Leu Val Ala Leu Gly Ile
        355                 360                 365

Asn Ala Val Ala Tyr Tyr Arg Gly Leu Asp Val Ser Val Ile Pro Thr
    370                 375                 380

Ser Gly Asp Val Val Val Val Ser Thr Asp Ala Leu Met Thr Gly Phe
385                 390                 395                 400

Thr Gly Asp Phe Asp Ser Val Ile Asp Cys Asn Thr Cys Val Thr Gln
                405                 410                 415

Thr Val Asp Phe Ser Leu Asp Pro Thr Phe Thr Ile Glu Thr Thr Thr
            420                 425                 430

Leu Pro Gln Asp Ala Val Ser Arg Thr Gln Arg Arg Gly Arg Thr Gly
        435                 440                 445

Arg Gly Lys Pro Gly Ile Tyr Arg Phe Val Ala Pro Gly Glu Arg Pro
    450                 455                 460

Ser Gly Met Phe Asp Ser Ser Val Leu Cys Glu Cys Tyr Asp Ala Gly
465                 470                 475                 480

Cys Ala Trp Tyr Glu Leu Thr Pro Ala Glu Thr Thr Val Arg Leu Arg
                485                 490                 495

Ala Tyr Met Asn Thr Pro Gly Leu Pro Val Cys Gln Asp His Leu Gly
            500                 505                 510

Phe Trp Glu Gly Val Phe Thr Gly Leu Thr His Ile Asp Ala His Phe
        515                 520                 525

Leu Ser Gln Thr Lys Gln Ser Gly Glu Asn Phe Pro Tyr Leu Val Ala
    530                 535                 540

Tyr Gln Ala Thr Val Cys Ala Arg Ala Gln Ala Pro Pro Pro Ser Trp
545                 550                 555                 560

Asp Gln Met Arg Lys Cys Leu Ile Arg Leu Lys Pro Thr Leu His Gly
                565                 570                 575

Pro Thr Pro Leu Leu Tyr Arg Leu Gly Ala Val Gln Asn Glu Val Thr
            580                 585                 590

Leu Thr His Pro Ile Thr Lys Tyr Ile Met Thr Cys Met Ser Ala Asp
        595                 600                 605

Leu Glu Val Val Thr
    610
```

<210> SEQ ID NO 7
<211> LENGTH: 54
<212> TYPE: PRT
<213> ORGANISM: Artificial Sequence
<220> FEATURE:
<223> OTHER INFORMATION: Hepatitis C virus NS4A protein sequence

<400> SEQUENCE: 7

```
Ser Thr Trp Val Leu Val Gly Gly Val Leu Ala Ala Leu Ala Ala Tyr
 1               5                  10                  15

Cys Leu Ser Thr Gly Cys Val Val Ile Val Gly Arg Ile Val Leu Ser
            20                  25                  30

Gly Lys Pro Ala Ile Ile Pro Asp Arg Glu Val Leu Tyr Gln Glu Phe
        35                  40                  45

Asp Glu Met Glu Glu Cys
    50
```

```
<210> SEQ ID NO 8
<211> LENGTH: 260
<212> TYPE: PRT
<213> ORGANISM: Artificial Sequence
<220> FEATURE:
<223> OTHER INFORMATION: Hepatitis C virus NS4B protein sequence

<400> SEQUENCE: 8

Ser Gln His Leu Pro Tyr Ile Glu Gln Gly Met Met Leu Ala Glu Gln
  1               5                  10                  15

Phe Lys Gln Lys Ala Leu Gly Leu Leu Gln Thr Ala Ser Arg His Ala
             20                  25                  30

Glu Val Ile Thr Pro Ala Val Gln Thr Asn Trp Gln Lys Leu Glu Val
         35                  40                  45

Phe Trp Ala Lys His Met Trp Asn Phe Ile Ser Gly Ile Gln Tyr Leu
     50                  55                  60

Ala Gly Leu Ser Thr Leu Pro Gly Asn Pro Ala Ile Ala Ser Leu Met
 65                  70                  75                  80

Ala Phe Thr Ala Ala Val Thr Ser Pro Leu Thr Thr Gly Gln Thr Leu
                 85                  90                  95

Leu Phe Asn Ile Leu Gly Gly Trp Val Ala Ala Gln Leu Ala Ala Pro
            100                 105                 110

Gly Ala Ala Thr Ala Phe Val Gly Ala Gly Leu Ala Gly Ala Ala Leu
        115                 120                 125

Asp Ser Val Gly Leu Gly Lys Val Leu Val Asp Ile Leu Ala Gly Tyr
    130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Ala Val Gly Val Val Phe Ala Ser Ile Leu Arg
            180                 185                 190

Arg Arg Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro
            260

<210> SEQ ID NO 9
<211> LENGTH: 1040
<212> TYPE: PRT
<213> ORGANISM: Artificial Sequence
<220> FEATURE:
<223> OTHER INFORMATION: Hepatitis C virus NS5A/B protein sequence

<400> SEQUENCE: 9

Cys Ser Gly Ser Trp Leu Arg Asp Ile Trp Asp Trp Ile Cys Glu Val
  1               5                  10                  15

Leu Ser Asp Phe Lys Thr Trp Leu Lys Ala Lys Leu Met Pro Gln Leu
             20                  25                  30

Pro Gly Ile Pro Phe Val Ser Cys Gln Arg Gly Tyr Arg Gly Val Trp
         35                  40                  45
```

-continued

```
Arg Gly Asp Gly Ile Met His Thr Arg Cys His Cys Gly Ala Glu Ile
 50                  55                  60
Thr Gly His Val Lys Asn Gly Thr Met Arg Ile Val Gly Pro Arg Thr
 65                  70                  75                  80
Cys Lys Asn Met Trp Ser Gly Thr Phe Phe Ile Asn Ala Tyr Thr Thr
                 85                  90                  95
Gly Pro Cys Thr Pro Leu Pro Ala Pro Asn Tyr Lys Phe Ala Leu Trp
            100                 105                 110
Arg Val Ser Ala Glu Glu Tyr Val Glu Ile Arg Arg Val Gly Asp Phe
        115                 120                 125
His Tyr Val Ser Gly Met Thr Thr Asp Asn Leu Lys Cys Pro Cys Gln
    130                 135                 140
Ile Pro Ser Pro Glu Phe Phe Thr Glu Leu Asp Gly Val Arg Leu His
145                 150                 155                 160
Arg Phe Ala Pro Pro Cys Lys Pro Leu Leu Arg Glu Glu Val Ser Phe
                165                 170                 175
Arg Val Gly Leu His Glu Tyr Pro Val Gly Ser Gln Leu Pro Cys Glu
            180                 185                 190
Pro Glu Pro Asp Val Ala Val Leu Thr Ser Met Leu Thr Asp Pro Ser
        195                 200                 205
His Ile Thr Ala Glu Ala Ala Gly Arg Arg Leu Ala Arg Gly Ser Pro
    210                 215                 220
Pro Ser Met Ala Ser Ser Ser Ala Ser Gln Leu Ser Ala Pro Ser Leu
225                 230                 235                 240
Lys Ala Thr Cys Thr Ala Asn His Asp Ser Pro Asp Ala Glu Leu Ile
                245                 250                 255
Glu Ala Asn Leu Leu Trp Arg Gln Glu Met Gly Gly Asn Ile Thr Arg
            260                 265                 270
Val Glu Ser Glu Asn Lys Val Val Ile Leu Asp Ser Phe Asp Pro Leu
        275                 280                 285
Val Ala Glu Glu Asp Glu Arg Glu Val Ser Val Pro Ala Glu Ile Leu
    290                 295                 300
Arg Lys Ser Arg Arg Phe Ala Pro Ala Leu Pro Val Trp Ala Arg Pro
305                 310                 315                 320
Asp Tyr Asn Pro Leu Leu Val Glu Thr Trp Lys Lys Pro Asp Tyr Glu
                325                 330                 335
Pro Pro Val Val His Gly Cys Pro Leu Pro Pro Arg Ser Pro Pro
            340                 345                 350
Val Pro Pro Pro Arg Lys Lys Arg Thr Val Val Leu Thr Glu Ser Thr
        355                 360                 365
Leu Pro Thr Ala Leu Ala Glu Leu Ala Thr Lys Ser Phe Gly Ser Ser
    370                 375                 380
Ser Thr Ser Gly Ile Thr Gly Asp Asn Thr Thr Thr Ser Ser Glu Pro
385                 390                 395                 400
Ala Pro Ser Gly Cys Pro Pro Asp Ser Asp Val Glu Ser Tyr Ser Ser
                405                 410                 415
Met Pro Pro Leu Glu Gly Glu Pro Gly Asp Pro Asp Leu Ser Asp Gly
            420                 425                 430
Ser Trp Ser Thr Val Ser Ser Gly Ala Asp Thr Glu Asp Val Val Cys
        435                 440                 445
Cys Ser Met Ser Tyr Ser Trp Thr Gly Ala Leu Val Thr Pro Cys Ala
    450                 455                 460
```

-continued

```
Ala Glu Glu Gln Lys Leu Pro Ile Asn Ala Leu Ser Asn Ser Leu Leu
465                 470                 475                 480

Arg His His Asn Leu Val Tyr Ser Thr Thr Ser Arg Ser Ala Cys Gln
                485                 490                 495

Arg Lys Lys Lys Val Thr Phe Asp Arg Leu Gln Val Leu Asp Ser His
                500                 505                 510

Tyr Gln Asp Val Leu Lys Glu Val Lys Ala Ala Ser Lys Val Lys
            515                 520                 525

Ala Asn Leu Leu Ser Val Glu Glu Ala Cys Ser Leu Ala Pro Pro His
        530                 535                 540

Ser Ala Lys Ser Lys Phe Gly Tyr Gly Ala Lys Asp Val Arg Cys His
545                 550                 555                 560

Ala Arg Lys Ala Val Ala His Ile Asn Ser Val Trp Lys Asp Leu Leu
                565                 570                 575

Glu Asp Ser Val Thr Pro Ile Asp Thr Thr Ile Met Ala Lys Asn Glu
                580                 585                 590

Val Phe Cys Val Gln Pro Glu Lys Gly Gly Arg Lys Pro Ala Arg Leu
            595                 600                 605

Ile Val Phe Pro Asp Leu Gly Val Arg Val Cys Glu Lys Met Ala Leu
610                 615                 620

Tyr Asp Val Val Ser Lys Leu Pro Leu Ala Val Met Gly Ser Ser Tyr
625                 630                 635                 640

Gly Phe Gln Tyr Ser Pro Gly Gln Arg Val Glu Phe Leu Val Gln Ala
                645                 650                 655

Trp Lys Ser Lys Lys Thr Pro Met Gly Leu Ser Tyr Asp Thr Arg Cys
                660                 665                 670

Phe Asp Ser Thr Val Thr Glu Ser Asp Ile Arg Thr Glu Glu Ala Ile
                675                 680                 685

Tyr Gln Cys Cys Asp Leu Asp Pro Gln Ala Arg Val Ala Ile Lys Ser
690                 695                 700

Leu Thr Glu Arg Leu Tyr Val Gly Gly Pro Leu Thr Asn Ser Arg Gly
705                 710                 715                 720

Glu Asn Cys Gly Tyr Arg Arg Cys Arg Ala Ser Arg Val Leu Thr Thr
                725                 730                 735

Ser Cys Gly Asn Thr Leu Thr Arg Tyr Ile Lys Ala Arg Ala Ala Cys
                740                 745                 750

Arg Ala Ala Gly Leu Gln Asp Cys Thr Met Leu Val Cys Gly Asp Asp
            755                 760                 765

Leu Val Val Ile Cys Glu Ser Ala Gly Val Gln Glu Asp Ala Ala Ser
770                 775                 780

Leu Arg Ala Phe Thr Glu Ala Met Thr Arg Tyr Ser Ala Pro Pro Gly
785                 790                 795                 800

Asp Pro Pro Gln Pro Glu Tyr Asp Leu Glu Leu Ile Thr Ser Cys Ser
                805                 810                 815

Ser Asn Val Ser Val Ala His Asp Gly Ala Gly Lys Arg Val Tyr Tyr
                820                 825                 830

Leu Thr Arg Asp Pro Thr Thr Pro Leu Ala Arg Ala Ala Trp Glu Thr
            835                 840                 845

Ala Arg His Thr Pro Val Asn Ser Trp Leu Gly Asn Ile Ile Met Phe
        850                 855                 860

Ala Pro Thr Leu Trp Ala Arg Met Ile Leu Met Thr His Phe Phe Ser
865                 870                 875                 880

Val Leu Ile Ala Arg Asp Gln Leu Glu Gln Ala Leu Asn Cys Glu Ile
```

-continued 885 890 895

Tyr Gly Ala Cys Tyr Ser Ile Glu Pro Leu Asp Leu Pro Pro Ile Ile
900 905 910

Gln Arg Leu His Gly Leu Ser Ala Phe Ser Leu His Ser Tyr Ser Pro
915 920 925

Gly Glu Ile Asn Arg Val Ala Ala Cys Leu Arg Lys Leu Gly Val Pro
930 935 940

Pro Leu Arg Ala Trp Arg His Arg Ala Trp Ser Val Arg Ala Arg Leu
945 950 955 960

Leu Ala Arg Gly Gly Lys Ala Ala Ile Cys Gly Lys Tyr Leu Phe Asn
965 970 975

Trp Ala Val Arg Thr Lys Leu Lys Leu Thr Pro Ile Thr Ala Ala Gly
980 985 990

Arg Leu Asp Leu Ser Gly Trp Phe Thr Ala Gly Tyr Ser Gly Gly Asp
995 1000 1005

Ile Tyr His Ser Val Ser His Ala Arg Pro Arg Trp Phe Trp Phe Cys
1010 1015 1020

Leu Leu Leu Leu Ala Ala Gly Val Gly Ile Tyr Leu Leu Pro Asn Arg
1025 1030 1035 1040

<210> SEQ ID NO 10
<211> LENGTH: 226
<212> TYPE: PRT
<213> ORGANISM: Artificial Sequence
<220> FEATURE:
<223> OTHER INFORMATION: Hepatitis B virus S antigen (HBsAg) sequence

<400> SEQUENCE: 10

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Thr Thr Val Cys
35 40 45

Leu Gly Gln Asn Ser Gln Ser Pro Thr Ser Asn His Ser Pro Thr Ser
50 55 60

Cys Pro Pro Thr Cys Pro Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Ser Ser Thr Thr Ser Thr Gly Pro Cys Arg Thr Cys Met Thr Thr Ala
115 120 125

Gln Gly Thr Ser Met Tyr Pro Ser Cys Cys Cys Thr Lys Pro Ser Asp
130 135 140

Gly Asn Cys Thr Cys Ile Pro Ile Pro Ser Ser Trp Ala Phe Gly Lys
145 150 155 160

Phe Leu Trp Glu Trp Ala Ser Ala Arg Phe Ser Trp Leu Ser Leu Leu
165 170 175

Val Pro Phe Val Gln Trp Phe Val Gly Leu Ser Pro Thr Val Trp Leu
180 185 190

Ser Val Ile Trp Met Met Trp Tyr Trp Gly Pro Ser Leu Tyr Ser Ile
195 200 205

Leu Ser Pro Phe Leu Pro Leu Leu Pro Ile Phe Phe Cys Leu Trp Val

-continued

```
    210                 215                 220

Tyr Ile
225

<210> SEQ ID NO 11
<211> LENGTH: 212
<212> TYPE: PRT
<213> ORGANISM: Artificial Sequence
<220> FEATURE:
<223> OTHER INFORMATION: Hepatitis B virus C antigen and e antigen
      (HBcAg/HBeAg) sequence

<400> SEQUENCE: 11

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 12
<211> LENGTH: 2227
<212> TYPE: PRT
<213> ORGANISM: Artificial Sequence
<220> FEATURE:
<223> OTHER INFORMATION: Hepatitis A virus sequence

<400> SEQUENCE: 12

Met Asn Met Ser Lys Gln Gly Ile Phe Gln Thr Val Gly Ser Gly Leu
 1               5                  10                  15

Asp His Ile Leu Ser Leu Ala Asp Ile Glu Glu Glu Gln Met Ile Gln
            20                  25                  30

Ser Val Asp Arg Thr Ala Val Thr Gly Ala Ser Tyr Phe Thr Ser Val
        35                  40                  45

Asp Gln Ser Ser Val His Thr Ala Glu Val Gly Ser His Gln Ile Glu
    50                  55                  60
```

```
Pro Leu Lys Thr Ser Val Asp Lys Pro Gly Ser Lys Lys Thr Gln Gly
 65                  70                  75                  80

Glu Lys Phe Phe Leu Ile His Ser Ala Asp Trp Leu Thr Thr His Ala
             85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
            115                 120                 125

Phe Gly Ile Glu Ile Gln Val Gln Ile Asn Pro Thr Pro Phe Gln Gln
        130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
            180                 185                 190

Tyr His Phe Lys Asp Pro Gln Tyr Pro Val Trp Glu Leu Thr Ile Arg
        195                 200                 205

Val Trp Ser Glu Leu Asn Ile Gly Thr Gly Thr Ser Ala Tyr Thr Ser
210                 215                 220

Leu Asn Val Leu Ala Arg Phe Thr Asp Leu Glu Leu His Gly Leu Thr
225                 230                 235                 240

Pro Leu Ser Thr Gln Met Met Arg Asn Glu Phe Arg Val Ser Thr Thr
                245                 250                 255

Glu Asn Val Val Asn Leu Ser Asn Tyr Glu Asp Ala Arg Ala Lys Met
            260                 265                 270

Ser Phe Ala Leu Asp Gln Glu Asp Trp Lys Ser Asp Pro Ser Gln Gly
        275                 280                 285

Gly Gly Ile Lys Ile Thr His Phe Thr Thr Trp Thr Ser Ile Pro Thr
290                 295                 300

Leu Ala Ala Gln Phe Pro Phe Asn Ala Ser Asp Ser Val Gly Gln Gln
305                 310                 315                 320

Ile Lys Val Ile Pro Val Asp Pro Tyr Phe Phe Gln Met Thr Asn Thr
                325                 330                 335

Asn Pro Asp Gln Lys Cys Ile Thr Ala Leu Ala Ser Ile Cys Gln Met
            340                 345                 350

Phe Cys Phe Trp Arg Gly Asp Leu Val Phe Asp Phe Gln Val Phe Pro
        355                 360                 365

Thr Lys Tyr His Ser Gly Arg Leu Leu Phe Cys Phe Val Pro Gly Asn
370                 375                 380

Glu Leu Ile Asp Val Thr Gly Ile Thr Leu Lys Gln Ala Thr Thr Ala
385                 390                 395                 400

Pro Cys Ala Val Met Asp Ile Thr Gly Val Gln Ser Thr Leu Arg Phe
                405                 410                 415

Arg Val Pro Trp Ile Ser Asp Thr Pro Tyr Arg Val Asn Arg Tyr Thr
            420                 425                 430

Lys Ser Ala His Gln Lys Gly Glu Tyr Thr Ala Ile Gly Lys Leu Ile
        435                 440                 445

Val Tyr Cys Tyr Asn Arg Leu Thr Ser Pro Ser Asn Val Ala Ser His
450                 455                 460

Val Arg Val Asn Val Tyr Leu Ser Ala Ile Asn Leu Glu Cys Phe Ala
465                 470                 475                 480
```

```
Pro Leu Tyr His Ala Met Asp Val Thr Thr Gln Val Gly Asp Asp Ser
            485                 490                 495

Gly Gly Phe Ser Thr Thr Val Ser Thr Glu Gln Asn Val Pro Asp Pro
            500                 505                 510

Gln Val Gly Ile Thr Thr Met Arg Asp Leu Lys Gly Lys Ala Asn Arg
            515                 520                 525

Gly Lys Met Asp Val Ser Gly Val Gln Ala Pro Arg Gly Ser Tyr Gln
            530                 535                 540

Gln Gln Leu Asn Asp Pro Val Leu Ala Lys Lys Val Pro Glu Thr Phe
545                 550                 555                 560

Pro Glu Leu Lys Pro Gly Glu Ser Arg His Thr Ser Asp His Met Ser
            565                 570                 575

Ile Tyr Lys Phe Met Gly Arg Ser His Phe Leu Cys Thr Phe Thr Phe
            580                 585                 590

Asn Ser Asn Asn Lys Glu Tyr Thr Phe Pro Ile Thr Leu Ser Ser Thr
            595                 600                 605

Ser Asn Pro Pro His Gly Leu Pro Ser Thr Leu Arg Trp Phe Phe Asn
            610                 615                 620

Leu Phe Gln Leu Tyr Arg Gly Pro Leu Asp Leu Thr Ile Ile Ile Thr
625                 630                 635                 640

Gly Ala Thr Asp Val Asp Gly Met Ala Trp Phe Thr Pro Val Gly Leu
            645                 650                 655

Ala Val Asp Pro Trp Val Glu Lys Glu Ser Ala Leu Ser Ile Asp Tyr
            660                 665                 670

Lys Thr Ala Leu Gly Ala Val Arg Phe Asn Thr Arg Thr Gly Asn
            675                 680                 685

Ile Gln Ile Arg Leu Pro Trp Tyr Ser Tyr Leu Tyr Ala Val Ser Gly
            690                 695                 700

Ala Leu Asp Gly Leu Gly Asp Lys Thr Asp Ser Thr Phe Gly Leu Phe
705                 710                 715                 720

Leu Phe Glu Ile Ala Asn Tyr Asn His Ser Asp Glu Tyr Leu Ser Phe
            725                 730                 735

Ser Cys Tyr Leu Ser Val Thr Glu Gln Ser Glu Phe Tyr Phe Pro Arg
            740                 745                 750

Ala Pro Leu Asn Ser Asn Ala Met Leu Ser Thr Glu Ser Met Met Ser
            755                 760                 765

Arg Ile Ala Ala Gly Asp Leu Glu Ser Ser Val Asp Asp Pro Arg Ser
770                 775                 780

Glu Glu Asp Arg Arg Phe Glu Ser His Ile Glu Cys Arg Lys Pro Tyr
785                 790                 795                 800

Lys Glu Leu Arg Leu Glu Val Gly Lys Gln Arg Leu Lys Tyr Ala Gln
            805                 810                 815

Glu Glu Leu Ser Asn Glu Val Leu Pro Pro Arg Lys Met Lys Gly
            820                 825                 830

Leu Phe Ser Gln Ala Lys Ile Ser Leu Phe Tyr Thr Glu Glu His Glu
            835                 840                 845

Ile Met Lys Phe Ser Trp Arg Gly Val Thr Ala Asp Thr Arg Ala Leu
            850                 855                 860

Arg Arg Phe Gly Phe Ser Leu Ala Ala Gly Arg Ser Val Trp Thr Leu
865                 870                 875                 880

Glu Met Asp Ala Gly Val Leu Thr Gly Arg Leu Ile Arg Leu Asn Asp
            885                 890                 895

Glu Lys Trp Thr Glu Met Lys Asp Asp Lys Ile Val Ser Leu Ile Glu
```

-continued

```
                900             905             910
Lys Phe Thr Ser Asn Lys Tyr Trp Ser Lys Val Asn Phe Pro His Gly
        915                 920                 925
Met Leu Asp Leu Glu Glu Ile Ala Ala Asn Ser Lys Asp Phe Pro Asn
        930                 935                 940
Met Ser Glu Thr Asp Leu Cys Phe Leu Leu His Trp Leu Asn Pro Lys
945                 950                 955                 960
Lys Ile Asn Leu Ala Asp Arg Met Leu Gly Leu Ser Gly Val Gln Glu
            965                 970                 975
Ile Lys Glu Gln Gly Val Gly Leu Ile Ala Glu Cys Arg Thr Phe Leu
            980                 985                 990
Asp Ser Ile Ala Gly Thr Leu Lys Ser Met Met Phe Gly Phe His His
            995                 1000                1005
Ser Val Thr Val Glu Ile Ile Asn Thr Val Leu Cys Phe Val Lys Ser
        1010                1015                1020
Gly Ile Leu Leu Tyr Val Ile Gln Gln Leu Asn Gln Asp Glu His Ser
1025                1030                1035                1040
His Ile Ile Gly Leu Leu Arg Val Met Asn Tyr Ala Asp Ile Gly Cys
            1045                1050                1055
Ser Val Ile Ser Cys Gly Lys Val Phe Ser Lys Met Leu Glu Thr Val
            1060                1065                1070
Phe Asn Trp Gln Met Asp Ser Arg Met Met Glu Leu Arg Thr Gln Ser
            1075                1080                1085
Phe Ser Asn Trp Leu Arg Asp Ile Cys Ser Gly Ile Thr Ile Phe Lys
            1090                1095                1100
Ser Phe Lys Asp Ala Ile Tyr Trp Leu Tyr Thr Lys Leu Lys Asp Phe
1105                1110                1115                1120
Tyr Glu Val Asn Tyr Gly Lys Lys Asp Ile Leu Asn Ile Leu Lys
            1125                1130                1135
Asp Asn Gln Gln Lys Ile Glu Lys Ala Ile Glu Ala Asp Asn Phe
            1140                1145                1150
Cys Ile Leu Gln Ile Gln Asp Val Glu Lys Phe Asp Gln Tyr Gln Lys
            1155                1160                1165
Gly Val Asp Leu Ile Gln Lys Leu Arg Thr Val His Ser Met Ala Gln
            1170                1175                1180
Val Asp Pro Asn Leu Gly Val His Leu Ser Pro Leu Arg Asp Cys Ile
1185                1190                1195                1200
Ala Arg Val His Gln Lys Leu Lys Asn Leu Gly Ser Ile Asn Gln Ala
            1205                1210                1215
Met Val Thr Arg Cys Glu Pro Val Cys Tyr Leu Tyr Gly Lys Arg
            1220                1225                1230
Gly Gly Gly Lys Ser Leu Thr Ser Ile Ala Leu Ala Thr Lys Ile Cys
            1235                1240                1245
Lys His Tyr Gly Val Glu Pro Glu Lys Asn Ile Tyr Thr Lys Pro Val
            1250                1255                1260
Ala Ser Asp Tyr Trp Asp Gly Tyr Ser Gly Gln Leu Val Cys Ile Ile
1265                1270                1275                1280
Asp Asp Ile Gly Gln Asn Thr Thr Asp Glu Asp Trp Ser Asp Phe Cys
            1285                1290                1295
Gln Leu Val Ser Gly Cys Pro Met Arg Leu Asn Met Ala Ser Leu Glu
            1300                1305                1310
Glu Lys Gly Arg His Phe Ser Ser Pro Phe Ile Ile Ala Thr Ser Asn
            1315                1320                1325
```

```
Trp Ser Asn Pro Ser Pro Lys Thr Val Tyr Val Lys Glu Ala Ile Asp
    1330            1335                1340

Arg Arg Leu His Phe Lys Val Glu Val Lys Pro Ala Ser Phe Phe Lys
1345            1350                1355                1360

Asn Pro His Asn Asp Met Leu Asn Val Asn Leu Ala Lys Thr Asn Asp
            1365                1370                1375

Ala Ile Lys Asp Met Ser Cys Val Asp Leu Ile Met Asp Gly His Asn
        1380                1385                1390

Ile Ser Leu Met Asp Leu Leu Ser Ser Leu Val Met Thr Val Glu Ile
            1395                1400                1405

Arg Lys Gln Asn Met Ser Glu Phe Met Glu Leu Trp Ser Gln Gly Ile
    1410                1415                1420

Ser Asp Asp Asn Asp Ser Ala Val Ala Glu Phe Phe Gln Ser Phe
1425                1430                1435                1440

Pro Ser Gly Glu Pro Ser Asn Trp Lys Leu Ser Ser Phe Phe Gln Ser
            1445                1450                1455

Val Thr Asn His Lys Trp Val Ala Val Gly Ala Ala Val Gly Ile Leu
            1460                1465                1470

Gly Val Leu Val Gly Gly Trp Phe Val Tyr Lys His Phe Ser Arg Lys
        1475                1480                1485

Glu Glu Glu Pro Ile Pro Ala Glu Gly Val Tyr His Gly Val Thr Lys
    1490                1495                1500

Pro Lys Gln Val Ile Lys Leu Asp Ala Asp Pro Val Glu Ser Gln Ser
1505                1510                1515                1520

Thr Leu Glu Ile Ala Gly Leu Val Arg Lys Asn Leu Val Gln Phe Gly
            1525                1530                1535

Val Gly Glu Lys Asn Gly Cys Val Arg Trp Val Met Asn Ala Leu Gly
            1540                1545                1550

Val Lys Asp Asp Trp Leu Leu Val Pro Ser His Ala Tyr Lys Phe Glu
            1555                1560                1565

Lys Asp Tyr Glu Met Met Glu Phe Tyr Phe Asn Arg Gly Gly Thr Tyr
    1570                1575                1580

Tyr Ser Ile Ser Ala Gly Asn Val Val Ile Gln Ser Leu Asp Val Gly
1585                1590                1595                1600

Phe Gln Asp Val Val Leu Met Lys Val Pro Thr Ile Pro Lys Phe Arg
            1605                1610                1615

Asp Ile Thr Gln His Phe Ile Lys Lys Gly Asp Val Pro Arg Ala Leu
            1620                1625                1630

Asn Arg Leu Ala Thr Leu Val Thr Thr Val Asn Gly Thr Pro Met Leu
    1635                1640                1645

Ile Ser Glu Gly Pro Leu Lys Met Glu Glu Lys Ala Thr Tyr Val His
    1650                1655                1660

Lys Lys Asn Asp Gly Thr Thr Val Asp Leu Thr Val Asp Gln Ala Trp
1665                1670                1675                1680

Arg Gly Lys Gly Glu Gly Leu Pro Gly Met Cys Gly Gly Ala Leu Val
            1685                1690                1695

Ser Ser Asn Gln Ser Ile Gln Asn Ala Ile Leu Gly Ile His Val Ala
            1700                1705                1710

Gly Gly Asn Ser Ile Leu Val Ala Lys Leu Val Thr Gln Glu Met Phe
        1715                1720                1725

Gln Asn Ile Asp Lys Lys Ile Glu Ser Gln Arg Ile Met Lys Val Glu
    1730                1735                1740
```

-continued

```
Phe Thr Gln Cys Ser Met Asn Val Val Ser Lys Thr Leu Phe Arg Lys
1745                1750                1755                1760

Ser Pro Ile His His Ile Asp Lys Thr Met Ile Asn Phe Pro Ala
            1765                1770                1775

Ala Met Pro Phe Ser Lys Ala Glu Ile Asp Pro Met Ala Met Met Leu
        1780                1785                1790

Ser Lys Tyr Ser Leu Pro Ile Val Glu Glu Pro Glu Asp Tyr Lys Glu
    1795                1800                1805

Ala Ser Val Phe Tyr Gln Asn Lys Ile Val Gly Lys Thr Gln Leu Val
1810                1815                1820

Asp Asp Phe Leu Asp Leu Asp Met Ala Ile Thr Gly Ala Pro Gly Ile
1825                1830                1835                1840

Asp Ala Ile Asn Met Asp Ser Ser Pro Gly Phe Pro Tyr Val Gln Glu
            1845                1850                1855

Lys Leu Thr Lys Arg Asp Leu Ile Trp Leu Asp Glu Asn Gly Leu Leu
        1860                1865                1870

Leu Gly Val His Pro Arg Leu Ala Gln Arg Ile Leu Phe Asn Thr Val
    1875                1880                1885

Met Met Glu Asn Cys Ser Asp Leu Asp Val Val Phe Thr Thr Cys Pro
1890                1895                1900

Lys Asp Glu Leu Arg Pro Leu Glu Lys Val Leu Glu Ser Lys Thr Arg
1905                1910                1915                1920

Ala Ile Asp Ala Cys Pro Leu Asp Tyr Thr Ile Leu Cys Arg Met Tyr
            1925                1930                1935

Trp Gly Pro Ala Ile Ser Tyr Phe His Leu Asn Pro Gly Phe His Thr
        1940                1945                1950

Gly Val Ala Ile Gly Ile Asp Pro Asp Arg Gln Trp Asp Glu Leu Phe
    1955                1960                1965

Lys Thr Met Ile Arg Phe Gly Asp Val Gly Leu Asp Leu Asp Phe Ser
1970                1975                1980

Ala Phe Asp Ala Ser Leu Ser Pro Phe Met Ile Arg Glu Ala Gly Arg
1985                1990                1995                2000

Ile Met Ser Glu Leu Ser Gly Thr Pro Ser His Phe Gly Thr Ala Leu
            2005                2010                2015

Ile Asn Thr Ile Ile Tyr Ser Lys His Leu Leu Tyr Asn Cys Cys Tyr
        2020                2025                2030

His Val Cys Gly Ser Met Pro Ser Gly Ser Pro Cys Thr Ala Leu Leu
    2035                2040                2045

Asn Ser Ile Ile Asn Asn Ile Asn Leu Tyr Tyr Val Phe Ser Lys Ile
2050                2055                2060

Phe Gly Lys Ser Pro Val Phe Phe Cys Gln Ala Leu Arg Ile Leu Cys
2065                2070                2075                2080

Tyr Gly Asp Asp Val Leu Ile Val Phe Ser Arg Asp Val Gln Ile Asp
            2085                2090                2095

Asn Leu Asp Leu Ile Gly Gln Lys Ile Val Asp Glu Phe Lys Lys Leu
        2100                2105                2110

Gly Met Thr Ala Thr Ser Ala Asp Lys Asn Val Pro Gln Leu Lys Pro
    2115                2120                2125

Val Ser Glu Leu Thr Phe Leu Lys Arg Ser Phe Asn Leu Val Glu Asp
2130                2135                2140

Arg Ile Arg Pro Ala Ile Ser Glu Lys Thr Ile Trp Ser Leu Met Ala
2145                2150                2155                2160

Trp Gln Arg Ser Asn Ala Glu Phe Glu Gln Asn Leu Glu Asn Ala Gln
```

|  | 2165 |  | 2170 |  | 2175 |  |
|---|---|---|---|---|---|---|

Trp Phe Ala Phe Met His Gly Tyr Glu Phe Tyr Gln Lys Phe Tyr Tyr
         2180                2185                 2190

Phe Val Gln Ser Cys Leu Glu Lys Glu Met Ile Glu Tyr Arg Leu Lys
         2195                2200                 2205

Ser Tyr Asp Trp Trp Arg Met Arg Phe Tyr Asp Gln Cys Phe Ile Cys
         2210                2215                 2220

Asp Leu Ser
2225

<210> SEQ ID NO 13
<211> LENGTH: 9416
<212> TYPE: DNA
<213> ORGANISM: Artificial Sequence
<220> FEATURE:
<223> OTHER INFORMATION: Hepatitis C virus sequence

<400> SEQUENCE: 13

```
gccagccccc tgatgggggc gacactccac catgaatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcacgtcg gcccgaggc aggacctggg ctcagcccgg gtaccttgg ccctctatg     600
gcaatgaggg ttgcgggtgg gcgggatggc tcctgtctcc ccgtggctct cggcctagct     660
ggggccccac agaccccgg cgtaggtcgc gcaatttggg taaggtcatc gataccctta     720
cgtgcggctt cgccgacctc atgggtaca taccgctcgt cggcgcccct cttggaggcg     780
ctgccagggc cctggcgcat ggcgtccggg ttctggaaga cggcgtgaac tatgcaacag     840
ggaaccttcc tggttgctct ttctctatct tccttctggc cctgctctct tgcctgactg     900
tgcccgcttc agcctaccaa gtgcgcaatt cctcggggct ttaccatgtc accaatgatt     960
gccctaactc gagtgttgtg tacgaggcgg ccgatgccat cctgcacact ccggggtgtg    1020
tcccttgcgt tcgcgagggt aacgcctcga ggtgttgggt ggcggtgacc ccacggtgg    1080
ccaccaggga cggcaaactc cccacaacgc agcttcgacg tcatatcgat ctgcttgtcg    1140
ggagcgccac cctctgctcg gccctctacg tggggacct gtgcgggtct gtctttcttg    1200
ttggtcaact gtttaccttc tctcccaggc accactggac gacgcaagac tgcaattgtt    1260
ctatctatcc cggccatata acgggtcatc gcatggcatg gaatatgatg atgaactggt    1320
cccctacggc agcgttggtg gtagctcagc tgctccgaat cccacaagcc atcatggaca    1380
tgatcgctgg cgcccactgg ggagtcctgg cgggcataaa gtatttctcc atggtgggga    1440
actgggcgaa ggtcctggta gtgctgctgc tatttgccgg cgtcgacgcg gaaacccacg    1500
tcaccggggg aaatgccggc cgcaccacgg ctgggcttgt tggtctcctt acaccaggcg    1560
ccaagcagaa catccaactg atcaacacca cggcagttg gcacatcaat gcacggcct    1620
tgaactgcaa tgaaagcctt aacaccggct ggttagcagg gctcttctat cagcacaaat    1680
```

-continued

```
tcaactcttc aggctgtcct gagaggttgg ccagctgccg acgccttacc gattttgccc      1740
agggctgggg tcctatcagt tatgccaacg gaagcggcct cgacgaacgc ccctactgct      1800
ggcactaccc tccaagacct tgtggcattg tgcccgcaaa gagcgtgtgt ggcccggtat      1860
attgcttcac tcccagcccc gtggtggtgg gaacgaccga caggtcgggc gcgcctacct      1920
acagctgggt gcaaatgat acggatgtct cgtccttaa caacaccagg ccaccgctgg        1980
gcaattggtt cggttgtacc tggatgaact caactggatt caccaaagtg tgcggagcgc      2040 cccttgtgt catcggaggg gtgggcaaca acaccttgct ctgccccact gattgcttcc       2100
gcaaatatcc ggaagccaca tactctcggt gcggctccgg tcccaggatt acacccaggt     2160
gcatggtcga ctacccgtat aggctttggc actatccttg taccatcaat tacaccatat      2220
tcaaagtcag gatgtacgtg ggaggggtcg agcacaggct ggaagcggcc tgcaactgga     2280
cgcggggcga acgctgtgat ctggaagaca gggacaggtc cgagctcagc ccgttgctgc     2340
tgtccaccac acagtggcag gtccttccgt gttctttcac gaccctgcca gccttgtcca     2400
ccggcctcat ccacctccac cagaacattg tggacgtgca gtacttgtac ggggtagggt    2460
caagcatcgc gtcctgggcc attaagtggg agtacgtcgt tctcctgttc cttctgcttg      2520
cagacgcgcg cgtctgttcc tgcttgtgga tgatgttact catatcccaa gcggaggcgg     2580
ctttggagaa cctcgtaata tcaatgcag catccctggc cgggacgcat ggtcttgtgt      2640
ccttcctcgt gttcttctgc tttgcgtggt atctgaaggg taggtgggtg cccggagcgg     2700
tctacgccct ctacgggatg tggcctctcc tcctgctcct gctggcgttg cctcagcggg     2760
catacgcact ggacacggag gtggccgcgt cgtgtggcgg cgttgttctt gtcgggttaa    2820
tggcgctgac tctgtcgcca tattacaagc gctatatcag ctggtgcatg tggtggcttc    2880
agtattttct gaccagagta gaagcgcaac tgcacgtgtg ggttcccccc ctcaacgtcc    2940
ggggggggcg cgatgccgtc atcttactca cgtgtgtagt acacccggcc ctggtatttg    3000
acatcaccaa actactcctg gccatcttcg gacccctttg gattcttcaa gccagtttgc    3060
ttaaagtccc ctacttcgtg cgcgttcaag gccttctccg gatctgcgcg ctagcgcgga    3120
agatagccgg aggtcattac gtgcaaatgg ccatcatcaa gttaggggcg cttactggca    3180
cctgtgtgta taaccatctc gctcctcttc gagactgggc gcacaacggc ctgcgagatc    3240
tggccgtggc tgtggaacca gtcgtcttct cccgaatgga gaccaagctc atcacgtggg    3300
gggcagatac cgccgcgtgc ggtgacatca tcaacggctt gccgtctct gcccgtaggg    3360 gccaggagat actgcttggg ccagccgacg gaatggtctc caagggtgg aggttgctgg     3420 cgcccatcac ggcgtacgcc cagcagacga gaggcctcct agggtgtata atcaccagcc    3480
tgactggccg ggacaaaaac caagtggagg gtgaggtcca gatcgtgtca actgctaccc    3540
agaccttcct ggcaacgtgc atcaatgggg tatgctggac tgtctaccac ggggccggaa    3600
cgaggaccat cgcatcaccc aagggtcctg tcatccagac gtataccaat gtggatcaag    3660
acctcgtggg ctggccccgct cctcaaggtt cccgctcatt gacaccctgc acctgcggct    3720
cctcggacct ttacctggtc acgaggcacg ccgatgtcat tccgtgcgc cggcgaggtg    3780 atagcagggg tagcctgctt tcgccccggc ccatttccta cttgaaaggc ctcctcgggg    3840
gtccgctgtt gtgcccacg ggacacgccg tgggcctatt cagggccgcg gtgtgcaccc     3900
gtggagtggc taaggcggtg gactttatcc ctgtggagaa cctagagaca accatgagat    3960
ccccggtgtt cacggacaac tcctctccac cagcagtgcc ccagagcttc caggtggccc    4020
```

```
acctgcatgc tcccaccggc agcggtaaga gcaccaaggt cccggctgcg tacgcagcca  4080
agggctacaa ggtgttggtg ctcaacccct ctgttgctgc aacactgggc tttggtgctt  4140
acatgtccaa ggcccatggg gttgatccta atatcaggac cggggtgaga acaattacca  4200
ctggcagccc catcacgtac tccacctacg gcaagttcct tgccgacgcc gggtgctcag  4260
gaggtgctta tgacataata atttgtgacg agtgccactc cacggatgcc acatccatct  4320
cgggcatcgg cactgtcctt gaccaagcag agactgcggg ggcgagactg gttgtgctcg  4380
ccactgctac ccctccggc tccgtcactg tgtcccatcc taacatcgag gaggttgctc  4440
tgtccaccac cggagagatc ccttttacg gcaaggctat ccccctcgag gtgatcaagg  4500
ggggaagaca tctcatcttc tgccactcaa agaagaagtg cgacgagctc gccgcgaagc  4560
tggtcgcatt gggcatcaat gccgtggcct actaccgcgg tcttgacgtg tctgtcatcc  4620
cgaccagcgg cgatgttgtc gtcgtgtcga ccgatgctct catgactggc tttaccggcg  4680
acttcgactc tgtgatagac tgcaacacgt gtgtcactca gacagtcgat tttagccttg  4740
accctacctt taccattgag acaaccacgc tcccccagga tgctgtctcc aggactcaac  4800
gccggggcag gactggcagg gggaagccag gcatctatag atttgtggca ccggggggagc  4860
gccccctccgg catgttcgac tcgtccgtcc tctgtgagtg ctatgacgcg ggctgtgctt  4920
ggtatgagct cacgcccgcc gagactacag ttaggctacg agcgtacatg aacaccccgg  4980
ggcttcccgt gtgccaggac catcttggat tttgggaggg cgtctttacg ggcctcactc  5040
atatagatgc ccactttcta tcccagacaa agcagagtgg ggagaacttt ccttacctgg  5100
tagcgtacca agccaccgtg tgcgctaggg ctcaagcccc tccccatcg tgggaccaga  5160
tgcggaagtg tttgatccgc cttaaaccca ccctccatgg gccaacaccc ctgctataca  5220
gactgggcgc tgttcagaat gaagtcaccc tgacgcaccc aatcaccaaa tacatcatga  5280
catgcatgtc ggccgacctg gaggtcgtca cgagcacctg ggtgctcgtt ggcggcgtcc  5340
tggctgctct ggccgcgtat tgcctgtcaa caggctgcgt ggtcatagtg ggcaggatcg  5400
tcttgtccgg gaagccggca attataccctg acagggaggt tctctaccag gagttcgatg  5460
agatggaaga gtgctctcag cacttaccgt acatcgagca agggatgatg ctcgctgagc  5520
agttcaagca gaaggccctc ggcctcctgc agaccgcgtc cgccatgca gaggttatca  5580
cccctgctgt ccagaccaac tggcagaaac tcgaggtctt tgggcgaag cacatgtgga  5640
atttcatcag tgggatacaa tacttggcg gcctgtcaac gctgcctggt aaccccgcca  5700
ttgcttcatt gatggctttt acagctgccg tcaccagccc actaaccact ggccaaaccc  5760
tcctcttcaa catattgggg gggtgggtgg ctgcccagct cgccgccccc ggtgccgcta  5820
ccgcctttgt gggcgctggc ttagctggcg ccgcactcga cagcgttgga ctggggaagg  5880
tcctcgtgga cattcttgca ggctatggcg cgggcgtggc gggagctctt gtggcattca  5940
agatcatgag cggtgaggtc ccctccacgg aggacctggt caatctgctg cccgccatcc  6000
tctcacctgg agcccttgca gtcggtgtgg tctttgcatc aatactgcgc cggcgtgttg  6060
gcccgggcga gggggcagtg caatggatga accggctaat agccttcgcc tcccggggga  6120
accatgtttc ccccacacac tacgtgccgg agagcgatgc agccgcccgc gtcactgcca  6180
tactcagcag cctcactgta acccagctcc tgaggcgact gcatcagtgg ataagctcgg  6240
agtgtaccac tccatgctcc ggttcctggc taagggacat ctgggactgg atatgcgagg  6300
tgctgagcga ctttaagacc tggctgaaag ccaagctcat gccacaactg cctgggattc  6360
cctttgtgtc ctgccagcgc gggtataggg gggtctggcg aggagacggc attatgcaca  6420
```

-continued

```
ctcgctgcca ctgtggagct gagatcactg gacatgtcaa aaacgggacg atgaggatcg      6480
tcggtcctag gacctgcaag aacatgtgga gtgggacgtt cttcattaat gcctacacca      6540
cgggcccctg tactcccctt cctgcgccga actataagtt cgcgctgtgg agggtgtctg      6600
cagaggaata cgtggagata aggcgggtgg gggacttcca ctacgtatcg ggcatgacta      6660
ctgacaatct caaatgcccg tgccagatcc catcgcccga atttttcaca gaattggacg      6720
gggtgcgcct acataggttt gcgccccctt gcaagcccct gctgcgggag gaggtatcat      6780
tcagagtagg actccacgag tacccggtgg ggtcgcaatt accttgcgag cccgaaccgg      6840
acgtagccgt gttgacgtcc atgctcactg atccctccca tataacagca gaggcggccg      6900
ggagaaggtt ggcgagaggg tcacccccTt ctatggccag ctcctcggct agccagctgt      6960
ccgctccatc tctcaaggca acttgcaccg ccaaccatga ctccctgac gccgagctca       7020 tagaggctaa cctcctgtgg aggcaggaga tgggcggcaa catcaccagg gttgagtcag      7080
agaacaaagt ggtgattctg gactccttcg atccgcttgt ggcagaggag gatgagcggg      7140
aggtctccgt acccgcagaa attctgcgga agtctcggag attcgcccca gccctgcccg      7200
tctgggcgcg gccggactac aaccccctgc tagtagagac gtggaaaaag cctgactacg      7260
aaccacctgt ggtccatggc tgcccgctac cacctccacg gtccctcct gtgcctccgc       7320 ctcggaaaaa gcgtacggtg gtcctcaccg aatcaaccct acctactgcc ttggccgagc      7380
ttgccaccaa agttttggc agctcctcaa cttccggcat tacgggcgac aatacgacaa       7440
catcctctga gcccgcccct tctggctgcc ccccgactc cgacgttgag tcctattctt       7500
ccatgccccc cctggagggg gagcctgggg atcggatct cagcgacggg tcatggtcga       7560
cggtcagtag tggggccgac acggaagatg tcgtgtgctg ctcaatgtct tattcctgga      7620
caggcgcact cgtcaccccg tgcgctgcgg aggaacaaaa actgcccatc aacgcactga      7680
gcaactcgtt gctacgccat cacaatctgg tgtattccac cacttcacgc agtgcttgcc      7740
aaaggaagaa gaaagtcaca tttgacagac tgcaagttct ggacagccat taccaggacg      7800
tgctcaagga ggtcaaagca gcggcgtcaa aagtgaaggc taacttgcta tccgtagagg      7860
aagcttgcag cctggcgccc ccacattcag ccaaatccaa gtttggctat ggggcaaaag      7920
acgtccgttg ccatgccaga aaggccgtag cccacatcaa ctccgtgtgg aaagaccttc      7980
tggaagacag tgtaacacca atagacacta ccatcatggc caagaacgag gttttctgcg      8040
ttcagcctga aaggggggt cgtaagccag ctcgtctcat cgtgttcccc gacctgggcg       8100
tgcgcgtgtg cgagaagatg gccctgtacg acgtggttag caagctcccc ttggccgtga      8160
tgggaagctc ctacgattc caatactcac caggacagcg ggttgaattc ctcgtgcaag       8220
cgtggaagtc caagaagacc ccgatggggc tctcgtatga tacccgctgt tttgactcca      8280
cagtcactga gagcgacatc cgtacggagg aggcaattta ccaatgttgt gacctggacc      8340
cccaagcccg cgtggccatc aagtccctca ctgagaggct ttatgttggg ggccctctta      8400
ctaattcaag gggggaaaac tgcggctacc gcaggtgccg cgcgagcaga gtactgcaaa      8460
ctagctgtgg taacccctc actcgctaca tcaaggcccg gcagcctgt cgagccgcag        8520 ggctccagga ctgcaccatg ctcgtgtgtg gcgacgactt agtcgttatc tgtgaaagtg      8580
cgggggtcca ggaggacgcg gcgagcctga gagccttcac ggaggctatg accaggtact      8640
ccgccccccc cggggacccc ccacaaccag aatacgactt ggagcttata acatcatgct      8700
cctccaacgt gtcagtcgcc cacgacggcg ctggaaagag ggtctactac cttacccgtg      8760
```

| | |
|---|---|
| accctacaac ccccctcgcg agagccgcgt gggagacagc aagacacact ccagtcaatt | 8820 |
| cctggctagg aacataatc atgtttgccc ccacactgtg ggcgaggatg atactgatga | 8880 |
| cccacttctt tagcgtcctc atagccaggg atcagcttga acaggctctc aactgcgaga | 8940 |
| tctacggagc ctgctactcc atagaaccac tggatctacc tccaatcatt caaagactcc | 9000 |
| atggcctcag cgcattttca ctccacagtt actctccagg tgaaattaat agggtggccg | 9060 |
| catgcctcag aaaacttggg gtcccgccct tgcgagcttg gagacaccgg gcctggagcg | 9120 |
| tccgcgctag gcttctggcc agaggaggca aggctgccat atgtggcaag tacctcttca | 9180 |
| actgggcagt aagaacaaag ctcaaactca ctccgataac ggccgctggc cggctggact | 9240 |
| tgtccggctg gttcacggct ggctacagcg ggggagacat ttatcacagc gtgtctcatg | 9300 |
| cccggccccg ctggttctgg ttttgcctac tcctgcttgc tgcagggggta ggcatctacc | 9360 |
| tcctccccaa ccgatgaaga ttgggctaac cactccaggc caataggcca ttccct | 9416 |

<210> SEQ ID NO 14
<211> LENGTH: 3182
<212> TYPE: DNA
<213> ORGANISM: Artificial Sequence
<220> FEATURE:
<223> OTHER INFORMATION: Hepatitis B virus sequence

<400> SEQUENCE: 14

| | |
|---|---|
| aattccacaa ccttccacca aactctgcaa gatcccagag tgagaggcct gtatttccct | 60 |
| gctggtggct ccagttcagg aacagtaaac cctgttctga ctactgcctc tcccttatcg | 120 |
| tcaatcttct cgaggattgg ggaccctgcg ctgaacatgg agaacatcac atcaggattc | 180 |
| ctaggacccc ttctcgtgtt acaggcgggg ttttcttgt tgacaagaat cctcacaata | 240 |
| ccgcagagtc tagactcgtg gtggacttct ctcaattttc taggggaac taccgtgtgt | 300 |
| cttggccaaa attcgcagtc cccaacctcc aatcactcac caacctcttg tcctccaact | 360 |
| tgtcctggtt atcgctggat gtgtctgcgg cgttttatca tcttcctctt catcctgctg | 420 |
| ctatgcctca tcttcttgtt ggttcttctg gactatcaag gtatgttgcc cgtttgtcct | 480 |
| ctaattccag gatcctcaac aaccagcacg ggaccatgcc ggacctgcat gactactgct | 540 |
| caaggaacct ctatgtatcc ctcctgttgc tgtaccaaac cttcggacgg aaattgcacc | 600 |
| tgtattccca tcccatcatc ctgggctttc ggaaaattcc tatgggagtg gcctcagcc | 660 |
| cgtttctcct ggctcagttt actagtgcca tttgttcagt ggttcgtagg gctttccccc | 720 |
| actgtttggc tttcagttat atggatgatg tggtattggg ggccaagtct gtacagcatc | 780 |
| ttgagtccct ttttaccgct gttaccaatt tcttttttgtc tttgggtata catttaaacc | 840 |
| ctaacaaaac aaagagatgg ggttactctc taaatttat gggttatgtc attggatgtt | 900 |
| atgggtcctt gccacaagaa cacatcatac aaaaaatcaa agaatgtttt agaaaacttc | 960 |
| ctattaacag gcctattgat tggaaagtat gtcaacgaat tgtgggtctt ttgggttttg | 1020 |
| ctgcccctt tacacaatgt ggttatcctg cgttgatgcc tttgtatgca tgtattcaat | 1080 |
| ctaagcaggc tttcactttc tcgccaactt acaaggcctt tctgtgtaaa caatacctga | 1140 |
| acctttaccc cgttgcccgg caacggccag gtctgtgcca agtgtttgct gacgcaaccc | 1200 |
| ccactggctg gggcttggtc atgggccatc agcgcatgtg tggaaccttt tcggctcctc | 1260 |
| tgccgatcca tactgcggaa ctcctagccg cttgttttgc tcgcagcagg tctggagcaa | 1320 |
| acattatcgg gactgataac tctgttgtcc tatcccgcaa atatacatcg tttccatggc | 1380 |
| tgctaggctg tgctgccaac tggatcctgc gcgggacgtc cttttgttac gtcccgtcgg | 1440 |

-continued

```
cgctgaatcc tgcggacgac ccttctcggg gtcgcttggg actctctcgt cccttctcc      1500 gtctgccgtt ccgaccgacc acggggcgca cctctcttta cgcggactcc ccgtctgtgc      1560
cttctcatct gccggaccgt gtgcacttcg cttcacctct gcacgtcgca tggagaccac      1620
cgtgaacgcc caccaaatat tgcccaaggt cttacataag aggactcttg gactctcagc      1680
aatgtcaacg accgaccttg aggcatactt caaagactgt ttgtttaaag actgggagga      1740
gttgggggag gagattaggt taaaggtctt tgtactagga ggctgtaggc ataaattggt      1800
ctgcgcacca gcaccatgca actttttcac ctctgcctaa tcatctcttg ttcatgtcct      1860
actgttcaag cctccaagct gtgccttggg tggctttggg gcatggacat cgacccttat      1920
aaagaatttg gagctactgt ggagttactc tcgtttttgc cttctgactt ctttccttca      1980
gtacgagatc ttctagatac cgcctcagct ctgtatcggg aagccttaga gtctcctgag      2040
cattgttcac ctcaccatac tgcactcagg caagcaattc tttgctgggg ggaactaatg      2100
actctagcta cctgggtggg tgttaatttg gaagatccag cgtctagaga cctagtagtc      2160
agttatgtca acactaatat gggcctaaag ttcaggcaac tcttgtggtt tcacatttct      2220
tgtctcactt ttggaagaga aacagttata gagtatttgg tgtctttcgg agtgtggatt      2280
cgcactcctc cagcttatag accaccaaat gccccctatcc tatcaacact tccggagact      2340
actgttgtta gacgacgagg caggtcccct agaagaagaa ctccctcgcc tcgcagacga      2400
aggtctcaat cgccgcgtcg cagaagatct caatctcggg aatctcaatg ttagtattcc      2460
ttggactcat aaggtgggga actttactgg gctttattct tctactgtac ctgtctttaa      2520
tcctcattgg aaaacaccat ctttttcctaa tatacattta caccaagaca ttatcaaaaa      2580
atgtgaacag tttgtaggcc cactcacagt taatgagaaa agaagattgc aattgattat      2640
gcctgccagg ttttatccaa aggttaccaa atatttacca ttggataagg gtattaaacc      2700
ttattatcca gaacatctag ttaatcatta cttccaaact agacactatt tacacactct      2760
atggaaggcg ggtatattat ataagagaga aacaacacat agcgcctcat tttgtgggtc      2820
accatattct tgggaacaag atctacagca tggggcagaa tctttccacc agcaatcctc      2880
tgggattctt tcccgaccac cagttggatc cagccttcag agcaaacacc gcaaatccag      2940
attgggactt caatcccaac aaggacacct ggccagacgc caacaaggta ggagctggag      3000
cattcgggct gggtttcacc ccaccgcacg gaggcctttt ggggtggagc cctcaggctc      3060
agggcatact acaaactttg ccagcaaatc cgcctcctgc ctccaccaat cgccagtcag      3120
gaaggcagcc taccccgctg tctccacctt tgagaaacac tcatcctcag gccatgcagt      3180
gg                                                                    3182
```

<210> SEQ ID NO 15
<211> LENGTH: 7478
<212> TYPE: DNA
<213> ORGANISM: Artificial Sequence
<220> FEATURE:
<223> OTHER INFORMATION: Hepatitis A virus sequence

<400> SEQUENCE: 15

```
ttcaagaggg gtctccggag gtttccggag cccctcttgg aagtccatgg tgagggact       60 tgatacctca ccgccgtttg cctaggctat aggctaaatt tccctttccc tgtccctccc      120
ttatttccct tgttttgct tgtaaatatt aattcctgca ggttcagggt tctttaatct       180
gtttctctat aagaacactc aattttcacg ctttctgtct tctttcttcc agggctctcc      240
```

```
ccttgcccta ggctctggcc gttgcgcccg gcggggtcaa ctccatgatt agcatggagc    300
tgtaggagtc taaattgggg acgcagatgt ttgggacgtc accttgcagt gttaacttgg    360
ctctcatgaa cctctttgat cttccacaag gggtaggcta cgggtgaaac ctcttaggct    420
aatacttcta tgaagagatg ctttggatag ggtaacagcg gcggatattg gtgagttgtt    480
aagacaaaaa ccattcaacg ccggaggact ggctctcatc cagtggatgc attgagtgga    540
ttgattgtca gggctgtctc taggtttaat ctcagacctc tctgtgctta gggcaaacac    600
catttggcct taaatgggat cctgtgagag ggggtccctc cattgacagc tggactgttc    660 tttgggcct tatgtggtgt ttgcctctga ggtactcagg ggcatttagg tttttcctca    720
ttcttaaaca ataatgaata tgtccaaaca aggaattttc cagactgttg ggagtggcct    780
tgaccacatc ctgtctttgg cagatattga ggaagagcaa atgattcagt ccgttgatag    840
gactgcagtg actggagctt cttacttcac ttctgtggac caatcttcag ttcatactgc    900
tgaggttggc tcacatcaaa ttgaacctt gaaaacctct gttgataaac ctggttctaa    960
gaaaactcag ggggaaaagt ttttcctgat tcattctgct gattggctca ctacacatgc    1020
tctctttcat gaagttgcaa aattggatgt ggtgaaacta ctgtataatg agcagtttgc    1080
cgtccaaggt ttgttgagat accatacata tgcaagattt ggcattgaga ttcaagttca    1140
gataaatccc acacccttc agcaaggagg actaatttgt gccatggttc ctggtgacca    1200
aagttatggt tcaatagcat ccttgactgt ttatcctcat ggtctgttaa attgcaatat    1260
caacaatgta gttagaataa aggttccatt tatttatact agaggtgctt atcattttaa    1320
agatccacag tacccagttt gggaattgac aatcagagtt tggtcagagt tgaatattgg    1380
aacaggaact tcagcttaca cttcactcaa tgttttagct aggtttacag atttggagtt    1440
gcatggatta actcctcttt ctacacagat gatgagaaat gaatttaggg tcagtactac    1500
tgaaaatgtt gtaaatttgt caaattatga agatgcaagg gcaaaaatgt cttttgcttt    1560
ggatcaggaa gattggaagt ctgatccttc ccaaggtggt ggaattaaaa ttactcattt    1620
tactacctgg acatccattc caaccttagc tgctcagttt ccatttaatg cttcagattc    1680
agttggacaa caaattaaag ttattccagt ggacccatac tttttccaaa tgacaaacac    1740
taatcctgat caaaaatgta taactgcctt ggcctctatt tgtcagatgt tctgcttttg    1800 gagggggagat cttgttttg attttcaggt ttttccaacc aaatatcatt caggtagact    1860
gttgttttgt tttgttcctg ggaatgagtt aatagatgtt actggaatta cattaaaaca    1920
ggcaactact gctccttgtg cagtgatgga cattacagga gtgcagtcaa ccttgagatt    1980
tcgtgttcct tggatttctg atacaccta tcgagtgaat aggtacacga agtcagcaca    2040
tcaaaaaggt gagtacactg ccattgggaa gcttattgtg tattgttata acagactgac    2100
ttctccttct aatgttgcct ctcatgttag agtaatgtt tatctttcag caattaattt    2160
ggaatgtttt gctcctcttt accatgctat ggatgttact acacaggttg agatgattc    2220 aggaggtttc tcaacaacag tttctacaga gcagaatgtt cctgatcccc aagttgggat    2280
aacaaccatg agggatttaa aaggaaaagc caataggggga aagatggatg tttcaggagt    2340
gcaagcacct cgtgggagct atcagcaaca attgaacgat ccagttttag caaagaaagt    2400
acctgagaca tttcctgaat tgaagcctgg agagtccaga catacatcag atcacatgtc    2460
tatttataaa ttcatgggaa ggtctcattt tttgtgcact tttactttca attcaaataa    2520
taaagagtac acatttccaa taaccctgtc ttcgacttct aatcctcctc atggtttacc    2580
atcaacatta aggtggttct tcaatttgtt tcagttgtat agaggaccat tggatttaac    2640
```

-continued

```
aattataatc acaggagcca ctgatgtgga tggtatggcc tggtttactc cagtgggcct    2700
tgctgtcgac ccttgggtgg aaaaggagtc agctttgtct attgattata aaactgccct    2760
tggagctgtt agatttaata caagaagaac aggaaacatt caaattagat tgccgtggta    2820
ttcttatttg tatgccgtgt ctggagcact ggatggcttg ggggataaga cagattctac    2880
atttggattg tttctattcg agattgcaaa ttacaatcat tctgatgaat atttgtcctt    2940
cagttgttat ttgtctgtca cagagcaatc agagttctat tttcctagag ctccattaaa    3000
ttcaaatgct atgttgtcca ctgaatccat gatgagtaga attgcagctg gagacttgga    3060
gtcatcagtg gatgatccca gatcagagga ggatagaaga tttgagagtc atatagaatg    3120
taggaaacca tacaaagaat tgagactgga ggttgggaaa caagactca aatatgctca     3180 ggaagagtta tcaaatgaag tgcttccacc tcctaggaaa atgaagggt tattttcaca     3240 agctaaaatt tctcttttt atactgagga gcatgaaata atgaagtttt cttggagagg     3300
agtgactgct gatactaggg ctttgagaag atttggattc tctctggctg ctggtagaag    3360
tgtgtggact cttgaaatgg atgctggagt tcttactgga agattgatca gattgaatga    3420
tgagaaatgg acagaaatga aggatgataa gattgtttca ttaattgaaa agttcacaag    3480
caataaatat tggtctaaag tgaattttcc acatggaatg ttggatcttg aagaaattgc    3540
tgccaattct aaggattttc caaatatgtc tgagacagat ttgtgtttcc tgttacattg    3600
gctaaatcca aagaaaatca atttagcaga tagaatgctt ggattgtctg gagtgcagga    3660
aattaaggaa cagggtgttg gactgatagc agagtgtaga actttcttgg attctattgc    3720
tgggactttg aaatctatga tgtttgggtt tcatcattct gtgactgttg aaattataaa    3780
tactgtgctt tgttttgtta agagtggaat cctgctttat gtcatacaac aattgaacca    3840
agatgaacac tctcacataa ttggtttgtt gagagttatg aattatgcag atattggctg    3900
ttcagttatt tcatgtggta agttttttc caaaatgtta gaaacagttt ttaattggca    3960
aatggattct agaatgatgg agctgaggac tcagagcttc tctaattggt taagagatat    4020
ttgttcagga attactattt ttaaaagttt taaggatgcc atatattggt tatatacaaa    4080
attgaaggat ttttatgaag taaattatgg caagaaaaag gatattctta atattctcaa    4140
agataatcag caaaaaatag aaaaagccat tgaagaagca gacaatttttt gcattttgca    4200 aattcaagat gtagagaaat ttgatcagta tcagaaaggg gttgatttaa tacaaaagct    4260
gagaactgtc cattcaatgg cgcaagttga ccccaatttg ggggttcatt tgtcacctct    4320
cagagattgc atagcaagag tccaccaaaa gctcaagaat cttggatcta taaatcaggc    4380
catggtaaca agatgtgagc cagttgtttg ctatttgtat ggcaaaagag ggggagggaa    4440
aagcttgact tcaattgcat tggcaaccaa aatttgtaaa cactatggtg ttgaacctga    4500 gaaaatatt tacaccaaac ctgtggcctc agattattgg gatggatata gtggacaatt    4560
agtttgcatt attgatgata ttggccaaaa cacaacagat gaagattggt cagatttttg    4620
tcaattagtg tcaggatgcc caatgagatt gaatatggct tctctagagg agaagggcag    4680
acatttttcc tctccttta taatagcaac ttcaaattgg tcaaatccaa gtccaaaaac    4740
agtttatgtt aaggaagcaa ttgatcgtag gcttcatttt aaggttgaag ttaaacctgc    4800
ttcatttttt aaaaatcctc acaatgatat gttgaatgtt aatttggcca aaacaaatga    4860
tgcaattaag gacatgtctt gtgttgattt aataatggat ggacacaata tttcattgat    4920
ggatttactt agttccttag tgatgacagt tgaaattagg aaacagaata tgagtgaatt    4980
```

```
catggagttg tggtctcagg gaatttcaga tgatgacaat gatagtgcag tggctgagtt       5040
tttccagtct tttccatctg gtgaaccatc aaattggaag ttatctagtt ttttccaatc       5100
tgtcactaat cacaagtggg ttgctgtggg agctgcagtt ggcattcttg gagtgcttgt       5160
gggaggatgg tttgtgtata agcattttc cgcaaagag gaagaaccaa ttccagctga        5220
aggggtttat catggcgtga ctaagcccaa acaagtgatt aaattggatg cagatccagt       5280
agagtcccag tcaactctag aaatagcagg attagttagg aaaaatctgg ttcagtttgg       5340
agttggtgag aaaaatggat gtgtgagatg ggtcatgaat gccttaggag tgaaggatga       5400
ttggttgtta gtaccttctc atgcttataa atttgaaaag gattatgaaa tgatggagtt       5460
ttacttcaat agaggtggaa cttactattc aatttcagct ggtaatgttg ttattcaatc       5520
tttagatgtg ggatttcaag atgttgtttt aatgaaggtt cctacaattc ccaagtttag       5580
agatattact caacactttta ttaagaaagg agatgtgcct agagccttaa atcgcttggc       5640
aacattagtg acaaccgtta atggaactcc tatgttaatt tctgagggac cattaaagat       5700
ggaagaaaaa gccacttatg ttcataagaa gaatgatggt actacagttg atttgactgt       5760
agatcaggca tggagaggaa aaggtgaagg tcttcctgga atgtgtggtg gggccctagt       5820
gtcatcaaat cagtccatac agaatgcaat tttgggtatt catgttgctg gaggaaattc       5880
aattcttgtg gcaaagctgg ttactcaaga aatgttccaa acattgata gaaaattga        5940 aagtcagaga ataatgaaag tggaattac tcaatgttca atgaatgtag tctccaaaac       6000 gcttttaga aagagtccca ttcatcacca cattgataaa accatgatta attttcctgc       6060
agctatgcct ttctctaaag ctgaaattga tccaatggct atgatgttgt ccaaatattc       6120
attacctatt gtggaggaac cagaggatta caaggaagct tcagttttttt atcaaaacaa       6180 aatagtaggc aagactcagc tagttgatga cttttttagat cttgatatgg ctattacagg       6240
ggctccaggc attgatgcta tcaatatgga ttcatctcct gggttttcctt atgttcaaga       6300 aaaattgacc aaaagagatt taatttggtt ggatgaaaat ggtttgctgt taggagttca       6360
cccaagattg gcccagagaa ttttatttaa tactgtcatg atggaaaatt gttctgactt       6420
agatgttgtt tttacaactt gtccaaaaga tgaattgaga ccattagaga aagttttgga       6480
atcaaaaaca agagccattg atgcttgtcc tttggattat acaattctat gtcgaatgta       6540
ttggggtcca gctatcagtt atttccattt gaatccaggg tttcacacag gtgttgctat       6600
tggcatagat cctgatagac agtgggatga attatttaaa acaatgataa gatttggaga       6660
tgttggtctt gatttagatt tctctgcttt tgatgccagt cttagtccat ttatgattag       6720
ggaagcaggt agaatcatga gtgaattatc tggaacacca tctcatttttg gaacagctct       6780 tatcaatact atcatttatt ctaaacatct gctgtacaac tgttgttatc atgtttgtgg       6840
ttcaatgcct tctgggtctc cttgcacagc tttgttgaat tcaattatta ataatattaa       6900
tctgtattat gtgttttcta aaatatttgg aaagtctcca gttttctttt gtcaagcttt       6960
gaggatcctt tgttacggag atgatgtttt gatagttttt tccagagatg ttcaaattga       7020
caatcttgac ttgattggac agaaaattgt agatgagttc aaaaaacttg gcatgacagc       7080
cacctcagct gataaaaatg tgcctcaact gaagccagtt tcagaattga cttttctcaa       7140
aagatctttc aatttggtgg aggatagaat tagacctgca atttcagaaa agacaatttg       7200
gtctttgatg gcttggcaga gaagtaacgc tgagtttgag cagaatttag aaaatgctca       7260
gtggtttgct tttatgcatg gctatgagtt ctatcagaaa ttttattatt ttgttcagtc       7320
ctgtttggag aaagagatga tagaatatag acttaaatct tatgattggt ggagaatgag       7380
```

-continued

| | |
|---|---|
| attttatgac cagtgtttca tttgtgacct ttcatgattt gtttaaacaa attttcttac | 7440 |
| tctttctgag gtttgtttat ttcttttgtc cgctaact | 7478 |

<210> SEQ ID NO 16
<211> LENGTH: 2061
<212> TYPE: DNA
<213> ORGANISM: Artificial Sequence
<220> FEATURE:
<223> OTHER INFORMATION: Hepatitis C virus NS3/4A coding region

<400> SEQUENCE: 16

| | |
|---|---|
| atggcgccta tcacggccta tgcccagcag acaaggggcc ttttgggatg cataatcacc | 60 |
| agcttgaccg gccgggacaa aaaccaggtg gagggtgagg ttcagatcgt gtcaactgct | 120 |
| gcccagactt tcttggcaac ctgcattaac ggggtgtgtt ggactgtcta ccatggagcc | 180 |
| ggaacaagga ccattgcgtc acctaagggt cctgttatcc agatgtacac caatgtggac | 240 |
| caagacctcg taggctggcc cgctccccaa gtgcccgct cattaacacc atgcacttgc | 300 |
| ggctcctcgg acctttacct ggtcacgagg cacgccgatg tcattcctgt cgccgacgg | 360 |
| ggtgatggca ggggcagcct gctttcgccc cggcctatct cttacttgaa aggctcctcg | 420 |
| ggaggccctc tgctgtgccc cgcaggacat gccgtaggca tattcagagc gcggtatgc | 480 |
| acccgtggag tggctaaggc ggtggacttc atccccgtag agagcttaga caaccatg | 540 |
| aggtccccgg tgttctcaga caactcctcc ccaccagcag tgccccagag ctaccaagtg | 600 |
| gcccacctgc atgctcccac cggcagcggt aagagcacca aggtcccggc cgcatacgca | 660 |
| gctcagggct acaaggtgct ggtgctcaac ccctccgttg ctgcaacaat gggctttggt | 720 |
| gcttacatgt ccaaggccca tgggattgat cctaacatca ggactggggt gaggacaatt | 780 |
| actactggca gcccgatcac gtattccacc tacggcaagt tccttgccga cggcgggtgt | 840 |
| tcagggggtg cttatgacat aataatttgt gacgagtgcc actccacgga tgcaacatcc | 900 |
| atcttgggca ttggcactgt ccttgaccaa gcagagaccg cggggcgag actgactgtg | 960 |
| ctcgccaccg ctacccctcc gggctccgtc actgtgcccc atcctaacat cgaggaggtt | 1020 |
| gctctgtcca ctaccggaga gatccccttt tatggcaagg ctattcccct tgaagcaatt | 1080 |
| aagggggga gacatctcat cttctgccac tcaaagaaga gtgcgacga gctcgccgca | 1140 |
| aaactggtcg cgttgggcgt caatgccgtg gcttactacc gcggccttga tgtgtccgtc | 1200 |
| atcccgacca gtggtgacgt tgtcgtcgtg gcaactgacg ccctcatgac cggctttacc | 1260 |
| ggcgacttcg attcggtgat agactgcaac acgtgtgtca cccagacagt cgacttcagc | 1320 |
| cttgacccta ccttcaccat tgagacaatc acgcttcccc aggatgctgt ctcccgtact | 1380 |
| caacgtcggg gtaggactgg cagagggaag ccaggcatct acagatttgt ggcaccgggg | 1440 |
| gagcgtccctt ctggcatgtt tgactcgtct gtcctctgcg agtgctatga cgcgggttgt | 1500 |
| gcttggtatg agcttacgcc cgccgagacc acagttaggc tacgagcata catgaacacc | 1560 |
| ccggacttc ccgtgtgcca agaccatctt gaattttggg agggcgtctt acgggtctc | 1620 |
| acccacatag acgcccactt cctatcccag acaaagcaga gtgggaaaa ccttccctat | 1680 |
| ctggtagcgt accaagccac cgtgtgcgct agagctcaag cccctccccc gtcgtgggac | 1740 |
| cagatgtgga agtgcttgat ccgtctcaag cccaccctcc atgggccaac acctctgcta | 1800 |
| tatagactgg gcgctgtcca gaatgaagtc accctgacgc acccagtcac caagtatatc | 1860 |
| atgacatgta tgtcggctga cctggaggtc gtcacgagta cctgggtgct cgttggcggc | 1920 |

-continued

```
gttctggctg ctttggccgc gtattgccta tccacaggct gcgtggtcat agtaggtagg    1980
attgtcttgt ccggaaagcc ggcaatcata cccgacaggg aagtcctcta ccgggagttc    2040
gatgaaatgg aagagtgctg a                                              2061
```

<210> SEQ ID NO 17
<211> LENGTH: 686
<212> TYPE: PRT
<213> ORGANISM: Artificial Sequence
<220> FEATURE:
<223> OTHER INFORMATION: Hepatitis C virus NS3/4A peptide

<400> SEQUENCE: 17

```
Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
                 20                  25                  30

Glu Val Gln Ile Val Ser Thr Ala Ala Gln Thr Phe Leu Ala Thr Cys
             35                  40                  45

Ile Asn Gly Val Cys Trp Thr Val Tyr His Gly Ala Gly Thr Arg Thr
         50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335
```

```
Ile Glu Glu Val Ala Leu Ser Thr Thr Gly Glu Ile Pro Phe Tyr Gly
                340                 345                 350

Lys Ala Ile Pro Leu Glu Ala Ile Lys Gly Gly Arg His Leu Ile Phe
            355                 360                 365

Cys His Ser Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
            515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
    595                 600                 605

Glu Val Thr Leu Thr His Pro Val Thr Lys Tyr Ile Met Thr Cys Met
610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
    675                 680                 685
```

<210> SEQ ID NO 18
<211> LENGTH: 30
<212> TYPE: DNA
<213> ORGANISM: Artificial Sequence
<220> FEATURE:
<223> OTHER INFORMATION: cloning oligonucleotide

<400> SEQUENCE: 18
ccgtctagat cagcactctt ccatttcatc                                30

```
<210> SEQ ID NO 19
<211> LENGTH: 30
<212> TYPE: DNA
<213> ORGANISM: Artificial Sequence
<220> FEATURE:
<223> OTHER INFORMATION: cloning oligonucleotide

<400> SEQUENCE: 19
cctgaattca tggcgcctat cacggcctat                                    30

<210> SEQ ID NO 20
<211> LENGTH: 24
<212> TYPE: DNA
<213> ORGANISM: Artificial Sequence
<220> FEATURE:
<223> OTHER INFORMATION: cloning oligonucleotide

<400> SEQUENCE: 20
ccacgcggcc gcgacgacct acag                                          24

<210> SEQ ID NO 21
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 21
ctggaggtcg tcacgcctac ctgggtgctc gtt                                33

<210> SEQ ID NO 22
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 22
accgagcacc caggtaggcg tgacgacctc cag                                33

<210> SEQ ID NO 23
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 23
ctggaggtcg tccgcggtac ctgggtgctc gtt                                33

<210> SEQ ID NO 24
<211> LENGTH: 33
<212> TYPE: DNA
<213> ORGANISM: Artificial Sequence
<220> FEATURE:
<223> OTHER INFORMATION: cloning oligonucleotide

<400> SEQUENCE: 24
accgagcacc caggtaccgc ggacgacctc cag                                33

<210> SEQ ID NO 25
<211> LENGTH: 25
<212> TYPE: PRT
<213> ORGANISM: Artificial Sequence
<220> FEATURE:
<223> OTHER INFORMATION: Hepatitis C virus NS3/4A peptide
```

-continued

```
<400> SEQUENCE: 25

Thr Lys Tyr Met Thr Cys Met Ser Ala Asp Leu Glu Val Val Thr Ser
1               5                   10                  15

Thr Trp Val Leu Val Gly Gly Val Leu
            20                  25

<210> SEQ ID NO 26
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 26

Thr Lys Tyr Met Thr Cys Met Ser Ala Asp Leu Glu Val Val Thr Gly
1               5                   10                  15

Thr Trp Val Leu Val Gly Gly Val Leu
            20                  25

<210> SEQ ID NO 27
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 27

Thr Lys Tyr Met Thr Cys Met Ser Ala Asp Leu Glu Val Val Arg Gly
1               5                   10                  15

Thr Trp Val Leu Val Gly Gly Val Leu
            20                  25

<210> SEQ ID NO 28
<211> LENGTH: 12
<212> TYPE: PRT
<213> ORGANISM: Artificial Sequence
<220> FEATURE:
<223> OTHER INFORMATION: Hepatitis C virus NS3/4A peptide

<400> SEQUENCE: 28

Ser Ala Asp Leu Glu Val Val Thr Ser Thr Trp Val
1               5                   10

<210> SEQ ID NO 29
<211> LENGTH: 632
<212> TYPE: PRT
<213> ORGANISM: Artificial Sequence
<220> FEATURE:
<223> OTHER INFORMATION: Hepatitis C virus NS3 peptide

<400> SEQUENCE: 29

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
```

-continued

```
                85                  90                  95
Pro Cys Thr Cys Gly Ser Ser Asp Leu Tyr Leu Val Thr Arg His Ala
            100                 105                 110
Asp Val Ile Pro Val Arg Arg Arg Gly Asp Gly Arg Gly Ser Leu Leu
            115                 120                 125
Ser Pro Arg Pro Ile Ser Tyr Leu Lys Gly Ser Ser Gly Gly Pro Leu
            130                 135                 140
Leu Cys Pro Ala Gly His Ala Val Gly Ile Phe Arg Ala Ala Val Cys
145                 150                 155                 160
Thr Arg Gly Val Ala Lys Ala Val Asp Phe Ile Pro Val Glu Ser Leu
                165                 170                 175
Glu Thr Thr Met Arg Ser Pro Val Phe Ser Asp Asn Ser Ser Pro Pro
            180                 185                 190
Ala Val Pro Gln Ser Tyr Gln Val Ala His Leu His Ala Pro Thr Gly
            195                 200                 205
Ser Gly Lys Ser Thr Lys Val Pro Ala Ala Tyr Ala Ala Gln Gly Tyr
            210                 215                 220
Lys Val Leu Val Leu Asn Pro Ser Val Ala Ala Thr Met Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
                260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ala Thr Ser Ile Leu Gly Ile
            290                 295                 300
Gly Thr Val Leu Asp Gln Ala Glu Thr Ala Gly Ala Arg Leu Thr Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Glu Ile Pro Phe Tyr Gly
            340                 345                 350
Lys Ala Ile Pro Leu Glu Ala Ile Lys Gly Gly Arg His Leu Ile Phe
            355                 360                 365
Cys His Ser Lys Lys Cys Asp Glu Leu Ala Ala Lys Leu Val Ala
            370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
            450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
                500                 505                 510
```

```
Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr
625                 630

<210> SEQ ID NO 30
<211> LENGTH: 54
<212> TYPE: PRT
<213> ORGANISM: Artificial Sequence
<220> FEATURE:
<223> OTHER INFORMATION: Hepatitis C virus NS4A peptide

<400> SEQUENCE: 30

Ser Thr Trp Val Leu Val Gly Gly Val Leu Ala Ala Leu Ala Ala Tyr
1               5                   10                  15

Cys Leu Ser Thr Gly Cys Val Val Ile Val Gly Arg Ile Val Leu Ser
                20                  25                  30

Gly Lys Pro Ala Ile Ile Pro Asp Arg Glu Val Leu Tyr Arg Glu Phe
            35                  40                  45

Asp Glu Met Glu Glu Cys
        50

<210> SEQ ID NO 31
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 31

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
        50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
```

-continued

```
            115                 120                 125
Ser Pro Arg Pro Ile Ser Tyr Leu Lys Gly Ser Gly Gly Pro Leu
    130                 135                 140
Leu Cys Pro Ala Gly His Ala Val Gly Ile Phe Arg Ala Val Cys
145                 150                 155                 160
Thr Arg Gly Val Ala Lys Ala Val Asp Phe Ile Pro Val Glu Ser Leu
                165                 170                 175
Glu Thr Thr Met Arg Ser Pro Val Phe Ser Asp Asn Ser Ser Pro Pro
            180                 185                 190
Ala Val Pro Gln Ser Tyr Gln Val Ala His Leu His Ala Pro Thr Gly
            195                 200                 205
Ser Gly Lys Ser Thr Lys Val Pro Ala Ala Tyr Ala Ala Gln Gly Tyr
    210                 215                 220
Lys Val Leu Val Leu Asn Pro Ser Val Ala Ala Thr Met Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ser Pro Ile Thr Tyr Ser Thr Tyr Gly
            260                 265                 270
Lys Phe Leu Ala Asp Gly Gly Cys Ser Gly Gly Ala Tyr Asp Ile Ile
    275                 280                 285
Ile Cys Asp Glu Cys His Ser Thr Asp Ala Thr Ser Ile Leu Gly Ile
    290                 295                 300
Gly Thr Val Leu Asp Gln Ala Glu Thr Ala Gly Ala Arg Leu Thr Val
305                 310                 315                 320
Leu Ala Thr Ala Thr Pro Pro Gly Ser Val Thr Val Pro His Pro Asn
                325                 330                 335
Ile Glu Glu Val Ala Leu Ser Thr Thr Gly Glu Ile Pro Phe Tyr Gly
            340                 345                 350
Lys Ala Ile Pro Leu Glu Ala Ile Lys Gly Gly Arg His Leu Ile Phe
    355                 360                 365
Cys His Ser Lys Lys Lys Cys Asp Glu Leu Ala Ala Lys Leu Val Ala
    370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                405                 410                 415
Thr Gly Phe Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
    450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
            500                 505                 510
Arg Leu Arg Ala Tyr Met Asn Thr Pro Gly Leu Pro Val Cys Gln Asp
        515                 520                 525
His Leu Glu Phe Trp Glu Gly Val Phe Thr Gly Leu Thr His Ile Asp
    530                 535                 540
```

-continued

```
Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
        580                 585                 590

Leu His Gly Pro Thr Pro Leu Leu Tyr Arg Leu Gly Ala Val Gln Asn
    595                 600                 605

Glu Val Thr Leu Thr His Pro Val Thr Lys Tyr Ile Met Thr Cys Met
610                 615                 620

Ser Ala Asp Leu Glu Val Val Thr Gly Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685
```

<210> SEQ ID NO 32
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQU

```
Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
            245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
            325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
            355                 360                 365

Cys His Ser Lys Lys Cys Asp Glu Leu Ala Ala Lys Leu Val Ala
            370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
            515                 520                 525

His Leu Glu Phe Trp Glu Gly Val Phe Thr Gly Leu Thr His Ile Asp
530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Val Thr Lys Tyr Ile Met Thr Cys Met
            610                 615                 620

Ser Ala Asp Leu Glu Val Val Arg Gly Thr Trp Val Leu Val Gly Gly
625                 630                 635                 640
```

```
Val Leu Ala Ala Leu Ala Ala Tyr Cys Leu Ser Thr Gly Cys Val Val
            645                 650                 655

Ile Val Gly Arg Ile Val Leu Ser Gly Lys Pro Ala Ile Ile Pro Asp
        660                 665                 670

Arg Glu Val Leu Tyr Arg Glu Phe Asp Glu Met Glu Glu Cys
        675                 680                 685

<210> SEQ ID NO 33
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 33

Thr Lys Tyr Met Thr Cys Met Ser Ala Asp Leu Glu Val Val Thr Pro
1               5                   10                  15

Thr Trp Val Leu Val Gly Gly Val Leu
            20                  25

<210> SEQ ID NO 34
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 34

Thr Lys Tyr Met Thr Cys Met Ser Ala Asp Leu Glu Val Val Arg Pro
1               5                   10                  15

Thr Trp Val Leu Val Gly Gly Val Leu
            20                  25

<210> SEQ ID NO 35
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 35

Thr Lys Tyr Met Thr Cys Met Ser Ala Asp Leu Glu Val Val Arg Pro
1               5                   10                  15

Ala Trp Val Leu Val Gly Gly Val Leu
            20                  25

<210> SEQ ID NO 36
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 36

Thr Lys Tyr Met Thr Cys Met Ser Ala Asp Leu Glu Val Val Cys Ser
1               5                   10                  15

Thr Trp Val Leu Val Gly Gly Val Leu
            20                  25

<210> SEQ ID NO 37
<211> LENGTH: 25
<212> TYPE: PRT
<213> ORGANISM: Artificial Sequence
<220> FEATURE:
```

```
<223> OTHER INFORMATION: Mutant Hepatitis C virus NS3/4A peptide

<400> SEQUENCE: 37

Thr Lys Tyr Met Thr Cys Met Ser Ala Asp Leu Glu Val Cys Cys Ser
 1               5                  10                  15

Thr Trp Val Leu Val Gly Gly Val Leu
            20                  25

<210> SEQ ID NO 38
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 38

Thr Lys Tyr Met Thr Cys Met Ser Ala Asp Leu Glu Val Ser Ser Ser
 1               5                  10                  15

Thr Trp Val Leu Val Gly Gly Val Leu
            20                  25

<210> SEQ ID NO 39
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 39

Thr Lys Tyr Met Thr Cys Met Ser Ala Asp Ser Ser Ser Cys Ser
 1               5                  10                  15

Thr Trp Val Leu Val Gly Gly Val Leu
            20                  25

<210> SEQ ID NO 40
<211> LENGTH: 25
<212> TYPE: PRT
<213> ORGANISM: Artificial Sequence
<220> FEATURE:
<223> OTHER INFORMATION: Mutant Hepatitis C virus NS3/4A peptide

<400> SEQUENCE: 40

Thr Lys Tyr Met Thr Cys Met Ser Ala Asp Val Val Val Val Thr Ser
 1               5                  10                  15

Thr Trp Val Leu Val Gly Gly Val Leu
            20                  25

<210> SEQ ID NO 41
<211> LENGTH: 16
<212> TYPE: PRT
<213> ORGANISM: Artificial Sequence
<220> FEATURE:
<223> OTHER INFORMATION: Hepatitis C virus NS5 peptide

<400> SEQUENCE: 41

Ala Ser Glu Asp Val Val Cys Cys Ser Met Ser Tyr Thr Trp Thr Gly
 1               5                  10                  15

<210> SEQ ID NO 42
<211> LENGTH: 18
<212> TYPE: PRT
<213> ORGANISM: Artificial Sequence
<220> FEATURE:
<223> OTHER INFORMATION: Mutant Hepatitis C virus NS5A/B peptide
```

```
<400> SEQUENCE: 42

Ser Ser Glu Asp Val Val Cys Cys Ser Met Trp Val Leu Val Gly Gly
  1               5                  10                  15

Val Leu

<210> SEQ ID NO 43
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 43

Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
                 20                  25                  30

Glu Val Gln Ile Val Ser Thr Ala Gln Thr Phe Leu Ala Thr Cys
             35                  40                  45

Ile Asn Gly Val Cys Trp Thr Val Tyr His Gly Ala Gly Thr Arg Thr
         50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
            115                 120                 125

Ser Pro Arg Pro Ile Ser Tyr Leu Lys Gly Ser Ser Gly Gly Pro Leu
        130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335
```

-continued

```
Ile Glu Glu Val Ala Leu Ser Thr Thr Gly Glu Ile Pro Phe Tyr Gly
            340                 345                 350
Lys Ala Ile Pro Leu Glu Ala Ile Lys Gly Gly Arg His Leu Ile Phe
            355                 360                 365
Cys His Ser Lys Lys Cys Asp Glu Leu Ala Ala Lys Leu Val Ala
            370                 375                 380
Leu Gly Val Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
            405                 410                 415
Thr Gly Phe Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
            435                 440                 445
Thr Ile Thr Leu Pro Gln Asp Ala Val Ser Arg Thr Gln Arg Arg Gly
            450                 455                 460
Arg Thr Gly Arg Gly Lys Pro Gly Ile Tyr Arg Phe Val Ala Pro Gly
465                 470                 475                 480
Glu Arg Pro Ser Gly Met Phe Asp Ser Ser Val Leu Cys Glu Cys Tyr
            485                 490                 495
Asp Ala Gly Cys Ala Trp Tyr Glu Leu Thr Pro Ala Glu Thr Thr Val
            500                 505                 510
Arg Leu Arg Ala Tyr Met Asn Thr Pro Gly Leu Pro Val Cys Gln Asp
            515                 520                 525
His Leu Glu Phe Trp Glu Gly Val Phe Thr Gly Leu Thr His Ile Asp
            530                 535                 540
Ala His Phe Leu Ser Gln Thr Lys Gln Ser Gly Glu Asn Leu Pro Tyr
545                 550                 555                 560
Leu Val Ala Tyr Gln Ala Thr Val Cys Ala Arg Ala Gln Ala Pro Pro
            565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
            595                 600                 605
Glu Val Thr Leu Thr His Pro Val Thr Lys Tyr Ile Met Thr Cys Met
            610                 615                 620
Ser Ala Asp Leu Glu Val Val Thr Pro Thr Trp Val Leu Val Gly Gly
625                 630                 635                 640
Val Leu Ala Ala Leu Ala Ala Tyr Cys Leu Ser Thr Gly Cys Val Val
            645                 650                 655
Ile Val Gly Arg Ile Val Leu Ser Gly Lys Pro Ala Ile Ile Pro Asp
            660                 665                 670
Arg Glu Val Leu Tyr Arg Glu Phe Asp Glu Met Glu Glu Cys
            675                 680                 685
```

<210> SEQ ID NO 44
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 44

```
Met Ala Pro Ile Thr Ala Tyr Ala Gln Gln Thr Arg Gly Leu Leu Gly
 1               5                  10                  15
```

-continued

```
Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
             100                 105                 110

Asp Val Ile Pro Val Arg Arg Arg Gly Asp Gly Arg Gly Ser Leu Leu
         115                 120                 125

Ser Pro Arg Pro Ile Ser Tyr Leu Lys Gly Ser Ser Gly Gly Pro Leu
     130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                 165                 170                 175

Glu Thr Thr Met Arg Ser Pro Val Phe Ser Asp Asn Ser Ser Pro Pro
             180                 185                 190

Ala Val Pro Gln Ser Tyr Gln Val Ala His Leu His Ala Pro Thr Gly
         195                 200                 205

Ser Gly Lys Ser Thr Lys Val Pro Ala Ala Tyr Ala Ala Gln Gly Tyr
     210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                 245                 250                 255

Val Arg Thr Ile Thr Thr Gly Ser Pro Ile Thr Tyr Ser Thr Tyr Gly
             260                 265                 270

Lys Phe Leu Ala Asp Gly Gly Cys Ser Gly Gly Ala Tyr Asp Ile Ile
         275                 280                 285

Ile Cys Asp Glu Cys His Ser Thr Asp Ala Thr Ser Ile Leu Gly Ile
     290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                 325                 330                 335

Ile Glu Glu Val Ala Leu Ser Thr Thr Gly Glu Ile Pro Phe Tyr Gly
             340                 345                 350

Lys Ala Ile Pro Leu Glu Ala Ile Lys Gly Gly Arg His Leu Ile Phe
         355                 360                 365

Cys His Ser Lys Lys Cys Asp Glu Leu Ala Ala Lys Leu Val Ala
     370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                 405                 410                 415

Thr Gly Phe Thr Gly Asp Phe Asp Ser Val Ile Asp Cys Asn Thr Cys
             420                 425                 430
```

-continued

```
Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
        450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Arg Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685
```

<210> SEQ ID NO 45
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 45

```

-continued

Asp Val Ile Pro Val Arg Arg Gly Asp Gly Arg Gly Ser Leu Leu
    115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
                180                 185                 190

Ala Val Pro Gln Ser Tyr Gln Val Ala His Leu His Ala Pro Thr Gly
            195                 200                 205

Ser Gly Lys Ser Thr Lys Val Pro Ala Ala Tyr Ala Ala Gln Gly Tyr
        210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp

```
                530             535             540
Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Val Thr Lys Tyr Ile Met Thr Cys Met
610                 615                 620

Ser Ala Asp Leu Glu Val Val Arg Pro Ala Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
            675                 680                 685
```

<210> SEQ ID NO 46
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 46

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
```

-continued

```
            210                 215                 220
Lys Val Leu Val Leu Asn Pro Ser Val Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
                275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
                340                 345                 350

Lys Ala Ile Pro Leu Glu Ala Ile Lys Gly Gly Arg His Leu Ile Phe
                355                 360                 365

Cys His Ser Lys Lys Cys Asp Glu Leu Ala Ala Lys Leu Val Ala
                370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
                435                 440                 445

Thr Ile Thr Leu Pro Gln Asp Ala Val Ser Arg Thr Gln Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Val Leu Cys Glu Cys Tyr
                485                 490                 495

Asp Ala Gly Cys Ala Trp Tyr Glu Leu Thr Pro Ala Glu Thr Thr Val
                500                 505                 510

Arg Leu Arg Ala Tyr Met Asn Thr Pro Gly Leu Pro Val Cys Gln Asp
                515                 520                 525

His Leu Glu Phe Trp Glu Gly Val Phe Thr Gly Leu Thr His Ile Asp
530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
                595                 600                 605

Glu Val Thr Leu Thr His Pro Val Thr Lys Tyr Ile Met Thr Cys Met
                610                 615                 620

Ser Ala Asp Leu Glu Val Val Cys Ser Thr Trp Val Leu Val Gly Gly
625                 630                 635                 640
```

```
Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 47
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 47

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Ile Val Ser Thr Ala Ala Gln Thr Phe Leu Ala Thr Cys
         35                  40                  45

Ile Asn Gly Val Cys Trp Thr Val Tyr His Gly Ala Gly Thr Arg Thr
     50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320
```

```
Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
            355                 360                 365

Cys His Ser Lys Lys Lys Cys Asp Glu Leu Ala Ala Lys Leu Val Ala
        370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
        530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
            595                 600                 605

Glu Val Thr Leu Thr His Pro Val Thr Lys Tyr Ile Met Thr Cys Met
        610                 615                 620

Ser Ala Asp Leu Glu Val Cys Cys Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 48
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 48
```

-continued

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
               100                 105                 110

Asp Val Ile Pro Val Arg Arg Arg Gly Asp Gly Arg Gly Ser Leu Leu
           115                 120                 125

Ser Pro Arg Pro Ile Ser Tyr Leu Lys Gly Ser Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
            195                 200                 205

Ser Gly Lys Ser Thr Lys Val Pro Ala Ala Tyr Ala Ala Gln Gly Tyr
            210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ala Thr Ser Ile Leu Gly Ile
            290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
                340                 345                 350

Lys Ala Ile Pro Leu Glu Ala Ile Lys Gly Gly Arg His Leu Ile Phe
            355                 360                 365

Cys His Ser Lys Lys Lys Cys Asp Glu Leu Ala Ala Lys Leu Val Ala
            370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
            405                 410                 415
```

```
Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
        450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Ser Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 49
<211> LENGTH: 686
<212> TYPE: PRT
<213> ORGANISM: Artificial Sequence
<220> FEATURE:
<223> OTHER INFORMATION: Mutant Hepatitis C virus NS3/4A

<400> SEQUENCE: 49

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
                20                  25                  30

Glu Val Gln Ile Val Ser Thr Ala Ala Gln Thr Phe Leu Ala Thr Cys
            35                  40                  45

Ile Asn Gly Val Cys Trp Thr Val Tyr His Gly Ala Gly Thr Arg Thr
        50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95
```

```
Pro Cys Thr Cys Gly Ser Ser Asp Leu Tyr Leu Val Thr Arg His Ala
            100                 105                 110

Asp Val Ile Pro Val Arg Arg Gly Asp Gly Arg Gly Ser Leu Leu
            115                 120                 125

Ser Pro Arg Pro Ile Ser Tyr Leu Lys Gly Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
            195                 200                 205

Ser Gly Lys Ser Thr Lys Val Pro Ala Ala Tyr Ala Ala Gln Gly Tyr
        210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
        290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
        370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Gly
        450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
```

-continued

```
            515                 520                 525
His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Ser Ser Ser Cys Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
            675                 680                 685
```

VACCINES CONTAINING RIBAVIRIN AND METHODS OF USE THEREOF

CROSS-REFERENCE TO RELATED APPLICATIONS

This application is a continuation of and claims priority to U.S. patent application Ser. No. 10/817,591, filed Apr. 2, 2004, which is a continuation of and claims priority to U.S. application Ser. No. 09/929,955, filed Aug. 15, 2001 now U.S. Pat. No. 6,858,590, which claims the benefit of priority to U.S. Provisional Patent Applications Nos. 60/225,767 and 60/229,175, filed Aug. 17, 2000 and Aug. 29, 2000;

U.S. patent application Ser. No. 10/817,591 is also a continuation-in-part of U.S. patent application Ser. No. 10/719,619, filed Nov. 20, 2003, which is a continuation of U.S. patent application Ser. No. 10/104,966, filed Mar. 22, 2002, now U.S. Pat. No. 6,680,059, which is a continuation of U.S. patent application Ser. No. 09/705,547, filed on Nov. 3, 2000, now abandon, which also claims the benefit of priority to U.S. Provisional Patent Applications Nos. 60/225,767 and 60/229,175, filed Aug. 17, 2000 and Aug. 29, 2000, respectively. All of the above-referenced patent applications and patent are hereby expressly incorporated by reference in their entireties.

FIELD OF THE INVENTION

The present invention relates to compositions and methods for enhancing the effect of vaccines in animals, such as domestic, sport, or pet species, and humans. More particularly, preferred embodiments concern the use of ribavirin as an adjuvant and compositions having ribavirin and an antigen.

BACKGROUND OF THE INVENTION

The use of vaccines to prevent disease in humans, farm livestock, sports animals, and household pets is a common practice. Frequently, however, the antigen used in a vaccine is not sufficiently immunogenic to raise the antibody titre to levels that are sufficient to provide protection against subsequent challenge or to maintain the potential for mounting these levels over extended time periods. Further, many vaccines are altogether deficient in inducing cell-mediated immunity, which is a primary immune defense against bacterial and viral infection. A considerable amount of research is currently focussed on the development of more potent vaccines and ways to enhance the immunogenicity of antigen-containing preparations. (See e.g., U.S. Pat. Nos. 6,056,961; 6,060,068; 6,063,380; and Li et al., *Science* 288:2219-2222 (2000)).

Notorious among such "weak" vaccines are hepatitis B vaccines. For example, recombinant vaccines against hepatitis B virus such as Genhevacb (Pasteur Merieux Serums et Vaccines, 58, Avenue Leclerc 69007 Lyon, France), Engerixb (Smith, Kline and Symbol French), and Recombivaxhb (Merck, Sharp, and Dhome) are effective only after at least three injections at 0, 30, and 60 or 180 days, followed by an obligatory booster after one year. (Chedid et al., U.S. Pat. No. 6,063,380). Additionally, many subjects receiving these vaccines respond poorly, if at all. Because many regions of the world are endemic for HBV infection, the poorly immunogenic character of existing HBV vaccines has become an extremely serious problem.

To obtain a stronger, humoral and/or cellular response, it is common to administer a vaccine in a material that enhances the immune response of the patient to the antigen present in the vaccine. The most commonly used adjuvants for vaccine protocols are oil preparations and alum. (Chedid et al., U.S. Pat. No. 6,063,380). A greater repertoire of safe and effective adjuvants is needed.

Nucleoside analogs have been widely used in anti-viral therapies due to their capacity to reduce viral replication. (Hosoya et al., *J. Inf. Dis.*, 168:641-646 (1993)). ribavirin (1-β-D-ribofuranosyl-1,2,4-triazole-3-carboxamide) is a synthetic guanosine analog that has been used to inhibit RNA and DNA virus replication. (Huffman et al., *Antimicrob. Agents. Chemother.*, 3:235 (1973); Sidwell et al., *Science*, 177:705 (1972)). ribavirin has been shown to be a competitive inhibitor of inositol mono-phosphate (IMP) dehydrogenase (IMPDH), which converts IMP to IMX (which is then converted to GMP). De Clercq, *Anti viral Agents: characteristic activity spectrum depending on the molecular target with which they interact*, Academic press, Inc., New York N.Y., pp. 1-55 (1993). Intracellular pools of GTP become depleted as a result of long term ribavirin treatment.

In addition to antiviral activity, investigators have observed that some guanosine analogs have an effect on the immune system. (U.S. Pat. Nos. 6,063,772 and 4,950,647), ribavirin has been shown to inhibit functional humoral immune responses (Peavy et al., *J. Immunol.*, 126:861-864 (1981); Powers et al., *Antimicrob. Agents. Chemother.*, 22:108-114 (1982)) and IgE-mediated modulation of mast cell secretion. (Marquardt et al., *J. Pharmacol. Exp. Therapeutics*, 240:145-149 (1987)). Some investigators report that a daily oral therapy of ribavirin has an immune modulating effect on humans and mice. (Hultgren et al., *J. Gen. Virol.*, 79:2381-2391 (1998) and Cramp et al., *Gastron. Enterol.*, 118:346-355 (2000)). Nevertheless, the current understanding of the effects of ribavirin on the immune system is in its infancy.

SUMMARY OF THE INVENTION

It has been discovered that ribavirin can be used as an adjuvant to enhance or facilitate an immune response to an antigen. Embodiments of the invention described herein include "strong" vaccine preparations that comprise an antigen and ribavirin. Generally, these preparations have an amount of ribavirin that is sufficient to enhance or facilitate an immune response to the antigen. Other aspects of the invention include methods of enhancing or facilitating an immune response of an animal, including a human, to an antigen. By one approach, for example, an animal in need of a potent immune response to an antigen is identified and then is provided an amount of ribavirin together with the antigen. In some methods, the ribavirin and the antigen are provided in combination (e.g., in a single composition) and in others, the ribavirin and the antigen are provided separately. Several embodiments also concern the manufacture and use of compositions having ribavirin and an antigen.

Although the embodied compositions include ribavirin and virtually any antigen or epitope, preferred compositions comprise ribavirin and a hepatitis viral antigen or epitope. The antigen or epitope can be peptide or nucleic acid-based (e.g., a RNA encoding a peptide antigen or a construct that expresses a peptide antigen when introduced to a subject). Compositions having ribavirin and a peptide comprising an antigen or epitope from the hepatitis A virus (HAV) or a nucleic acid encoding said peptide are embodiments. Compositions having ribavirin and a peptide comprising an antigen or epitope from the hepatitis B virus (HBV) or a nucleic acid encoding said peptide are embodiments. HBV antigens that are suitable include, for example, hepatitis B surface antigen (HBsAg), hepatitis core antigen (HBcAg), hepatitis e antigen (HBeAg), and nucleic acids encoding these molecules. Still further, compositions having ribavirin and a peptide comprising an antigen or epitope from the hepatitis C virus (HCV) or a nucleic acid encoding said peptide are embodiments. Suitable HCV antigens include, but are not limited to, one or more domains of the HCV sequence (e.g., NS3 and/or NS4A) and nucleic acids encoding said molecules.

A new HCV sequence was also discovered. A novel NS3/4A fragment of the HCV genome was cloned and sequenced from a patient infected with HCV (SEQ. ID. NO.: 16). This sequence was found to be only 93% homologous to the most closely related HCV sequence. This novel peptide (SEQ. ID. NO.: 17) and fragments thereof at least 3, 4, 6, 8, 10, 12, 15 or 20 amino acids in length, nucleic acids encoding these molecules, vectors having said nucleic acids, and cells having said vectors, nucleic acids, or peptides are also embodiments of the present invention. A particularly preferred embodiment is a vaccine composition comprising ribavirin and the HCV peptide of SEQ. ID. NO.: 17 or a fragment thereof at least 3, 4, 6, 8, 10, 12, 15 or 20 amino acids in length (e.g., SEQ. ID. NO.: 25) or a nucleic acid encoding said peptide or fragments.

Additionally, it was discovered that truncated mutants and mutants of the NS3/4A peptide, which lack a proteolytic cleavage site, are highly immunogenic. These novel peptides (SEQ. ID. NOs.: 29-32 and 43-49) and fragments thereof at least 3, 4, 6, 8, 10, 12, 15 or 20 amino acids in length (e.g., SEQ. ID. NOs.: 26, 27, and 33-42), nucleic acids encoding these molecules, vectors having said nucleic acids, and cells having said vectors, nucleic acids, or peptides are also embodiments. A particularly preferred embodiment is a vaccine composition comprising ribavirin and at least one HCV peptide of SEQ. ID. NOs.: 29-32 and 43-49 or a fragment thereof at least 3, 4, 6, 8, 10, 12, 15 or 20 amino acids in length (e.g., SEQ. ID. NOs.: 26, 27, and 33-42) or a nucleic acid encoding said peptides or fragments.

Furthermore, compositions having a mixture of the antigens above are embodiments of the invention. For example, some compositions comprise a HBV antigen, a HAV antigen, and ribavirin or a HBV antigen, a HCV antigen, and ribavirin or a HAV antigen, a HCV antigen, and ribavirin or a HBV antigen, a HAV antigen, a HCV antigen, and ribavirin. Other embodiments comprise ribavirin and a nucleic acid encoding a mixture of the antigens described above. Some embodiments also include other adjuvants, binders, emulsifiers, carriers, and fillers, as known in the art, including, but not limited to, alum, oil, and other compounds that enhance an immune response.

Methods of making and using the compositions described herein are also aspects of the invention. Some methods are practiced by mixing ribavirin with a peptide or nucleic acid antigen (e.g., an HAV, HBV, HCV antigen) so as to formulate a single composition (e.g., a vaccine composition). Preferred methods involve the mixing of ribavirin with an HCV antigen that has an epitope present on one or more domains of HCV (e.g., NS3 and/or NS4A).

Preferred methods of using the compositions described herein involve providing an animal in need with a sufficient amount of ribavirin and a hepatitis viral antigen (e.g., HBV antigen, HAV antigen, HCV antigen a nucleic acid encoding one of these antigens or any combination thereof). By one approach, for example, an animal in need of potent immune response to a hepatitis viral antigen (e.g., an animal at risk or already infected with a hepatitis infection) is identified and said animal is provided an amount of ribavirin and a hepatitis viral antigen (either in a single composition or separately) that is effective to enhance or facilitate an immune response to the hepatitis viral antigen. Preferably, an animal in need of a potent immune response to HCV is identified and said animal is provided a composition comprising ribavirin and a peptide comprising an antigen or epitope present on SEQ. ID. NO.: 1, 6, 7, or 17 or a nucleic acid encoding said peptide. Particularly preferred methods involve the identification of an animal in need of an potent immune response to HCV and providing said animal a composition comprising ribavirin and an amount of an HCV antigen (e.g., NS3/4A (SEQ. ID. NO.: 17), mutant NS3/4A SEQ. ID. NOs.: 29-32 and 43-49, or a fragment thereof at least 3, 4-10, 10-20, 20-30, or 30-50 amino acids in length (e.g., SEQ. ID. NOs.: 25-27, and 33-42) or a nucleic acid encoding one or more of these molecules) that is sufficient to enhance or facilitate an immune response to said antigen.

DETAILED DESCRIPTION OF THE INVENTION

Figure 1:
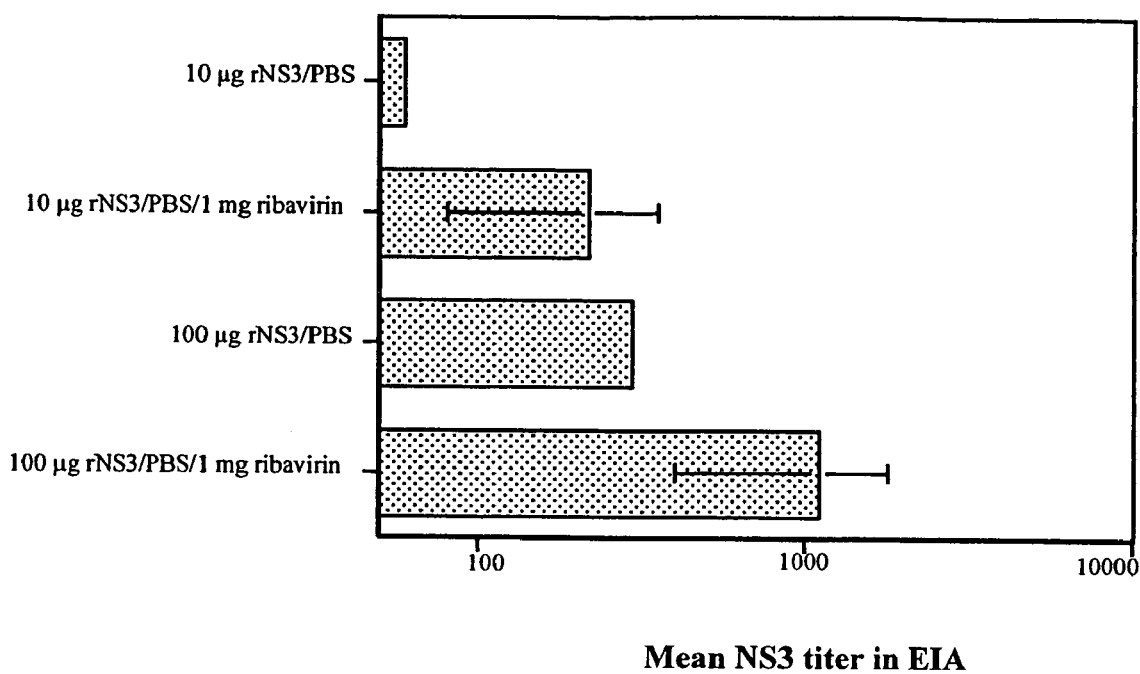
FIG. 1 is a graph showing the humoral response to 10 and 100 μg recombinant Hepatitis C virus (HCV) non structural 3 protein (NS3), as determined by mean end point titres, when a single dose of 1 mg of ribavirin was co-administered.

It has been discovered that compositions comprising ribavirin and an antigen (e.g., a molecule containing an epitope of a pathogen such as a virus, bacteria, mold, yeast, or parasite) enhance and/or facilitate an animal's immune response to the antigen. That is, it was discovered that ribavirin is an effective "adjuvant," which for the purposes of this disclosure, refers to a material that has the ability to enhance or facilitate an immune response to a particular antigen. The adjuvant activity of ribavirin was manifested by a significant increase in immune-mediated protection against the antigen, an increase in the titer of antibody raised to the antigen, and an increase in proliferative T cell responses.

Several compositions (e.g., vaccines) that comprise ribavirin and an antigen or epitope are described herein. Vaccine formulations containing ribavirin, for example, can vary according to the amount of ribavirin, the form of ribavirin, and the type of antigen. The antigen can be a peptide or a nucleic acid (e.g., a RNA encoding a peptide antigen or a construct that expresses a peptide antigen when introduced into a subject). Preferred compositions comprise ribavirin and a hepatitis viral antigen (e.g., HAV antigen, HBV antigen, HCV antigen, a nucleic acid encoding these molecules, or any combination thereof). In particular, at least one HCV antigen or an epitope present on SEQ. ID. NO.: 1 or a nucleic acid encoding said HCV antigen are desired for mixing with ribavirin to make said compositions. That is, some embodiments include, but are not limited to, compositions comprising ribavirin and a peptide comprising SEQ. ID. NO.: 1, or a fragment thereof having at least 2500, 2000, 1600, 1200, 800, 400, 200, 100, 50, 10, or 3 consecutive amino acids of SEQ. ID. NO.: 1. Additional embodiments concern compositions comprising ribavirin and a nucleic acid encoding SEQ. ID. NO.: 13 or a fragment thereof having at least 9, 12, 15, 20, 30, 50, 75, 100, 200, 500 consecutive nucleotides of SEQ. ID. NO.: 13.

Other embodiments include a composition (e.g., a vaccine) that comprises ribavirin and a specific fragment of SEQ. ID. NO.: 1, wherein said fragment corresponds to a particular domain of HCV. Some embodiments, for example, comprise a fragment of HCV corresponding to amino acids 1-182, 183-379, 380-729, 730-1044, 1045-1657, 1658-1711, 1712-1971, or 1972-3011 of SEQ. ID. NO.: 1. Compositions comprising ribavirin and a nucleic acid encoding one or more of these fragments are also embodiments of the invention.

Additionally, a novel HCV sequence was discovered. A novel nucleic acid and protein corresponding to the NS3/4A domain of HCV was cloned from a patient infected with HCV (SEQ. ID. NO.: 16). A Genebank search revealed that the cloned sequence had the greatest homology to HCV sequences but was only 93% homologous to the closest HCV relative (accession no AJ 278830). This novel peptide (SEQ. ID. NO.: 17) and fragments thereof at least 3, 4, 6, 8, 10, 12, 15 or 20 amino acids in length, nucleic acids encoding these molecules, vectors having said nucleic acids, and cells having said vectors, nucleic acids, or peptides are also embodiments of the invention. Further, some of the vaccine embodiments described herein comprise ribavirin and this novel NS3/4A peptide or a fragment thereof at least 3, 4, 6, 8, 10, 12, 15 or 20 amino acids in length (e.g., SEQ. ID. NO.: 25) or a nucleic acid encoding one or more of these molecules.

Mutants of the novel NS3/4A peptide were also created. It was discovered that truncated mutants (e.g., SEQ. ID. NO.: 29) and mutants, which lack a proteolytic cleavage site, are highly immunogenic. These novel peptides SEQ. ID. NOs.: 29-32 and 43-49 and fragments thereof at least 3, 4, 6, 8, 10, 12, 15 or 20 amino acids in length (e.g., SEQ. ID. NOs.: 26, 27, and 33-42), nucleic acids encoding these molecules, vectors having said nucleic acids, and cells having said vectors, nucleic acids, or peptides are also embodiments. Furthermore, some of the compositions described herein comprise ribavirin and at least one of the mutant HCV peptides described above or a fragment thereof at least 3, 4, 6, 8, 10, 12, 15 or 20 amino acids in length. Other vaccine embodiments comprise ribavirin and a nucleic acid (e.g., DNA) encoding one or more of the peptides described above.

Methods of making and using the compositions above are also embodiments. For example, the compositions described above can be made by providing ribavirin, providing an antigen (e.g., a peptide comprising an HCV antigen or a nucleic acid encoding said peptide), and mixing said ribavirin and said antigen so as to formulate a composition that can be used to enhance or facilitate an immune response in a subject to said antigen. Preferred methods entail mixing a preferred antigen or epitope (e.g., a peptide comprising SEQ. ID. NO.: 1, 6, 7, or 17 or specific fragments thereof, such as amino acids 1-182, 183-379, 380-729, 730-1044, 1045-1657, 1658-1711, 1712-1971, 1972-3011 of SEQ. ID. NO.: 1 and nucleic acids encoding these molecules) with ribavirin. Other antigens or epitopes can also be mixed with ribavirin including, but not limited to, fragments of SEQ. ID. NO.: 1 that have at least 2500, 2000, 1600, 1200, 800, 400, 200, 100, 50, 10, or 3 consecutive amino acids and nucleic acids encoding these fragments. Particularly preferred methods concern the making of vaccine compositions comprising the newly discovered NS3/4A fragment or an NS3/4A mutant (e.g., a truncated mutant or a mutant lacking a proteolytic cleavage site), or a fragment thereof of at least four amino acids in length or a nucleic acid encoding one or more of these molecules.

Methods of enhancing or facilitating the immune response of an animal, including humans, to an antigen are embodiments of the invention. Such methods can be practiced, for example, by identifying an animal in need of a potent immune response to an antigen/epitope and providing said animal a composition comprising the antigen/epitope and an amount of ribavirin that is effective to enhance or facilitate an immune response to the antigen/epitope. In some embodiments, the ribavirin and the antigen are administered separately, instead of in a single mixture. Preferably, in this instance, the ribavirin is administered a short time before or a short time after admininstering the antigen. Preferred methods involve providing the animal in need with ribavirin and a hepatitis antigen (e.g., HAV antigen, HBV antigen, HCV antigen, a nucleic acid encoding these molecules, or any combination thereof). Some of these methods involve HCV antigens, such as a peptide comprising SEQ. ID. NO.: 1, or a fragment thereof having at least 2500, 2000, 1600, 1200, 800, 400, 200, 100, 50, 10, or 3 consecutive amino acids of SEQ. ID. NO.: 1. Additional methods involve compositions comprising ribavirin and a nucleic acid encoding SEQ. ID. NO.: 13 or a nucleic acid encoding one or more of the fragments discussed above.

Some preferred methods, for example, concern the use of a composition (e.g., a vaccine) that comprises ribavirin and a peptide comprising SEQ. ID. NO.: 1 or a specific fragment thereof, which corresponds to an HCV domain including, but not limited to, a peptide comprising amino acids 1-182, 183-379, 380-729, 730-1044, 1045-1657, 1658-1711, 1712-1971, or 1972-3011 of SEQ. ID. NO.: 1. Particularly preferred methods concern the use of a vaccine composition comprising the NS3/4A fragment of SEQ. ID. NO.: 17 or the mutant NS3/4A (e.g., SEQ. ID. NOs:. 29-32 and 43-49), which lack a proteolytic cleavage site, or a fragment thereof of at least 3, 4, 6, 8, 10, 12, 15 or 20 amino acids in length (e.g., SEQ. ID. NOs.: 26, 27, and 33-42). Compositions comprising ribavirin and a nucleic acid encoding these fragments can also be used with the methods described herein.

Other embodiments concern methods of treating and preventing HCV infection. By one approach, ribavirin and an HCV antigen or epitope are used to prepare a medicament for the treatment and/or prevention of HCV infection. By another approach, an individual in need of a medicament that prevents and/or treats HCV infection is identified and said individual is provided a medicament comprising ribavirin and an HCV antigen or epitope, preferably an epitope present on SEQ. ID. NO.: 1, more preferably a fragment of SEQ. ID. NO.: 1 having at least 2500, 2000, 1600, 1200, 800, 400, 200, 100, 50, 10, or 3 consecutive amino acids or most preferably a fragment of SEQ. ID. NO.: 1 such as 1-182, 183-379, 380-729, 730-1044, 1045-1657, 1658-1711, 1712-1971, or 1972-3011 or a nucleic acid encoding SEQ. ID. NO.: 1 or said fragments above. Particularly preferred methods concern the use of a vaccine composition comprising ribavirin and the NS3/4A fragment of SEQ. ID. NO.: 17 or the mutant NS3/4A, which lacks a proteolytic cleavage site (e.g., SEQ. ID. NOs.: 29-32 and 43-49) or a fragment thereof of at least 3, 4, 6, 8, 10, 12, 15 or 20 amino acids in length (e.g., SEQ. ID. NOs.: 25-27, and 33-42) or a nucleic acid encoding one or more of these molecules. The section below discusses the use of ribavirin as an adjuvant in greater detail.

Ribavirin

The compositions described herein can be manufactured in accordance with conventional methods of galenic pharmacy to produce medicinal agents for administration to animals, e.g., mammals including humans. Ribavirin can be obtained from commercial suppliers (e.g., Sigma and ICN). Ribavirin and/or the antigen can be formulated into the vaccine with and without modification. For example, the ribavirin and/or antigen can be modified or derivatized to make a more stable molecule and/or a more potent adjuvant. By one approach, the stability of ribavirin and/or an antigen can be enhanced by coupling the molecules to a support such as a hydrophilic polymer (e.g., polyethylene glycol).

Many more ribavirin derivatives can be generated using conventional techniques in rational drug design and combinatorial chemistry. For example, Molecular Simulations Inc. (MSI), as well as many other suppliers, provide software that allows one of skill to build a combinatorial library of organic molecules. The C2.Analog Builder program, for example, can be integrated with MSI's suite of Cerius2 molecular diversity software to develop a library of ribavirin derivatives that can be used with the embodiments described herein.

By one approach, the chemical structure of ribavirin is recorded on a computer readable medium and is accessed by one or more modeling software application programs. The C2.Analog Builder program in conjunction with C2Diversity program allows the user to generate a very large virtual library based on the diversity of R-groups for each substituent position, for example. Compounds having the same structure as the modeled ribavirin derivatives created in the virtual library are then made using conventional chemistry or can be obtained from a commercial source.

The newly manufactured ribavirin derivatives are then screened in assays, which determine the extent of adjuvant activity of the molecule and/or the extent of its ability to modulate of an immune response. Some assays may involve virtual drug screening software, such as C2.Ludi. C2.Ludi is a software program that allows a user to explore databases of molecules (e.g., ribavirin derivatives) for their ability to interact with the active site of a protein of interest (e.g., RAC2 or another GTP binding protein). Based upon predicted interactions discovered with the virtual drug screening software, the ribavirin derivatives can be prioritized for further characterization in conventional assays that determine adjuvant activity and/or the extent of a molecule to modulate an immune response. Example 1 describes several assays that were used to evaluate the adjuvant activity of ribavirin.

EXAMPLE 1

This following assays can be used with any ribavirin derivative or combinations of ribavirin derivatives to determine the extent of adjuvant activity of the particular composition. In a first set of experiments, groups of three to five Balb/c mice (BK Universal, Uppsala, Sweden) were immunized i.p or s.c. (e.g., at the base of the tail) with 10 µg or 100 µg of recombinant hepatitis C virus non-structural 3 (rNS3) protein at weeks zero and four. The rNS3 was dissolved in phosphate buffered saline (PBS) alone or PBS containing 1 mg ribavirin (obtained from ICN, Costa Mesa, Calif.). Mice were injected with a total volume of 100 µl per injection.

At two, four, and six weeks following first i.p. immunization, all mice were bled by retro-orbital sampling. Serum samples were collected and analyzed for the presence of antibodies to rNS3. To determine the antibody titer, an enzyme immunoassay (EIA) was performed. (See e.g., Hultgren et al., *J Gen Virol.* 79:2381-91 (1998) and Hultgren et al., *Clin. Diagn. Lab. Immunol.* 4:630-632 (1997), both of which are herein expressly incorporated by reference in their entireties). The antibody levels were recorded as the highest serum dilution giving an optical density at 405 nm more than twice that of non-immunized mice.

Mice that received 10 µg or 100 µg rNS3 mixed with 1 mg ribavirin in PBS displayed consistently higher levels of NS3 antibodies. The antibody titer that was detected by EIA at two weeks post-immunization is shown in FIG. 1. The vaccine formulations having 1 mg of ribavirin and either 10 µg or 100 µg of rNS3 induced a significantly greater antibody titer than the vaccine formulations composed of only rNS3.

In a second set of experiments, groups of eight Balb/c mice were at weeks zero and four immunized intraperitoneally with 10 or 50 µg of rNS3 in 100 µl phosphate buffered saline containing either 0 mg, 1 mg, 3 mg, or 10 mg ribavirin (Sigma). At four, six and eight weeks the mice were bled and serum was separated and frozen. After completion of the study, sera were tested for the levels of antibodies to recombinant NS3, as described above. Mean antibody levels to rNS3 were compared between the groups using Student's t-test (parametric analysis) or Mann-Whitney (non-parametric analysis) and the software package StatView 4.5 (Abacus Concepts, Berkely, Calif.). The adjuvant effect of ribavirin when added in three doses to 10 µg of rNS3 are provided in TABLE 1. The adjuvant effect of ribavirin when added in three doses to 50 µg of rNS3 are provided in TABLE 2. Parametrical comparison of the mean rNS3 antibody titres in mice receiving different 10 µg or 50 µg of rNS3 and different doses of ribavirin are provided in TABLES 3 and 4, respectively. Non-parametrical comparison of mean NS3 antibody titres in mice receiving different 10 µg or 50 µg of rNS3 and different does of ribavirin are provided in TABLES 5 and 6, respectively. The values given represent end point titres to recombinant rNS3.

TABLE 1

| Amount ribavirin (mg/dose) | Amount immunogen (μg/dose) | Mouse ID | Antibody titre to rNS3 at indicated week | | |
|---|---|---|---|---|---|
| | | | Week 4 | Week 6 | Week 8 |
| None | 10 | 5:1 | 300 | 1500 | 1500 |
| None | 10 | 5:2 | <60 | 7500 | 1500 |
| None | 10 | 5:3 | <60 | 1500 | 300 |
| None | 10 | 5:4 | 60 | 1500 | 1500 |
| None | 10 | 5:5 | <60 | 1500 | nt |
| None | 10 | 5:6 | 60 | 1500 | 1500 |
| None | 10 | 5:7 | <60 | 7500 | 7500 |
| None | 10 | 5:8 | 300 | 37500 | 7500 |
| Group mean titre (mean ± SD) | | | 180 ± 139 | 7500 ± 12421 | 3042 ± 3076 |
| 1 | 10 | 6:1 | 300 | 37500 | 37500 |
| 1 | 10 | 6:2 | <60 | 1500 | 1500 |
| 1 | 10 | 6:3 | 300 | 37500 | 187500 |
| 1 | 10 | 6:4 | 300 | 37500 | 7500 |
| 1 | 10 | 6:5 | 60 | nt | nt |
| 1 | 10 | 6:6 | <60 | 37500 | 7500 |
| 1 | 10 | 6:7 | <60 | 37500 | 7500 |
| 1 | 10 | 6:8 | 300 | 7500 | 7500 |
| Group mean titre (mean ± SD) | | | 252 ± 107 | 28071 ± 16195 | 36642 ± 67565 |
| 3 | 10 | 7:1 | 60 | 37500 | 7500 |
| 3 | 10 | 7:2 | 60 | 37500 | 37500 |
| 3 | 10 | 7:3 | 300 | 7500 | 7500 |
| 3 | 10 | 7:4 | 300 | 37500 | 7500 |
| 3 | 10 | 7:5 | 300 | 37500 | 37500 |
| 3 | 10 | 7:6 | 300 | 37500 | 37500 |
| 3 | 10 | 7:7 | 60 | 7500 | 7500 |
| 3 | 10 | 7:8 | 60 | 37500 | 37500 |
| Group mean titre (mean ± SD) | | | 180 ± 128 | 30000 ± 13887 | 22500 ± 34637 |
| 10 | 10 | 8:1 | 300 | 37500 | 37500 |
| 10 | 10 | 8:2 | 300 | 37500 | 37500 |
| 10 | 10 | 8:3 | <60 | 300 | 300 |
| 10 | 10 | 8:4 | 60 | 7500 | 7500 |
| 10 | 10 | 8:5 | <60 | 300 | 300 |
| 10 | 10 | 8:6 | <60 | 37500 | 37500 |
| 10 | 10 | 8:7 | <60 | 7500 | 7500 |
| 10 | 10 | 8:8 | <60 | nt | nt |
| Group mean titre (mean ± SD) | | | 220 ± 139 | 18300 ± 18199 | 18300 ± 18199 |

TABLE 2

| Amount ribavirin (mg/dose) | Amount immunogen (μg/dose) | Mouse ID | Antibody titre to rNS3 at indicated week | | |
|---|---|---|---|---|---|
| | | | Week 4 | Week 6 | Week 8 |
| None | 50 | 1:1 | 60 | 7500 | 7500 |
| None | 50 | 1:2 | 60 | 7500 | 7500 |
| None | 50 | 1:3 | 60 | 7500 | 7500 |
| None | 50 | 1:4 | <60 | 1500 | 300 |
| None | 50 | 1:5 | 300 | 37500 | 37500 |
| None | 50 | 1:6 | 60 | 7500 | 7500 |
| None | 50 | 1:7 | 60 | 37500 | 7500 |
| None | 50 | 1:8 | — | — | — |
| Group mean titre (mean ± SD) | | | 100 ± 98 | 15214 ± 15380 | 10757 ± 12094 |
| 1 | 50 | 2:1 | 60 | 7500 | 7500 |
| 1 | 50 | 2:2 | 300 | 37500 | 7500 |
| 1 | 50 | 2:3 | 60 | 187500 | 7500 |
| 1 | 50 | 2:4 | 60 | 37500 | 187500 |
| 1 | 50 | 2:5 | 60 | 37500 | 7500 |
| 1 | 50 | 2:6 | 60 | 37500 | 37500 |
| 1 | 50 | 2:7 | 300 | 37500 | 7500 |
| 1 | 50 | 2:8 | 300 | 37500 | 37500 |
| Group mean titre (mean ± SD) | | | 150 ± 124 | 52500 ± 55549 | 37500 ± 62105 |
| 3 | 50 | 3:1 | 60 | 37500 | 7500 |
| 3 | 50 | 3:2 | 300 | 37500 | 37500 |
| 3 | 50 | 3:3 | 300 | 37500 | 7500 |
| 3 | 50 | 3:4 | 60 | 37500 | 7500 |
| 3 | 50 | 3:5 | 300 | 37500 | 7500 |
| 3 | 50 | 3:6 | 60 | 37500 | 7500 |
| 3 | 50 | 3:7 | — | 7500 | 37500 |
| 3 | 50 | 3:8 | 1500 | 7500 | 37500 |
| Group mean titre (mean ± SD) | | | 387 ± 513 | 30000 ± 13887 | 18750 ± 15526 |

TABLE 2-continued

| Amount ribavirin (mg/dose) | Amount immunogen (µg/dose) | Mouse ID | Antibody titre to rNS3 at indicated week | | |
|---|---|---|---|---|---|
| | | | Week 4 | Week 6 | Week 8 |
| 10 | 50 | 4:1 | 300 | 7500 | 7500 |
| 10 | 50 | 4:2 | 300 | 37500 | 37500 |
| 10 | 50 | 4:3 | 60 | 7500 | 7500 |
| 10 | 50 | 4:4 | 60 | 7500 | 7500 |
| 10 | 50 | 4:5 | 60 | 1500 | 1500 |
| 10 | 50 | 4:6 | 60 | 7500 | 37500 |
| 10 | 50 | 4:7 | — | 7500 | 7500 |
| 10 | 50 | 8:8 | 60 | 37500 | 7500 |
| Group mean titre (mean ± SD) | | | 140 ± 124 | 10929 ± 11928 | 15214 ± 15380 |

TABLE 3

| Group | Week | Mean ± SD | Group | Mean ± SD | analysis | p-value |
|---|---|---|---|---|---|---|
| 10 µg NS3/no ribavirin | 4 | 180 ± 139 | 10 µg NS3/ 1 mg ribavirin | 252 ± 107 | Students t-test | 0.4071 |
| | 6 | 7500 ± 12421 | | 28071 ± 16195 | Students t-test | 0.0156 |
| | 8 | 3042 ± 3076 | | 36642 ± 67565 | Students t-test | 0.2133 |
| 10 µg NS3/no ribavirin | 4 | 180 ± 139 | 10 µg NS3/ 3 mg ribavirin | 180 ± 128 | Students t-test | 1.000 |
| | 6 | 7500 ± 12421 | | 30000 ± 13887 | Students t-test | 0.0042 |
| | 8 | 3042 ± 3076 | | 22500 ± 34637 | Students t-test | 0.0077 |
| 10 µg NS3/no ribavirin | 4 | 180 ± 139 | 10 µg NS3/ 10 mg ribavirin | 220 ± 139 | Students t-test | 0.7210 |
| | 6 | 7500 ± 12421 | | 18300 ± 18199 | Students t-test | 0.1974 |
| | 8 | 3042 ± 3076 | | 18300 ± 18199 | Students t-test | 0.0493 |

TABLE 4

| Group | Week | Mean ± SD | Group | Mean ± SD | analysis | p-value |
|---|---|---|---|---|---|---|
| 50 µg NS3/no ribavirin | 4 | 100 ± 98 | 50 µg NS3/ 1 mg ribavirin | 150 ± 124 | Students t-test | 0.4326 |
| | 6 | 15214 ± 15380 | | 52500 ± 55549 | Students t-test | 0.1106 |
| | 8 | 10757 ± 12094 | | 37500 ± 62105 | Students t-test | 0.2847 |
| 50 µg NS3/no ribavirin | 4 | 100 ± 98 | 50 µg NS3/ 3 mg ribavirin | 387 ± 513 | Students t-test | 0.2355 |
| | 6 | 15214 ± 15380 | | 30000 ± 13887 | Students t-test | 0.0721 |
| | 8 | 10757 ± 12094 | | 18750 ± 15526 | Students t-test | 0.2915 |
| 50 µg NS3/no ribavirin | 4 | 100 ± 98 | 50 µg NS3/ 10 mg ribavirin | 140 ± 124 | Students t-test | 0.5490 |
| | 6 | 15214 ± 15380 | | 10929 ± 11928 | Students t-test | 0.5710 |
| | 8 | 10757 ± 12094 | | 15214 ± 15380 | Students t-test | 0.5579 |

Significance levels:
NS = not significant;
* = p < 0.05;
** = p < 0.01;
*** = p < 0.001

TABLE 5

| Group | Week | Mean ± SD | Group | Mean ± SD | analysis | p-value |
|---|---|---|---|---|---|---|
| 10 µg NS3/no ribavirin | 4 | 180 ± 139 | 10 µg NS3/ 1 mg ribavirin | 252 ± 107 | Mann-Whitney | 0.4280 |

TABLE 5-continued

| Group | Week | Mean ± SD | Group | Mean ± SD | analysis | p-value |
|---|---|---|---|---|---|---|
| | 6 | 7500 ± 12421 | | 28071 ± 16195 | Mann-Whitney | 0.0253 |
| | 8 | 3042 ± 3076 | | 36642 ± 67565 | Mann-Whitney | 0.0245 |
| 10 µg NS3/no ribavirin | 4 | 180 ± 139 | 10 µg NS3/ 3 mg ribavirin | 180 ± 128 | Mann-Whitney | 0.0736 |
| | 6 | 7500 ± 12421 | | 30000 ± 13887 | Mann-Whitney | 0.0050 |
| | 8 | 3042 ± 3076 | | 22500 ± 34637 | Mann-Whitney | 0.0034 |
| 10 µg NS3/no ribavirin | 4 | 180 ± 139 | 10 µg NS3/ 10 mg ribavirin | 220 ± 139 | Mann-Whitney | 0.8986 |
| | 6 | 7500 ± 12421 | | 18300 ± 18199 | Mann-Whitney | 0.4346 |
| | 8 | 3042 ± 3076 | | 18300 ± 18199 | Mann-Whitney | 0.2102 |

TABLE 6

| Group | Week | Mean ± SD | Group | Mean ± SD | analysis | p-value |
|---|---|---|---|---|---|---|
| 50 µg NS3/no ribavirin | 4 | 100 ± 98 | 50 µg NS3/ 1 mg ribavirin | 150 ± 124 | Mann-Whitney | 0.1128 |
| | 6 | 15214 ± 15380 | | 52500 ± 55549 | Mann-Whitney | 0.0210 |
| | 8 | 10757 ± 12094 | | 37500 ± 62105 | Mann-Whitney | 0.1883 |
| 50 µg NS3/no ribavirin | 4 | 100 ± 98 | 50 µg NS3/ 3 mg ribavirin | 387 ± 513 | Mann-Whitney | 0.1400 |
| | 6 | 15214 ± 15380 | | 30000 ± 13887 | Mann-Whitney | 0.0679 |
| | 8 | 10757 ± 12094 | | 18750 ± 15526 | Mann-Whitney | 0.2091 |
| 50 µg NS3/no ribavirin | 4 | 100 ± 98 | 50 µg NS3/ 10 mg ribavirin | 140 ± 124 | Mann-Whitney | 0.4292 |
| | 6 | 15214 ± 15380 | | 10929 ± 11928 | Mann-Whitney | 0.9473 |
| | 8 | 10757 ± 12094 | | 15214 ± 15380 | Mann-Whitney | 0.6279 |

Significance levels:
NS = not significant;
* = p < 0.05;
** = p < 0.01;
*** = p < 0.001

The data above demonstrate that ribavirin facilitates or enhances an immune response to an HCV antigen or HCV epitopes. A potent immune response to rNS3 was elicited after immunization with a vaccine composition comprising as little as 1 mg ribavirin and 10 µg of rNS3 antigen. The data above also provide evidence that the amount of ribavirin that is sufficient to facilitate an immune response to an antigen is between 1 and 3 mg per injection for a 25-30 g Balb/c mouse. It should be realized, however, that these amounts are intended for guidance only and should not be interpreted to limit the scope of the invention in any way. Nevertheless, the data shows that vaccine compositions comprising approximately 1 to 3 mg doses of ribavirin induce an immune response that is more than 12 times higher than the immune response elicited in the absence of ribavirin (TABLES 3 and 4). Thus, ribavirin has a significant adjuvant effect on the humoral immune response of an animal and thereby, enhances or facilitates the immune response to the antigen. The example below describes experiments that were performed to better understand the amount of ribavirin needed to enhance or facilitate an immune response to an antigen.

EXAMPLE 2

Figure 2:
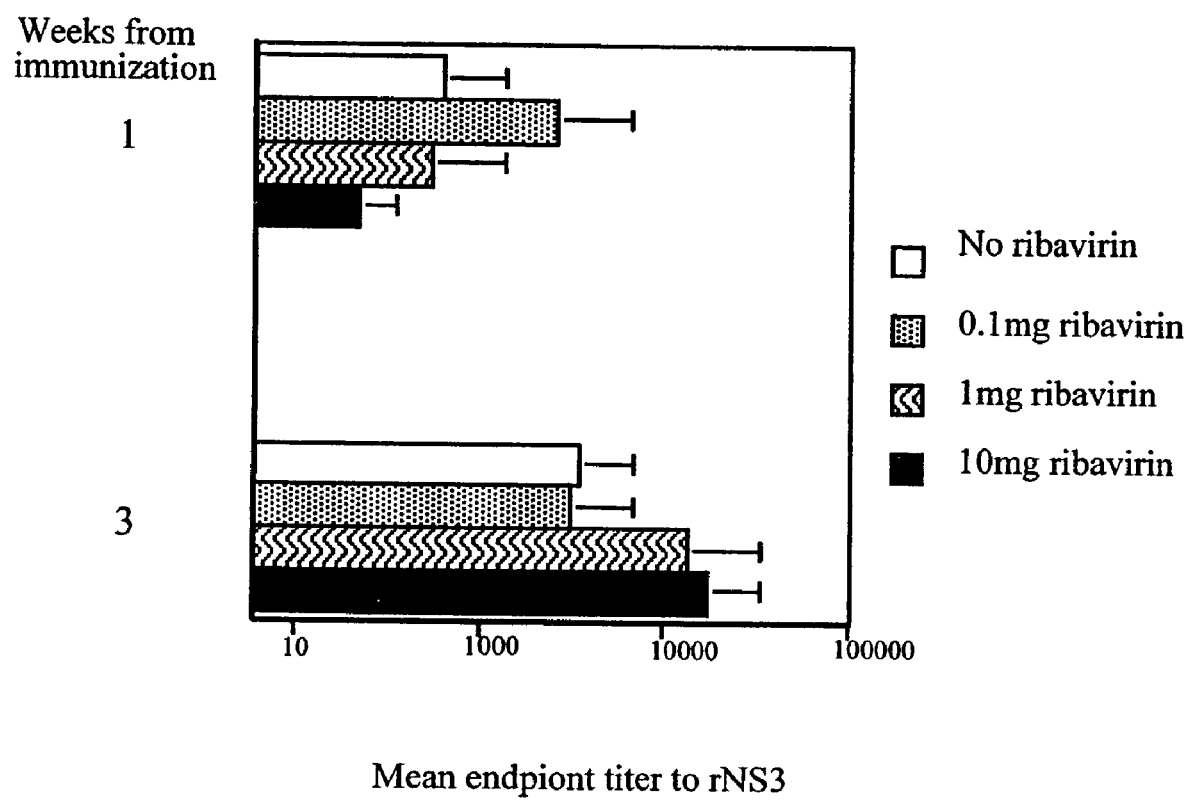
FIG. 2 is a graph showing the humoral response to 20 μg recombinant Hepatitis C virus (HCV) non structural 3 protein (NS3), as determined by mean end point titres, when a single dose of 0.1, 1.0, or 10 mg of ribavirin was co-administered.

To determine a dose of ribavirin that is sufficient to provide an adjuvant effect, the following experiments were performed. In a first set of experiments, groups of mice (three per group) were immunized with a 20 µg rNS3 alone or a mixture of 20 µg rNS3 and 0.1 mg, 1 mg, or 10 mg ribavirin. The levels of antibody to the antigen were then determined by EIA. The mean endpoint titers at weeks 1 and 3 were plotted and are shown in FIG. 2. It was discovered that the adjuvant effect provided by ribavirin had different kinetics depending on the dose of ribavirin provided. For example, even low doses (<1 mg) of ribavirin were found to enhance antibody levels at week one but not at week three, whereas, higher doses (1-10 mg) were found to enhance antibody levels at week three.

A second set of experiments was also performed. In these experiments, groups of mice were injected with vaccine compositions comprising various amounts of ribavirin and rNS3 and the IgG response in these animals was monitored. The vaccine compositions comprised approximately 100 µl phosphate buffered saline and 20 µg rNS3 with or without 0.1 mg, 1.0 mg, or 10 mg ribavirin (Sigma). The mice were bled at week six and rNS3-specific IgG levels were determined by EIA as described previously. As shown in TABLE 7, the adjuvant effects on the sustained antibody levels were most obvious in the dose range of 1 to 10 mg per injection for a 25-30 g mouse.

The data presented in this example further verify that ribavirin can be administered as an adjuvant and establish that that the dose of ribavirin can modulate the kinetics of the adjuvant effect. The example below describes another assay that was performed to evaluate the ability of ribavirin to enhance or facilitate an immune response to an antigen.

TABLE 7

| Immunogen | Amount (mg) ribavirin mixed with the immunogen | Mouse ID | Endpoint titre of rNS3 IgG at indicated week | | |
|---|---|---|---|---|---|
| | | | Week 1 | Week 2 | Week 3 |
| 20 μg rNS3 | None | 1 | 60 | 360 | 360 |
| 20 μg rNS3 | None | 2 | 360 | 360 | 2160 |
| 20 μg rNS3 | None | 3 | 360 | 2160 | 2160 |
| | | Mean | 260 ± 173 | 960 ± 1039 | 1560 ± 1039 |
| 20 μg rNS3 | 0.1 | 4 | 2160 | 12960 | 2160 |
| 20 μg rNS3 | 0.1 | 5 | 60 | 60 | 60 |
| 20 μg rNS3 | 0.1 | 6 | <60 | 2160 | 2160 |
| | | | 1110 ± 1484 | 5060 ± 6921 | 1460 ± 1212 |
| 20 μg rNS3 | 1.0 | 7 | <60 | 60 | 12960 |
| 20 μg rNS3 | 1.0 | 8 | <60 | 2160 | 2160 |
| 20 μg rNS3 | 1.0 | 9 | 360 | 2160 | 2160 |
| | | Mean | 360 | 1460 ± 1212 | 5760 ± 6235 |
| 20 μg rNS3 | 10.0 | 10 | 360 | 12960 | 77760 |
| 20 μg rNS3 | 10.0 | 11 | <60 | 2160 | 12960 |
| 20 μg rNS3 | 10.0 | 12 | 360 | 2160 | 2160 |
| | | Mean | 360 | 5760 ± 6235 | 30960 ± 40888 |

In a third set of experiments, the adjuvant effect of ribavirin after primary and booster injections was investigated. In these experiments, mice were given two intraperitoneal injections of a vaccine composition comprising 10 μg rNS3 with or without ribavirin and the IgG subclass responses to the antigen was monitored, as before. Accordingly, mice were immunized with 100 μl phosphate buffered containing 10 μg recombinant NS3 alone, with or without 0.1 or 1.0 mg ribavirin (Sigma) at weeks 0 and 4. The mice were bled at week six and NS3-specific IgG subclasses were determined by EIA as described previously. As shown in TABLE 8, the addition of ribavirin to the immunogen prior to the injection does not change the IgG subclass response in the NS3-specific immune response. Thus, the adjuvant effect of a vaccine composition comprising ribavirin and an antigen can not be explained by a shift in the Th1/Th2-balance. It appears that another mechanism may be responsible for the adjuvant effect of ribavirin.

EXAMPLE 3

This assay can be used with any ribavirin derivative or combinations of ribavirin derivatives to determine the extent that a particular vaccine formulation modulates a cellular immune response. To determine CD4$^+$ T cell responses to a ribavirin-containing vaccine, groups of mice were immunized s.c. with either 100 μg rNS3 in PBS or 100 μg rNS3 and 1 mg ribavirin in PBS. The mice were sacrificed ten days post-immunization and their lymph nodes were harvested and drained. In vitro recall assays were then performed. (See e.g., Hultgren et al., *J Gen Virol.* 79:2381-91 (1998) and Hultgren et al., *Clin. Diagn. Lab. Immunol.* 4:630-632 (1997), both of which are herein expressly incorporated by reference in their entireties). The amount of CD4$^+$ T cell proliferation was determined at 96 h of culture by the incorporation of [$^3$H] thymidine.

TABLE 8

| Immunogen | Amount (mg) ribavirin mixed with the immunogen | Mouse ID | Endpoint titre of indicated NS3 IgG subclass | | | |
|---|---|---|---|---|---|---|
| | | | IgG1 | IgG2a | IgG2b | IgG3 |
| 10 μg rNS3 | None | 1 | 360 | 60 | <60 | 60 |
| 10 μg rNS3 | None | 2 | 360 | <60 | <60 | 60 |
| 10 μg rNS3 | None | 3 | 2160 | 60 | <60 | 360 |
| | | Mean | 960 ± 1039 | 60 | — | 160 ± 173 |
| 10 μg rNS3 | 0.1 | 4 | 360 | <60 | <60 | 60 |
| 10 μg rNS3 | 0.1 | 5 | 60 | <60 | <60 | <60 |
| 10 μg rNS3 | 0.1 | 6 | 2160 | 60 | 60 | 360 |
| | | | 860 ± 1136 | 60 | 60 | 210 ± 212 |
| 10 μg rNS3 | 1.0 | 7 | 2160 | <60 | <60 | 60 |
| 10 μg rNS3 | 1.0 | 8 | 360 | <60 | <60 | <60 |
| 10 μg rNS3 | 1.0 | 9 | 2160 | <60 | <60 | 60 |
| | | Mean | 1560 ± 1039 | — | — | 60 |

Figure 3:
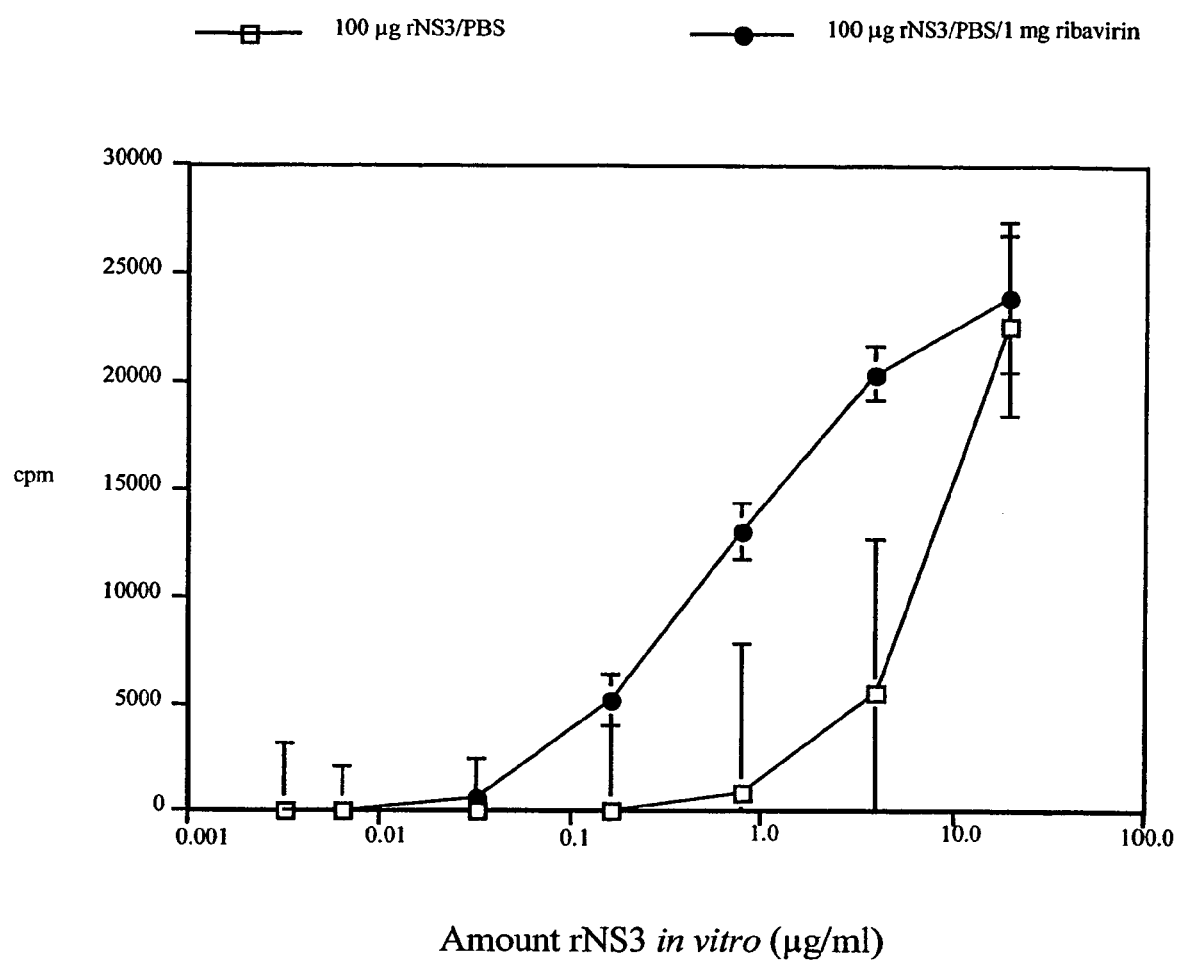
FIG. 3 is a graph showing the effects of a single dose of 1 mg ribavirin on NS3-specific lymph node proliferative responses, as determined by in vitro recall responses.

As shown in FIG. 3, mice that were immunized with 100 µg rNS3 mixed with 1 mg ribavirin had a much greater T cell proliferative response than mice that were immunized with 100 µg rNS3 in PBS. These data provide additional evidence that ribavirin enhances or facilitates a cellular immune response (e.g., by promoting the effective priming of T cells). The section below discusses some of the antigens and epitopes that can be used with the embodiments described herein.

Antigens and Epitopes

Virtually any antigen that can be used to generate an immune response in an animal can be combined with ribavirin so as to prepare the compositions described herein. That is, antigens that can be incorporated into such compositions (e.g., vaccines) comprise bacterial antigens or epitopes, fungal antigens or epitopes, plant antigens or epitopes, mold antigens or epitopes, viral antigens or epitopes, cancer cell antigens or epitopes, toxin antigens or epitopes, chemical antigens or epitopes, and self-antigens or epitopes. Although many of these molecules induce a significant immune response without an adjuvant, ribavirin can be administered in conjunction with or combined with "strong" or "weak" antigens or epitopes to enhance or facilitate the immune response to said antigen or epitope. In addition, the use of ribavirin as an adjuvant may allow for the use of lesser amounts of antigens while retaining immunogenicity.

In addition to peptide antigens, nucleic acid-based antigens can be used in the vaccine compositions described herein. Various nucleic acid-based vaccines are known and it is contemplated that these compositions and approaches to immunotherapy can be augmented by reformulation with ribavirin (See e.g., U.S. Pat. Nos. 5,589,466 and 6,235,888, both of which are herein expressly incorporated by reference in their entireties). By one approach, for example, a gene encoding a polypeptide antigen of interest is cloned into an expression vector capable of expressing the polypeptide when introduced into a subject. The expression construct is introduced into the subject in a mixture of ribavirin or in conjunction with ribavirin (e.g., ribavirin is administered shortly after the expression construct at the same site). Alternatively, RNA encoding a polypeptide antigen of interest is provided to the subject in a mixture with ribavirin or in conjunction with ribavirin.

Where the antigen is to be DNA (e.g., preparation of a DNA vaccine composition), suitable promoters include Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metalothionein can be used. Examples of polyadenylation signals useful with some embodiments, especially in the production of a genetic vaccine for humans, include but are not limited to, SV40 polyadenylation signals and LTR polyadenylation signals. In particular, the SV40 polyadenylation signal, which is in pCEP4 plasmid (Invitrogen, San Diego Calif.), referred to as the SV40 polyadenylation signal, is used.

In addition to the regulatory elements required for gene expression, other elements may also be included in a gene construct. Such additional elements include enhancers. The enhancer may be selected from the group including but not limited to: human actin, human myosin, human hemoglobin, human muscle creatine and viral enhancers such as those from CMV, RSV and EBV. Gene constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region, which produces high copy episomal replication without integration. All forms of DNA, whether replicating or non-replicating, which do not become integrated into the genome, and which are expressible, can be used. The example below describes the use of a composition comprising a nucleic acid-based antigen and ribavirin.

EXAMPLE 4

The following describes the immunization of an animal with a vaccine comprising a nucleic acid-based antigen and ribavirin. Five to six week old female and male Balb/C mice are anesthetized by intraperitoneal injection with 0.3 ml of 2.5% Avertin. A 1.5 cm incision is made on the anterior thigh, and the quadriceps muscle is directly visualized. One group of mice are injected with approximately 20 µg of an expression construct having the gp-120 gene, driven by a cytomegalovirus (CMV) promotor and second group of mice are injected with approximately 5 µg of capped in vitro transcribed RNA (e.g., SP6, T7, or T3 (Ambion)) encoding gp-120. These two groups are controls. A third group of mice is injected with approximately 20 µg of the expression vector having the gp-120 gene and the CMV promoter mixed with 1 mg of ribavirin and a fourth group of mice is injected with approximately 5 µg of capped in vitro transcribed RNA mixed with 1 mg ribavirin. The vaccines are injected in 0.1 ml of solution (PBS) in a 1 cc syringe through a 27 gauge needle over one minute, approximately 0.5 cm from the distal insertion site of the muscle into the knee and about 0.2 cm deep. A suture is placed over the injection site for future localization, and the skin is then closed with stainless steel clips.

Blood samples are obtained prior to the injection (Day 0) and up to more than 40 days post injection. The serum from each sample is serially diluted and assayed in a standard ELISA technique assay for the detection of antibody, using recombinant gp-120 protein made in yeast as the antigen. Both IgG and IgM antibodies specific for gp-120 will be detected in all samples, however, groups three and four, which contained the ribavirin, will exhibit a greater immune response to the gp-120 as measured by the amount and/or titer of antibody detected in the sera.

Preferred embodiments of the invention comprise ribavirin and a viral antigen or an epitope present on a virus, preferably a hepatitis virus. Compositions comprise, for example, ribavirin and an HAV antigen, HBV antigen, HCV antigen or any combination of these antigens or epitopes present on one or more of these viruses. The hepatitis antigens can be peptides or nucleic acids. Compositions that can be used to vaccinate against HAV infection, for example, comprise ribavirin and an HAV peptide with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, 800-1200 consecutive amino acids, 1200-1600 consecutive amino acids, 1600-2000 consecutive amino acids, and 2000-2227 consecutive amino acids of SEQ ID. NO.: 12.

Additionally, compositions comprising ribavirin and a nucleic acid encoding one or more of the HAV peptides, described above, can be used to treat or prevent HAV infection. Preferred nucleic acid-based antigens include a nucleotide sequence of at least 9 consecutive nucleotides of an HAV sequence (e.g., SEQ. ID. NO.: 15). That is, a nucleic acid based antigen can comprise at least 9-25 consecutive nucleotides, 25-50 consecutive nucleotides, 50-100 consecutive nucleotides, 100-200 consecutive nucleotides, 200-500 consecutive nucleotides, 500-1000 consecutive nucleotides, 1000-2000 consecutive nucleotides, 2000-4000 consecutive nucleotides, 4000-8000 consecutive nucleotides, and 8000-9416 consecutive nucleotides of SEQ. ID. NO.: 15 or an RNA that corresponds to these sequences.

Similarly, preferred HBV vaccine embodiments comprise ribavirin and a HBV peptide of at least 3 consecutive amino acids of HBsAg (SEQ. ID. NO.: 10) or HBcAg and HBeAg (SEQ. ID. NO.: 11). That is, some embodiments have ribavirin and a HBV peptide with a length of at least 3-10 consecutive amino acids, 10-50 consecutive amino acids, 50-100 consecutive amino acids, 100-150 consecutive amino acids, 150-200 consecutive amino acids, and 200-226 consecutive amino acids of either SEQ. ID. NO.: 10 or SEQ. ID. NO.: 11.

Additionally, compositions comprising ribavirin and a nucleic acid encoding one or more of the HBV peptides, described above, can be used to treat or prevent HBV infection. Preferred nucleic acid-based antigens include a nucleotide sequence of at least 9 consecutive nucleotides of an HBV (e.g., SEQ. ID. NO.:14). That is, a nucleic acid based antigen can comprise at least 9-25 consecutive nucleotides, 25-50 consecutive nucleotides, 50-100 consecutive nucleotides, 100-200 consecutive nucleotides, 200-500 consecutive nucleotides, 500-1000 consecutive nucleotides, 1000-2000 consecutive nucleotides, 2000-4000 consecutive nucleotides, 4000-8000 consecutive nucleotides, and 8000-9416 consecutive nucleotides of SEQ. ID. NO.: 14 or an RNA that corresponds to these sequences. The example below describes the use of ribavirin in conjunction with a commercial HBV vaccine preparation.

EXAMPLE 5

The adjuvant effect of ribavirin was tested when mixed with two doses of a commercially available vaccine containing HBsAg and alum. (Engerix, SKB). Approximately 0.2 μg or 2 μg of Engerix vaccine was mixed with either PBS or 1 mg ribavirin in PBS and the mixtures were injected intraperitoneally into groups of mice (three per group). A booster containing the same mixture was given on week four and all mice were bled on week six. The serum samples were diluted from 1:60 to 1:37500 and the dilutions were tested by EIA, as described above, except that purified human HBsAg was used as the solid phase antigen. As shown in TABLE 9, vaccine formulations having ribavirin enhanced the response to 2 μg of an existing vaccine despite the fact that the vaccine already contained alum. That is, by adding ribavirin to a suboptimal vaccine dose (i.e., one that does not induce detectable antibodies alone) antibodies became detectable, providing evidence that the addition of ribavirin allows for the use of lower antigen amounts in a vaccine formulation without compromising the immune response.

TABLE 9

| | Endpoint antibody titer to HBsAg in EIA | | | | | | | | | | | |
|---|---|---|---|---|---|---|---|---|---|---|---|---|
| | 0.02 μg Engerix | | | | | | 0.2 μg Engerix | | | | | |
| | No ribavirin | | | 1 mg ribavirin | | | No ribavirin | | | 1 mg ribavirin | | |
| Week | #1 | #2 | #3 | #1 | #2 | #3 | #1 | #2 | #3 | #1 | #2 | #3 |
| 6 | <60 | <60 | <60 | <60 | <60 | <60 | <60 | <60 | <60 | 300 | 60 | <60 |

Some HCV vaccine compositions comprise ribavirin and a HCV peptide of at least 3 consecutive amino acids of SEQ. ID. NO.: 1 or a nucleic acid encoding said HCV peptide. That is, a vaccine composition can comprise ribavirin and one or more HCV peptides with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, 800-1200 consecutive amino acids, 1200-1600 consecutive amino acids, 1600-2000 consecutive amino acids, 2000-2500 consecutive amino acids, and 2500-3011 consecutive amino acids of SEQ. ID. NO.: 1 or a nucleic acid encoding one or more of said fragments.

Preferred HCV compositions comprise ribavirin and a peptide of at least 3 consecutive amino acids of HCV core protein (SEQ. ID. NO.: 2), HCV E1 protein (SEQ. ID. NO.: 3), HCV E2 protein (SEQ. ID. NO.: 4), HCV NS2 (SEQ. ID. NO.: 5), HCV NS3 (SEQ. ID. NO.: 6), HCV NS4A (SEQ. ID. NO.: 7), HCV NS4B (SEQ. ID. NO.: 8), or HCV NS5A/B (SEQ. ID. NO.: 9) or peptides consisting of combinations of these domains. That is, preferred HCV vaccines comprise ribavirin and a peptide with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, and 800-1040 consecutive amino acids of any one or more of (SEQ. ID. NOs.: 2-9). These domains correspond to amino acid residues 1-182, 183-379, 380-729, 730-1044, 1045-1657, 1658-1711, 1712-1971, or 1972-3011 of SEQ. ID. NO.: 1. Thus, preferred embodiments also include one or more of 1-182, 183-379, 380-729, 730-1044, 1045-1657, 1658-1711, 1712-1971, or 1972-3011 of SEQ. ID. NO.: 1 or fragments thereof.

Vaccine compositions comprising ribavirin and a nucleic acid encoding one or more of the peptides described above are also embodiments. Preferred nucleic acid-based antigens include a nucleotide sequence of at least 9 consecutive nucleotides of HCV (SEQ. ID. NO.: 13). That is, a nucleic acid based antigen can comprise at least 9-25 consecutive nucleotides, 25-50 consecutive nucleotides, 50-100 consecutive nucleotides, 100-200 consecutive nucleotides, 200-500 consecutive nucleotides, 500-1000 consecutive nucleotides, 1000-2000 consecutive nucleotides, 2000-4000 consecutive nucleotides, 4000-8000 consecutive nucleotides, and 8000-9416 consecutive nucleotides of any one of SEQ. ID. NOs.: 13 or an RNA that corresponds to these sequences. The section below discusses some of the compositions containing ribavirin and an antigen.

Compositions Containing Ribavirin and an Antigen

Compositions (e.g., vaccines) that comprise ribavirin and an antigen or epitope of a pathogen (e.g., virus, bacteria, mold, yeast, and parasite) may contain other ingredients including, but not limited to, adjuvants, binding agents, excipients such as stabilizers (to promote long term storage), emulsifiers, thickening agents, salts, preservatives, solvents, dispersion media, coatings, antibacterial and antifungal agents, isotonic and absorption delaying agents and the like. These compositions are suitable for treatment of animals either as a preventive measure to avoid a disease or condition or as a therapeutic to treat animals already afflicted with a disease or condition.

Many other ingredients can be present in the vaccine. For example, the ribavirin and antigen can be employed in admixture with conventional excipients (e.g., pharmaceutically acceptable organic or inorganic carrier substances suitable for parenteral, enteral (e.g., oral) or topical application that do not deleteriously react with the ribavirin and/or antigen). Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable carriers are described in Remmington's Pharmaceutical Sciences, 15th Edition, Easton:Mack Publishing Company, pages 1405-1412 and 1461-1487(1975) and The National Formulary XIV, 14th Edition, Washington, American Pharmaceutical Association (1975), herein expressly incorporated by reference in their entireties.

The gene constructs described herein may be formulated with or administered in conjunction with agents that increase uptake and/or expression of the gene construct by the cells relative to uptake and/or expression of the gene construct by the cells that occurs when the identical genetic vaccine is administered in the absence of such agents. Such agents and the protocols for administering them in conjunction with gene constructs are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, PCT Patent Application Serial Number PCT/US94/00899 filed Jan. 26, 1994, and U.S. Ser. No. 08/221,579 filed Apr. 1, 1994, which are each incorporated herein by reference in their entirety. Examples of such agents include: $CaPO_4$, DEAE dextran, anionic lipids; extracellular matrix-active enzymes; saponins; lectins; estrogenic compounds and steroidal hormones; hydroxylated lower alkyls; dimethyl sulfoxide (DMSO); urea; and benzoic acid esters anilides, amidines, urethanes and the hydrochloride salts thereof such as those of the family of local anesthetics. In addition, the gene constructs are encapsulated within/administered in conjunction with lipids/polycationic complexes.

Vaccines can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with ribavirin or the antigen.

The effective dose and method of administration of a particular vaccine formulation can vary based on the individual patient and the type and stage of the disease, as well as other factors known to those of skill in the art. Therapeutic efficacy and toxicity of the vaccines can be determined by standard pharmaceutical procedures in cell cultures or experimental animals, e.g., $ED_{50}$ (the dose therapeutically effective in 50% of the population). The data obtained from cell culture assays and animal studies can be used to formulate a range of dosage for human use. The dosage of the vaccines lies preferably within a range of circulating concentrations that include the $ED_{50}$ with no toxicity. The dosage varies within this range depending upon the type of ribavirin derivative and antigen, the dosage form employed, the sensitivity of the patient, and the route of administration.

Since ribavirin has been on the market for several years, many dosage forms and routes of administration are known. All known dosage forms and routes of administration can be provided within the context of the embodiments described herein. Preferably, an amount of ribavirin that is effective to enhance an immune response to an antigen in an animal can be considered to be an amount that is sufficient to achieve a blood serum level of antigen approximately 0.25-12.5 µg/ml in the animal, preferably, about 2.5 µg/ml. In some embodiments, the amount of ribavirin is determined according to the body weight of the animal to be given the vaccine. Accordingly, the amount of ribavirin in a vaccine formulation can be from about 0.1-6.0 mg/kg body weight. That is, some embodiments have an amount of ribavirin that corresponds to approximately 0.1-1.0 mg/kg, 1.1-2.0 mg/kg, 2.1-3.0 mg/kg, 3.1-4.0 mg/kg, 4.1-5.0 mg/kg, 5.1, and 6.0 mg/kg body weight of an animal. More conventionally, the vaccines contain approximately 0.25 mg -2000 mg of ribavirin. That is, some embodiments have approximately 250 µg, 500 µg, 1 mg, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1,8 g, 1.9 g, and 2 g of ribavirin.

Conventional vaccine preparations can be modified by adding an amount of ribavirin that is sufficient to enhance an immune response to the antigen. That is, existing conventional vaccine formulations can be modified by simply adding ribavirin to the preparation or by administering the conventional vaccine in conjunction with ribavirin (e.g., shortly before or after providing the antigen). As one of skill in the art will appreciate, the amount of antigens in a vaccine can vary depending on the type of antigen and its immunogenicity. The amount of antigens in the vaccines can vary accordingly. Nevertheless, as a general guide, the vaccines can have approximately 0.25 mg -5 mg, 5-10 mg, 10-100 mg, 100-500 mg, and upwards of 2000 mg of an antigen (e.g., a hepatitis viral antigen).

In some approaches described herein, the exact amount of ribavirin and/or antigen is chosen by the individual physician in view of the patient to be treated. Further, the amounts of ribavirin can be added in combination with or separately from the same or equivalent amount of antigen and these amounts can be adjusted during a particular vaccination protocol so as to provide sufficient levels in light of patient-specific or antigen-specific considerations. In this vein, patient-specific and antigen-specific factors that can be taken into account include, but are not limited to, the severity of the disease state of the patient, age, and weight of the patient, diet, time and frequency of administration, drug combination(s), reaction sensitivities, and tolerance/response to therapy. The next section describes the discovery of a novel HCV gene and the creation of mutant HCV sequences, which can be used with the embodiments described herein.

Novel NS3/4A and Mutant NS3/4A Sequences

A novel nucleic acid and protein corresponding to the NS3/4A domain of HCV was cloned from a patient infected with HCV (SEQ. ID. NOs.: 16 and 17). A Genebank search revealed that the cloned sequence had the greatest homology to HCV sequences but was only 93% homologous to the closest HCV relative (accession no AJ 278830). A truncated mutant of the novel NS3/4A peptide and NS3/4A mutants, which lack a proteolytic cleavage site, were also created. It was discovered that these novel peptides and nucleic acids encoding said peptides were potent immunogens that can be mixed with ribavirin so as to make a composition that provides a recipient with a potent immune response to HCV. The cloning of the novel NS3/4A domain and the creation of the various NS3/4A mutants is described in the following example.

EXAMPLE 6

The NS3/4A sequence was amplified from the serum of an HCV-infected patient (HCV genotype 1a) using the Polymerase Chain Reaction (PCR). Total RNA was extracted from serum, cDNA synthesis, and PCR was performed according to standard protocols (Chen M et al., *J. Med. Virol.* 43:223-226 (1995), herein expressly incorporated by reference in its entirety). The cDNA synthesis was initiated using the antisense primer "NS4KR" (5'-CCG TCT AGA TCA GCA CTC TTC CAT TTC ATC-3' (SEQ. ID. NO.: 18)). From this cDNA, a 2079 base pair DNA fragment of HCV, corresponding to amino acids 1007 to 1711, which encompasses the NS3 and NS4A genes, was amplified. A high fidelity polymerase (Expand High Fidelity PCR, Boehringer-Mannheim, Mannheim, Germany) was used with the "NS3KF" primer (5'-CCT GAA TTC ATG GCG CCT ATC ACG GCC TAT-3' (SEQ. ID. NO.: 19) and the NS4KR primer. The NS3KF primer contained a EcoRI restriction enzyme cleavage site and a start codon and the primer NS4KR contained a XbaI restriction enzyme cleavage site and a stop codon.

The amplified fragment was then sequenced SEQ. ID. NO.: 16. Sequence comparison analysis revealed that the gene fragment was indeed amplified from a viral strain of genotype 1a. A computerized BLAST search against the Genbank database using the NCBI website revealed that the closest HCV homologue was 93% identical in nucleotide sequence.

The amplified DNA fragment was then digested with EcoRI and XbaI, and was inserted into a pcDNA3.1/His plasmid (Invitrogen) digested with the same enzymes. The NS3/4A-pcDNA3.1 plasmid was then digested with EcoRI and XbaI and the insert was purified using the QiaQuick kit (Qiagen, Hamburg, Germany) and was ligated to a EcoRI/XbaI digested pVAX vector (Invitrogen) so as to generate the NS3/4A-pVAX plasmid.

The rNS3 truncated mutant was obtained by deleting NS4A sequence from the NS3/4A DNA. Accordingly, the NS3 gene sequence of NS3/4A-pVAX was PCR amplified using the primers NS3KF and 3' NotI (5'-CCA CGC GGC CGC GAC GAC CTA CAG-3' (SEQ. ID. NO.: 20)) containing EcoRI and NotI restriction sites, respectively. The NS3 fragment (1850 bp) was then ligated to a EcoRI and NotI digested pVAX plasmid to generate the NS3-pVAX vector. Plasmids were grown in BL21 *E. coli* cells. The plasmids were sequenced and were verified by restriction cleavage and the results were as to be expected based on the original sequence.

To change the proteolytic cleavage site between NS3 and NS4A, the NS3/4A-pVAX plasmid was mutagenized using the QUICKCHANGE™ mutagenesis kit (Stratagene), following the manufacturer's recommendations. To generate the "TPT" mutation, the plasmid was amplified using the primers 5'-CTGGAGGTCGTCACGCCTACCTGGGT-GCTCGTT-3' (SEQ. ID. NO.: 21) and 5'-ACCGAGCAC-CCAGGTAGGCGTGACGACCTCCAG-3' (SEQ. ID. NO.: 22) resulting in NS3/4A-TPT-pVAX. To generate the "RGT" mutation, the plasmid was amplified using the primers 5'-CTGGAGGTCGTCCGCGGTACCTGGGTGCTCGTT-3' (SEQ. ID. NO.: 23) and 5'-ACCGAGCACCCAGGTAC-CGCGGACGACCTCCAG-3' (SEQ. ID. NO.: 24) resulting in NS3/4A-RGT-pVAX.

All mutagenized constructs were sequenced to verify that the mutations had been correctly made. Plasmids were grown in competent BL21 *E. coli*. The plasmid DNA used for in vivo injection was purified using Qiagen DNA purification columns, according to the manufacturers instructions (Qiagen GmbH, Hilden, FRG). The concentration of the resulting plasmid DNA was determined spectrophotometrically (Dynaquant, Pharmacia Biotech, Uppsala, Sweden) and the purified DNA was dissolved in sterile phosphate buffer saline (PBS) at concentrations of 1 mg/ml. The amino acid sequences of the wild-type and mutated junctions are shown in TABLE 10. The section below describes several nucleic acids that encode HCV peptides.

TABLE 10

| Plasmid | Deduced amino acid sequence |
|---|---|
| *NS3/4A-pVAX | TKYMTCMSADLEVV<u>TST</u>WVLVGGVL (SEQ. ID. NO.: 25) |
| NS3/4A-TGT-pVAX | TKYMTCMSADLEVV<u>TGT</u>WVLVGGVL (SEQ. ID. NO.: 26) |
| NS3/4A-RGT-pVAX | TKYMTCMSADLEVV<u>RGT</u>WVLVGGVL (SEQ. ID. NO.: 27) |
| NS3/4A-TPT-pVAX | TKYMTCMSADLEVV<u>TPT</u>WVLVGGVL (SEQ. ID. NO.: 33) |
| NS3/4A-RPT-pVAX | TKYMTCMSADLEVV<u>RPT</u>WVLVGGVL (SEQ. ID. NO.: 34) |
| NS3/4A-RPA-pVAX | TKYMTCMSADLEVV<u>RPA</u>WVLVGGVL (SEQ. ID. NO.: 35) |
| NS3/4A-CST-pVAX | TKYMTCMSADLEVV<u>CST</u>WVLVGGVL (SEQ. ID. NO.: 36) |
| NS3/4A-CCST-pVAX | TKYMTCMSADLEVC<u>CST</u>WVLVGGVL (SEQ. ID. NO.: 37) |
| NS3/4A-SSST-pVAX | TKYMTCMSADLEVS<u>SST</u>WVLVGGVL (SEQ. ID. NO.: 38) |
| NS3/4A-SSSSCST-pVAX | TKYMTCMSADSSSS<u>CST</u>WVLVGGVL (SEQ. ID. NO.: 39) |

TABLE 10-continued

| Plasmid | Deduced amino acid sequence |
|---|---|
| NS3A/4A-VVVVTST-pVAX | TKYMTCMSADVVVV<u>TST</u>WVLVGGVL (SEQ. ID. NO.: 40) |
| NS5-pVAX | ASEDVVC<u>CSM</u>SYTWTG (SEQ. ID. NO.: 41) |
| NS5A/B-pVAX | SSEDVVC<u>CSM</u>WVLVGGVL (SEQ. ID. NO.: 42) |

*The wild type sequence for the NS3/4A fragment is NS3/4A-pVAX. The NS3/4A breakpoint is identified by underline, wherein the P1 position corresponds to the first Thr (T) and the P1' position corresponds to the next following amino acid the NS3/4A-pVAX sequence. In the wild type NS3/4A sequence the NS3 protease cleaves between the P1 and P1' positions.

Nucleic Acids Encoding HCV Peptides

The nucleic acid embodiments include nucleotides encoding the HCV peptides described herein (e.g., SEQ. ID. NO.: 17, 29, 31, 32, and 43-49) or fragments thereof at least 4, 6, 8, 10, 12, 15, or 20 amino acids in length (e.g., SEQ. ID. NOs.: 25-27, and 33-42). Some embodiments for example, include genomic DNA, RNA, and cDNA encoding these HCV peptides. The HCV nucleotide embodiments not only include the DNA sequences shown in the sequence listing (e.g., SEQ. ID. NO.: 16) but also include nucleotide sequences encoding the amino acid sequences shown in the sequence listing (e.g., SEQ. ID. NO.: 17) and any nucleotide sequence that hybridizes to the DNA sequences shown in the sequence listing under stringent conditions (e.g., hybridization to filter-bound DNA in 0.5 M NaHPO$_4$, 7.0% sodium dodecyl sulfate (SDS), 1 mM EDTA at 50° C.) and washing in 0.2×SSC/0.2% SDS at 50° C. and any nucleotide sequence that hybridizes to the DNA sequences that encode an amino acid sequence provided in the sequence listing (SEQ. ID. NOs.: 17) under less stringent conditions (e.g., hybridization in 0.5 M NaHPO$_4$, 7.0% sodium dodecyl sulfate (SDS), 1 mM EDTA at 37° C. and washing in 0.2×SSC/0.2% SDS at 37° C.).

The nucleic acid embodiments also include fragments, modifications, derivatives, and variants of the sequences described above. Desired embodiments, for example, include nucleic acids having at least 12 consecutive bases of one of the novel HCV sequences or a sequence complementary thereto and preferred fragments include at least 12 consecutive bases of a nucleic acid encoding the NS3/4A molecule of SEQ. ID. NO.: 17 or a sequence complementary thereto.

In this regard, the nucleic acid embodiments of the invention can have from 12 to approximately 2079 consecutive nucleotides. Some DNA fragments of the invention, for example, include nucleic acids having at least 12-15, 15-20, 20-30, 30-50, 50-100, 100-200, 200-500, 500-1000, 1000-1500, 1500-2079 consecutive nucleotides of SEQ. ID. NO.: 16 or a complement thereof. The nucleic acid embodiments can also be altered by mutation such as substitutions, additions, or deletions. Due to the degeneracy of nucleotide coding sequences, for example, other DNA sequences that encode substantially the same HCV amino acid sequence as depicted in SEQ. ID. NOs: 17 can be used in some embodiments. These include, but are not limited to, nucleic acid sequences encoding all or portions of NS3/4A (SEQ. ID. NO.: 16) or nucleic acids that complement all or part of this sequence that have been altered by the substitution of different codons that encode a functionally equivalent amino acid residue within the sequence, thus producing a silent change, or a functionally non-equivalent amino acid residue within the sequence, thus producing a detectable change.

By using the nucleic acid sequences described above, probes that complement these molecules can be designed and manufactured by oligonucleotide synthesis. Desirable probes comprise a nucleic acid sequence of (SEQ. ID. NO.: 16) that is unique to this HCV isolate. These probes can be used to screen cDNA from patients so as to isolate natural sources of HCV, some of which may be novel HCV sequences in themselves. Screening can be by filter hybridization or by PCR, for example. By filter hybridization, the labeled probe preferably contains at least 15-30 base pairs of the nucleic acid sequence of (SEQ. ID. NO.: 16) that is unique to to this NS3/4A peptide. The hybridization washing conditions used are preferably of a medium to high stringency. The hybridization can be performed in 0.5M NaHPO$_4$, 7.0% sodium dodecyl sulfate (SDS), 1 mM EDTA at 42° C. overnight and washing can be performed in 0.2×SSC/0.2% SDS at 42° C. For guidance regarding such conditions see, for example, Sambrook et al., 1989, *Molecular Cloning, A Laboratory Manual,* Cold Springs Harbor Press, N.Y.; and Ausubel et al., 1989, *Current Protocols in Molecular Biology,* Green Publishing Associates and Wiley Interscience, N.Y., herein expressly incorporated by reference.

HCV nucleic acids can also be isolated from patients infected with HCV using the nucleic acids described herein. (See also Example 6). Accordingly, RNA obtained from a patient infected with HCV is reverse transcribed and the resultant cDNA is amplified using PCR or another amplification technique. The primers are preferably obtained from the NS3/4A sequence (SEQ. ID. NO.: 16).

For a review of PCR technology, see Molecular Cloning to Genetic Engineering, White, B. A. Ed. in *Methods in Molecular Biology* 67: Humana Press, Totowa (1997), the disclosure of which is incorporated herein by reference in its entirety and the publication entitled "PCR Methods and Applications" (1991, Cold Spring Harbor Laboratory Press), the disclosure of which is incorporated herein by reference in its entirety. For amplification of mRNAs, it is within the scope of the invention to reverse transcribe mRNA into cDNA followed by PCR (RT-PCR); or, to use a single enzyme for both steps as described in U.S. Pat. No. 5,322, 770, the disclosure of which is incorporated herein by reference in its entirety. Another technique involves the use of Reverse Transcriptase Asymmetric Gap Ligase Chain Reaction (RT-AGLCR), as described by Marshall R. L. et al. (*PCR Methods and Applications* 4:80-84, 1994), the disclosure of which is incorporated herein by reference in its entirety.

Briefly, RNA is isolated, following standard procedures. A reverse transcription reaction is performed on the RNA using an oligonucleotide primer specific for the most 5' end of the amplified fragment as a primer of first strand synthesis. The resulting RNA/DNA hybrid is then "tailed" with guanines using a standard terminal transferase reaction. The hybrid is then digested with RNAse H, and second strand synthesis is primed with a poly-C primer. Thus, cDNA sequences upstream of the amplified fragment are easily isolated. For a review of cloning strategies which can be used, see e.g., Sambrook et al., 1989, supra.

In each of these amplification procedures, primers on either side of the sequence to be amplified are added to a suitably prepared nucleic acid sample along with dNTPs and a thermostable polymerase, such as Taq polymerase, Pfu polymerase, or Vent polymerase. The nucleic acid in the sample is denatured and the primers are specifically hybridized to complementary nucleic acid sequences in the sample. The hybridized primers are then extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683, 195, 4,683,202 and 4,965,188, the disclosures of which are incorporated herein by reference in their entirety.

The primers are selected to be substantially complementary to a portion of the nucleic acid sequence of (SEQ. ID. NO.: 16) that is unique to this NS3/4A molecule, thereby allowing the sequences between the primers to be amplified. Preferably, primers are at least 16-20, 20-25, or 25-30 nucleotides in length. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers described herein preferably range between 10 and 75%, more preferably between 35 and 60%, and most preferably between 40 and 55%. The appropriate length for primers under a particular set of assay conditions can be empirically determined by one of skill in the art.

The spacing of the primers relates to the length of the segment to be amplified. In the context of the embodiments described herein, amplified segments carrying nucleic acid sequence encoding HCV peptides can range in size from at least about 25 bp to the entire length of the HCV genome. Amplification fragments from 25-1000 bp are typical, fragments from 50-1000 bp are preferred and fragments from 100-600 bp are highly preferred. It will be appreciated that amplification primers can be of any sequence that allows for specific amplification of the NS3/4A region and can, for example, include modifications such as restriction sites to facilitate cloning.

The PCR product can be subcloned and sequenced to ensure that the amplified sequences represent the sequences of an HCV peptide. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library. Additionally, an expression library can be constructed utilizing cDNA synthesized from, for example, RNA isolated from an infected patient. In this manner, HCV geneproducts can be isolated using standard antibody screening techniques in conjunction with antibodies raised against the HCV gene product. (For screening techniques, see, for example, Harlow, E. and Lane, eds., 1988, *Antibodies: A Laboratory Manual,* Cold Spring Harbor Press, Cold Spring Harbor., herein expressly incorporated by reference in its entirety)

Embodiments also include (a) DNA vectors that contain any of the foregoing nucleic acid sequences and/or their complements (i.e., antisense); (b) DNA expression vectors that contain any of the foregoing nucleic acid sequences operatively associated with a regulatory element that directs the expression of the nucleic acid; and (c) genetically engineered host cells that contain any of the foregoing nucleic acid sequences operatively associated with a regulatory element that directs the expression of the coding sequences in the host cell. These recombinant constructs are capable of replicating autonomously in a host cell. Alternatively, the recombinant constructs can become integrated into the chromosomal DNA of a host cell. Such recombinant polynucleotides typically comprise an HCV genomic or cDNA polynucleotide of semi-synthetic or synthetic origin by virtue of human manipulation. Therefore, recombinant nucleic acids comprising these sequences and complements thereof that are not naturally occurring are provided.

Although nucleic acids encoding an HCV peptide or nucleic acids having sequences that complement an HCV gene as they appear in nature can be employed, they will often be altered, e.g., by deletion, substitution, or insertion and can be accompanied by sequence not present in humans. As used herein, regulatory elements include, but are not limited to, inducible and non-inducible promoters, enhancers, operators and other elements known to those skilled in the art that drive and regulate expression. Such regulatory elements include, but are not limited to, the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast_-mating factors.

In addition, recombinant HCV peptide-encoding nucleic acid sequences and their complementary sequences can be engineered so as to modify their processing or expression. For example, and not by way of limitation, the HCV nucleic acids described herein can be combined with a promoter sequence and/or ribosome binding site, or a signal sequence can be inserted upstream of HCV peptide-encoding sequences so as to permit secretion of the peptide and thereby facilitate harvesting or bioavailability. Additionally, a given HCV nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. (See Example 6). Any technique for mutagenesis known in the art can be used, including but not limited to, in vitro site-directed mutagenesis. (Hutchinson et al., *J. Biol. Chem.,* 253:6551 (1978), herein incorporated by reference in its entirety).

Further, nucleic acids encoding other proteins or domains of other proteins can be joined to nucleic acids encoding an HCV peptide so as to create a fusion protein. Nucleotides encoding fusion proteins can include, but are not limited to, a full length NS3/4A sequence (SEQ. ID. NO.: 16), a truncated NS3/4A sequence or a peptide fragment of an NS3/4A sequence fused to an unrelated protein or peptide, such as for example, poly histidine, hemagglutinin, an enzyme, fluorescent protein, or luminescent protein, as discussed below.

Surprisingly, it was discovered that the NS3-pVAX and NS3/4A-pVAX vectors were capable of eliciting a potent immune response when injected into an immunocompetent mammal. The example below describes these experiments in greater detail.

EXAMPLE 7

To determine whether a humoral immune response was elicited by the NS3-pVAX and NS3/4A-pVAX vectors, the expression constructs described in Example 6 were purified using the Qiagen DNA purification system, according to the manufacturer's instructions and the purified DNA vectors were used to immunize groups of four to ten Balb/c mice. The plasmids were injected directly into regenerating tibialis anterior (TA) muscles as previously described (Davis et al., *Human Gene Therapy* 4(6):733 (1993), herein expressly incorporated by reference). In brief, mice were injected intramuscularly with 50 μl/TA of 0.01 mM cardiotoxin (Latoxan, Rosans, France) in 0.9% sterile NaCl. Five days later, each TA muscle was injected with 50 μl PBS containing either rNS3 or DNA.

Inbred mouse strains C57/BL6 (H-2b) Balb/C (H-2d), and CBA (H-2k) were obtained from the breeding facility at Möllegard Denmark, Charles River Uppsala, Sweden, or B&K Sollentuna Sweden. All mice were female and were used at 4-8 weeks of age. For monitoring of humoral responses, all mice received a booster injection of 50 μl/TA of plasmid DNA every fourth week. In addition, some mice were given recombinant NS3 (rNS3) protein, which was purified as described herein. The mice receiving rNS3 were immunized no more than twice. All mice were bled twice a month.

Enzyme immunosorbent assays (EIAs) were used to detect the presence of murine NS3 antibodies. These assays were performed essentially as described in (Chen et al., *Hepatology* 28(1): 219 (1998)). Briefly, rNS3 was passively adsorbed overnight at 4° C. to 96-well microtiter plates (Nunc, Copenhagen, Denmark) at 1 μg/ml in 50 mM sodium carbonate buffer (pH 9.6). The plates were then blocked by incubation with dilution buffer containing PBS, 2% goat serum, and 1% bovine serum albumin for one hour at 37° C. Serial dilutions of mouse sera starting at 1:60 were then incubated on the plates for one hour. Bound murine serum antibodies were detected by an alkaline phosphatase conjugated goat anti-mouse IgG (Sigma Cell Products, Saint Louis, Mo.) followed by addition of the substrate pNPP (1 tablet/5 ml of 1M Diethanol amine buffer with 0.5 mM $MgCl_2$). The reaction was stopped by addition of 1M NaOH and absorbency was read at 405 nm.

Figure 4:
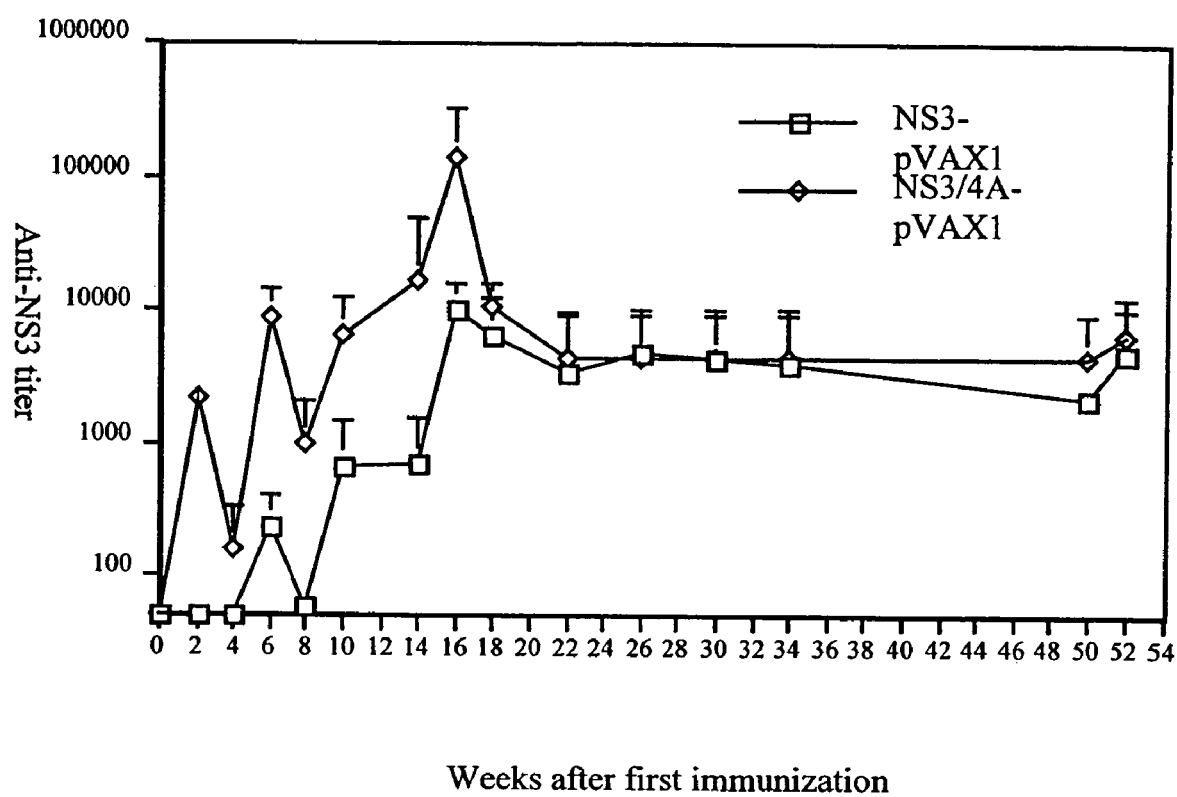
FIG. 4 is a graph showing the antibody titer in H-$2^d$ mice against NS3 as a function of time after the first immunization. Diamonds denote antibody titer in mice immunized with NS3/4A-pVAX and squares denote antibody titer in mice immunized with NS3-pVAX.

After four weeks, four out of five mice immunized with NS3/4A-pVAX had developed NS3 antibodies, whereas one out of five immunized with NS3-pVAX had developed antibodies (FIG. 4). After six weeks, four out of five mice immunized with NS3/4A-pVAX had developed high levels ($>10^4$) of NS3 antibodies (mean levels 10800±4830) and one had a titer of 2160. Although all mice immunized with NS3-pVAX developed NS3 antibodies, none of them developed levels as high as that produced by the NS3/4A-pVAX construct (mean levels 1800±805). The antibody levels elicited by the NS3/4A fusion construct were significantly higher than those induced by NS3-pVAX at six weeks (mean ranks 7.6 v.s 3.4, $p<0.05$, Mann-Whitney rank sum test, and $p<0.01$, Students t-test). Thus, immunization with either NS3-pVAX or NS3/4A-pVAX resulted in the production of anti-NS3 antibodies, but the NS3/4A fusion gene was a more potent immunogen. The example below describes experiments that were performed to determine if the NS3/4A-TPT-pVAX construct could elicit a potent immune response.

EXAMPLE 8

To test if the enhanced immunogenicity of NS3/4A could be solely attributed to the presence of NS4A, or if the NS3/4A fusion protein in addition had to be cleaved at the NS3/4A junction, new experiments were performed. In a first experiment, the immunogenicity of the NS3-pVAX, NS3/4A-pVAX, and NS3/4A-TPT-pVAX vectors were compared in Balb/c mice. Mice were immunised on week 0 as described above, and, after two weeks, all mice were bled and the presence of antibodies to NS3 at a serum dilution of 1:60 was determined (TABLE 11). Mice were bled again on week 4. Although, the NS3/4A-TPT-pVAX vector was comparable to the NS3-pVAX vector (4/10 vs. 0/10; NS, Fisher's exact test), the NS3/4A-pVAX vector continued to be the most potent immunogen. Thus, all of the HCV constructs that were introduced into mice were capable of eliciting an immune response against NS3, however, the NS4A sequence and a functional proteolytic cleavage site between the NS3 and NS4A sequences provided for a more potent immune response.

TABLE 11

| Weeks from 1st immunization | No. of antibody responders to the respective immunogen after one 100 μg i.m immunization | | |
|---|---|---|---|
| | NS3-pVAX | NS3/4A-pVAX | NS3/4A-TPT-pVAX |
| 2 | 0/10 | 17/20 | 4/10 |
| 4 | 0/10 | 20/20 | 10/10 |
| | (<60) | (2415 ± 3715) | (390 ± 639) |
| | | 55% > $10^3$ | 50% > $10^2$ |
| | | 10% > $10^4$ | 10% > $10^3$ |

During the chronic phase of infection, HCV replicates in hepatocytes, and spreads within the liver. A major factor in combating chronic and persistent viral infections is the cell-mediated immune defense system. CD4+ and CD8+ lymphocytes infiltrate the liver during the chronic phase of HCV infection, but they are incapable of clearing the virus or preventing liver damage. In addition, persistent HCV infection is associated with the onset of hepatocellular carcinoma (HCC). The examples below describe experiments that were performed to determine whether the NS3 and NS3/4A construct were capable of eliciting a T-cell mediated immune response against NS3.

EXAMPLE 9

To study whether the constructs described above were capable of eliciting a cell-mediated response against NS3, an in vivo tumor growth assay was perfomed. To this end, an SP2/0 tumor cell line stably transfected with the NS3/4A gene was made. The pcDNA3.1 plasmid containing the NS3/4A gene was linearized by BglII digestion. A total of 5 μg linearized plasmid DNA was mixed with 60 μg transfection reagent (Superfect, Qiagen, Germany) and the mixture was added to a 50% confluent layer of SP2/0 cells in a 35 mm dish. The transfected SP2/0 cells (NS3/4A-SP2/0) were grown for 14 days in the presence of 800 μg/ml geneticin and individual clones were isolated. A stable NS3/4A- expressing SP2/0 clone was identified using PCR and RTPCR. The cloned cell line was maintained in DMEM containing 10% fetal bovine serum, L-glutamine, and penicillin-streptomycin.

The in vivo growth kinetics of the SP2/0 and the NS3/4A-SP2/0 cell lines were then evaluated in Balb/c mice. Mice were injected subcutaneously with 2×10⁶ tumor cells in the right flank. Each day the size of the tumor was determined through the skin. The growth kinetics of the two cell lines was comparable. For example, the mean tumor sizes did not differ between the two cell lines at any time point. (See TABLE 12). The example below describes experiments that were performed to determine whether mice immunized with the NS3/4A constructs had developed a T-cell response against NS3.

TABLE 13

| Mouse ID | Immunogen | Dose (μg) | Tumor cell line | Tumor growth | Maximum tumor size (mm) |
|---|---|---|---|---|---|
| 1 | NS3-pVAX | 100 | SP2/0 | Yes | 5 |
| 2 | NS3-pVAX | 100 | SP2/0 | Yes | 15 |
| 3 | NS3-pVAX | 100 | SP2/0 | No | — |
| 4 | NS3-pVAX | 100 | SP2/0 | Yes | 6 |
| 5 | NS3-pVAX | 100 | SP2/0 | Yes | 13 |
| Group total | | | | 4/5 | 9.75 ± 4.992 |
| 6 | NS3-pVAX | 100 | NS3/4A-SP2/0 | Yes | 9 |
| 7 | NS3-pVAX | 100 | NS3/4A-SP2/0 | Yes | 8 |
| 8 | NS3-pVAX | 100 | NS3/4A-SP2/0 | Yes | 7 |

TABLE 12

| Mouse ID | Tumor cell line | Maximum in vivo tumor size at indicated time point | | | | | | | | |
|---|---|---|---|---|---|---|---|---|---|---|
| | | 5 | 6 | 7 | 8 | 11 | 12 | 13 | 14 | 15 |
| 1 | SP2/0 | 1.6 | 2.5 | 4.5 | 6.0 | 10.0 | 10.5 | 11.0 | 12.0 | 12.0 |
| 2 | SP2/0 | 1.0 | 1.0 | 2.0 | 3.0 | 7.5 | 7.5 | 8.0 | 11.5 | 11.5 |
| 3 | SP2/0 | 2.0 | 5.0 | 7.5 | 8.0 | 11.0 | 11.5 | 12.0 | 12.0 | 13.0 |
| 4 | SP2/0 | 4.0 | 7.0 | 8.0 | 10.0 | 13.0 | 15.0 | 16.5 | 16.5 | 17.0 |
| 5 | SP2/0 | 1.0 | 1.0 | 3.0 | 4.0 | 5.0 | 6.0 | 6.0 | 6.0 | 7.0 |
| Group mean | | 1.92 | 3.3 | 5.0 | 6.2 | 9.3 | 10.1 | 10.7 | 11.6 | 12.1 |
| 6 | NS3/4A-SP2/0 | 1.0 | 2.0 | 3.0 | 3.5 | 4.0 | 5.5 | 6.0 | 7.0 | 8.0 |
| 7 | NS3/4A-SP2/0 | 2.0 | 2.5 | 3.0 | 5.0 | 7.0 | 9.0 | 9.5 | 9.5 | 11.0 |
| 8 | NS3/4A-SP2/0 | 1.0 | 2.0 | 3.5 | 3.5 | 9.5 | 11.0 | 12.0 | 14.0 | 14.0 |
| 9 | NS3/4A-SP2/0 | 1.0 | 1.0 | 2.0 | 6.0 | 11.5 | 13.0 | 14.5 | 16.0 | 18.0 |
| 10 | NS3/4A-SP2/0 | 3.5 | 6.0 | 7.0 | 10.5 | 15.0 | 15.0 | 15.0 | 15.5 | 20.0 |
| Group mean | | 1.7 | 2.7 | 3.7 | 5.7 | 9.4 | 10.7 | 11.4 | 12.4 | 14.2 |
| p-value of student's t-test comparison between group means | | 0.7736 | 0.6918 | 0.4027 | 0.7903 | 0.9670 | 0.7986 | 0.7927 | 0.7508 | 0.4623 |

EXAMPLE 10

To examine whether a T-cell response is elicited by the NS3/4A immunization, the capacity of an immunized mouse's immune defense system to attack the NS3-expressing tumor cell line was assayed. The protocol for testing for in vivo inhibition of tumor growth of the SP2/0 myeloma cell line in Balb/c mice has been described in detail previously (Encke et al., *J. Immunol.* 161:491 7 (1998), herein expressly incorporated by reference in its entirety). Inhibition of tumor growth in this model is dependent on the priming of cytotoxic T lymphocytes (CTLs). Briefly, groups of ten mice were immunized i.m. five times with one month intervals with either 100 μg NS3-pVAX or 100 μg NS3/4A-pVAX. Two weeks after the last immunization 2×10⁶ SP2/0 or NS3/4A-SP2/0 cells were injected into the right flank of each mouse. Two weeks later the mice were sacrificed and the maximum tumor sizes were measured. There was no difference between the mean SP2/0 and NS3/4A-SP2/0 tumor sizes in the NS3-pVAX immunized mice (See TABLE 13).

TABLE 13-continued

| Mouse ID | Immunogen | Dose (μg) | Tumor cell line | Tumor growth | Maximum tumor size (mm) |
|---|---|---|---|---|---|
| 9 | NS3-pVAX | 100 | NS3/4A-SP2/0 | No | — |
| 10 | NS3-pVAX | 100 | NS3/4A-SP2/0 | No | — |
| | | | | 3/5 | 8.00 ± 1.00 |

Note:
Statistical analysis (StatView): Student's t-test on maximum tumor size.
P-values < 0.05 are considered significant.

Unpaired t-test for Max diam
Grouping Variable: Column 1
Hypothesized Difference = 0
Row exclusion: NS3DNA-Tumor-001213

| | Mean Diff. | DF | t-Value | P-Value |
|---|---|---|---|---|
| NS3-sp2, NS3-spNS3 | 1.750 | 5 | 0.58 | 0.584 |

| Group Info for Max diam |
| Grouping Variable: Column 1 |
| Row exclusion: NS3DNA-Tumor-001213 |

| | Count | Mean | Variance | Std. Dev. | Std. Err |
|---|---|---|---|---|---|
| NS3-sp2 | 4 | 9.750 | 24.917 | 4.992 | 2.496 |
| NS3-spNS3 | 3 | 8.000 | 1.000 | 1.000 | 0.57 |

In the next set of experiments, the inhibition of SP2/0 or NS3/4A-SP2/0 tumor growth wa cells. (See TABLE 14). Thus, NS3/4A-pVAX immunization elicits CTLs that inhibit growth of cells expressing NS3/4A in vivo. The example below describes experiments that were performed to analyze the efficiency of various NS3 containing compositions in eliciting a cell-mediated response to NS3.

TABLE 14

| Mouse ID | Immunogen | Dose (µg) | Tumor cell line | Tumor growth | Maximum tumor size (mm) |
|---|---|---|---|---|---|
| 11 | NS3/4A-pVAX | 100 | SP2/0 | No | — |
| 12 | NS3/4A-pVAX | 100 | SP2/0 | Yes | 24 |
| 13 | NS3/4A-pVAX | 100 | SP2/0 | Yes | 9 |
| 14 | NS3/4A-pVAX | 100 | SP2/0 | Yes | 11 |
| 15 | NS3/4A-pVAX | 100 | SP2/0 | Yes | 25 |
| | | | | 4/5 | 17.25 ± 8.421 |
| 16 | NS3/4A-pVAX | 100 | NS3/4A-SP2/0 | No | — |
| 17 | NS3/4A-pVAX | 100 | NS3/4A-SP2/0 | Yes | 9 |
| 18 | NS3/4A-pVAX | 100 | NS3/4A-SP2/0 | Yes | 7 |
| 19 | NS3/4A-pVAX | 100 | NS3/4A-SP2/0 | Yes | 5 |
| 20 | NS3/4A-pVAX | 100 | NS3/4A-SP2/0 | Yes | 4 |
| | | | | 4/5 | 6.25 ± 2.217 |

Note:
Statistical analysis (StatView): Student's t-test on maximum tumor size.
P-values < 0.05 are considered significant.

| Unpaired t-test for Max diam |
| Grouping Variable: Column 1 |
| Hypothesized Difference = 0 |
| Row exclusion: NS3DNA-Tumor-001213 |

| | Mean Diff. | DF | t-Value | P-Value |
|---|---|---|---|---|
| NS3/4-sp2, NS3/4-spNS3 | 11.000 | 6 | 2.526 | 0.044 |

| Group Info for Max diam |
| Grouping Variable: Column 1 |
| Row exclusion: NS3DNA-Tumor-001213 |

| | Count | Mean | Variance | Std. Dev. | Std. Err |
|---|---|---|---|---|---|
| NS3/4-sp2 | 4 | 17.250 | 70.917 | 8.421 | 4.211 |
| NS3/4-spNS3 | 4 | 6.250 | 4.917 | 2.217 | 1.109 |

EXAMPLE 11

To analyze whether administration of different NS3 containing compositions affected the elicitation of a cell-mediated immune response, mice were immunized with PBS, rNS3, irrelevant DNA or the NS3/4A construct, and tumor sizes were determined, as described above. Only the NS3/4A construct was able to elicit a T-cell response sufficient to cause a statistically significant reduction in tumor size (See TABLE 15). The example below describes experiments that were performed to determine whether the reduction in tumor size can be attributed to the generation of NS3-specific T-lymphocytes.

TABLE 15

| Mouse ID | Immunogen | Dose (µg) | Tumor cell line | Anti-NS3 | Tumor growth | Maximum tumor size (mm) |
|---|---|---|---|---|---|---|
| 1 | NS3-pVAX | 10 | NS3/4A-SP2/0 | <60 | + | 12.0 |
| 2 | NS3-pVAX | 10 | NS3/4A-SP2/0 | <60 | + | 20.0 |
| 3 | NS3-pVAX | 10 | NS3/4A-SP2/0 | 60 | + | 18.0 |
| 4 | NS3-pVAX | 10 | NS3/4A-SP2/0 | <60 | + | 13.0 |
| 5 | NS3-pVAX | 10 | NS3/4A-SP2/0 | <60 | + | 17.0 |
| | Group mean | | | 60 | 5/5 | 16.0 ± 3.391 |
| 6 | NS3-pVAX | 100 | NS3/4A-SP2/0 | 2160 | + | 10.0 |
| 7 | NS3-pVAX | 100 | NS3/4A-SP2/0 | <60 | − | — |
| 8 | NS3-pVAX | 100 | NS3/4A-SP2/0 | <60 | − | — |
| 9 | NS3-pVAX | 100 | NS3/4A-SP2/0 | 360 | − | — |
| 10 | NS3-pVAX | 100 | NS3/4A-SP2/0 | <60 | + | 12.5 |
| | Group mean | | | 1260 | 2/5 | 11.25 ± 1.768 |
| 11 | NS3/4A-pVAX | 10 | NS3/4A-SP2/0 | <60 | + | 10.0 |
| 12 | NS3/4A-pVAX | 10 | NS3/4A-SP2/0 | <60 | − | — |
| 13 | NS3/4A-pVAX | 10 | NS3/4A-SP2/0 | <60 | − | — |
| 14 | NS3/4A-pVAX | 10 | NS3/4A-SP2/0 | <60 | + | 13.0 |
| 15 | NS3/4A-pVAX | 10 | NS3/4A-SP2/0 | <60 | + | 13.5 |
| | Group mean | | | <60 | 3/5 | 12.167 ± 1.893 |
| 16 | NS3/4A-pVAX | 100 | NS3/4A-SP2/0 | 60 | + | 10.0 |
| 17 | NS3/4A-pVAX | 100 | NS3/4A-SP2/0 | 360 | − | — |
| 18 | NS3/4A-pVAX | 100 | NS3/4A-SP2/0 | 2160 | + | 8.0 |
| 19 | NS3/4A-pVAX | 100 | NS3/4A-SP2/0 | 2160 | + | 12.0 |
| 20 | NS3/4A-pVAX | 100 | NS3/4A-SP2/0 | 2160 | + | 7.0 |
| | Group mean | | | 1380 | 4/5 | 9.25 ± 2.217 |
| 36 | p17-pcDNA3 | 100 | NS3/4A-SP2/0 | <60 | + | 20.0 |
| 37 | p17-pcDNA3 | 100 | NS3/4A-SP2/0 | <60 | + | 7.0 |

TABLE 15-continued

| Mouse ID | Immunogen | Dose (μg) | Tumor cell line | Anti-NS3 | Tumor growth | Maximum tumor size (mm) |
|---|---|---|---|---|---|---|
| 38 | p17-pcDNA3 | 100 | NS3/4A-SP2/0 | <60 | + | 11.0 |
| 39 | p17-pcDNA3 | 100 | NS3/4A-SP2/0 | <60 | + | 15.0 |
| 40 | p17-pcDNA3 | 100 | NS3/4A-SP2/0 | <60 | + | 18.0 |
| | Group mean | | | <60 | 5/5 | 14.20 ± 5.263 |
| 41 | rNS3/CFA | 20 | NS3/4A-SP2/0 | >466560 | + | 13.0 |
| 42 | rNS3/CFA | 20 | NS3/4A-SP2/0 | >466560 | − | — |
| 43 | rNS3/CFA | 20 | NS3/4A-SP2/0 | >466560 | + | 3.5 |
| 44 | rNS3/CFA | 20 | NS3/4A-SP2/0 | >466560 | + | 22.0 |
| 45 | rNS3/CFA | 20 | NS3/4A-SP2/0 | >466560 | + | 17.0 |
| | Group mean | | | 466560 | 4/5 | 17.333 ± 4.509 |
| 46 | PBS | — | NS3/4A-SP2/0 | <60 | + | 10.0 |
| 47 | PBS | — | NS3/4A-SP2/0 | <60 | + | 16.5 |
| 48 | PBS | — | NS3/4A-SP2/0 | 60 | + | 15.0 |
| 49 | PBS | — | NS3/4A-SP2/0 | <60 | + | 21.0 |
| 50 | PBS | — | NS3/4A-SP2/0 | <60 | + | 15.0 |
| 51 | PBS | — | NS3/4A-SP2/0 | <60 | − | — |
| | Group mean | | | 60 | 5/6 | 15.50 ± 3.937 |

Note:
Statistical analysis (StatView): Student's t-test on maximum tumor size.
P-values < 0.05 are considered as significant.

| Unpaired t-test for Largest Tumor size Grouping Variable: group Hypothesized Difference = 0 | | | |
|---|---|---|---|
| | Mean Diff. | DF | t-Value | P-Value |
| p17-sp3-4, NS3-100-sp3-4 | 2.950 | 5 | .739 | .4933 |
| p17-sp3-4, NS3/4-10-sp3-4 | 2.033 | 6 | .628 | .5532 |
| p17-sp3-4, NS3-10-sp3-4 | −1.800 | 8 | −.643 | .5383 |
| p17-sp3-4, NS3/4-100-sp3-4 | 4.950 | 7 | 1.742 | .1250 |
| p17-sp3-4, PBS-sp3-4 | −1.300 | 8 | −.442 | .6700 |
| p17-sp3-4, rNS3-sp3-4 | −3.133 | 6 | −.854 | .4259 |
| NS3-100-sp3-4, NS3/4-10-sp3-4 | −.917 | 3 | −.542 | .6254 |
| NS3-100-sp3-4, NS3-10-sp3-4 | −4.750 | 5 | −1.811 | .1299 |
| NS3-100-sp3-4, NS3/4-100-sp3-4 | 2.000 | 4 | 1.092 | .3360 |
| NS3-100-sp3-4, PBS-sp3-4 | −4.250 | 5 | −1.408 | .2183 |
| NS3-100-sp3-4, rNS3-sp3-4 | −6.083 | 3 | −1.744 | .1795 |
| NS3/4-10-sp3-4, NS3-10-sp3-4 | −3.833 | 6 | −1.763 | .1283 |
| NS3/4-10-sp3-4, NS3/4-100-sp3-4 | 2.917 | 5 | 1.824 | .1277 |
| NS3/4-10-sp3-4, PBS-sp3-4 | −3.333 | 6 | −1.344 | .2274 |
| NS3/4-10-sp3-4, rNS3-sp3-4 | −5.167 | 4 | −1.830 | .1412 |
| NS3-10-sp3-4, NS3/4-100-sp3-4 | 6.750 | 7 | 3.416 | .0112 |
| NS3-10-sp3-4, PBS-sp3-4 | .500 | 8 | .215 | .8350 |
| NS3-10-sp3-4, rNS3-sp3-4 | −1.333 | 6 | −.480 | .6480 |
| NS3/4-100-sp3-4, PBS-sp3-4 | −6.250 | 7 | −2.814 | .0260 |
| NS3/4-100-sp3-4, rNS3-sp3-4 | −8.083 | 5 | −3.179 | .0246 |
| PBS-sp3-4, rNS3-sp3-4 | −1.833 | 6 | −.607 | .5662 |

EXAMPLE 12

Figure 5:
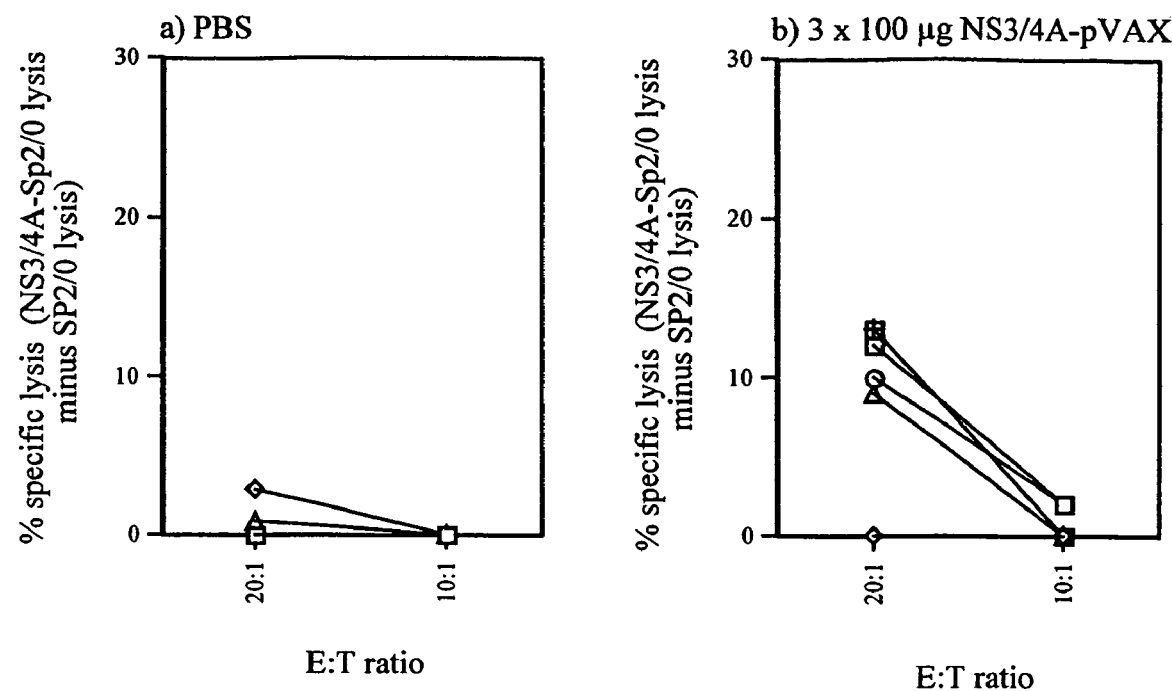
FIG. 5A is a graph showing the percentage of specific CTL-mediated lysis of SP2/0 target cells as a function of the effector to target ratio. Phosphate Buffered Saline (PBS) was used as a control immunogen.
FIG. 5B Is a graph showing the percentage specific CTL-mediated lysis of SP2/0 target cells as a function of the effector to target ratio. Plasmid NS3/4A-pVAX was used as the immunogen.

To determine whether NS3-specific T-cells were elicited by the NS3/4A immunizations, an in vitro T-cell mediated tumor cell lysis assay was employed. The assay has been described in detail previously (Townsend et al. *J. Virol.* 71:3365 (1997), herein expressly incorporated by reference in its entirety). Briefly, groups of five Balb/c mice were immunized three times with 100 μg NS3/4A-pVAX i.m. Two weeks after the last injection the mice were sacrificed and splenocytes were harvested. Re-stimulation cultures with $3 \times 10^6$ splenocytes and $3 \times 10^6$ NS3/4A-SP2/0 cells were set. After five days, a standard $Cr^{51}$-release assay was performed using NS3/4A-SP2/0 or SP2/0 cells as targets. Percent specific lysis was calculated as the ratio between lysis of NS3/4A-SP2/0 cells and lysis of SP2/0 cells. Only mice immunized with NS3/4A-pVAX displayed specific lysis over 10% in four out of five tested mice, using an effector to target ratio of 20:1 (See FIGS. 5A and B). Accordingly, mice immunized with NS3/4A exhibited a reduction in cancer cell proliferation and/or NS3/4A caused the lysis of cancer cells. The section below describes several of the embodied HCV polypeptides in greater detail.

HCV Peptides

The nucleic acids encoding the HCV peptides, described in the previous section, can be manipulated using conventional techniques in molecular biology so as to create recombinant constructs that express the HCV peptides. The embodied HCV peptides or derivatives thereof, include but are not limited to, those containing as a primary amino acid sequence all of the amino acid sequence substantially as depicted in the Sequence Listing (SEQ. ID. NOs.: 17, 29-32 and 43-49) and fragments thereof at least four amino acids in length (e.g., SEQ. ID. NOs.: 25-27, and 33-42) including altered sequences in which functionally equivalent amino acid residues are substituted for residues within the sequence resulting in a silent change. Preferred fragments of a sequence of SEQ. ID. NOs.: 17, 29-32 and 43-49 are at least four amino acids and comprise amino acid sequence unique to the discovered NS3/4A peptide (SEQ. ID. NO.: 17) including altered sequences in which functionally equivalent amino acid residues are substituted for residues within the sequence resulting in a silent change. The HCV peptides can be, for example, at least 12-15, 15-20, 20-25, 25-50, 50-100, 100-150, 150-250, 250-500 or 500-704 amino acids in length. Other fragments (e.g., SEQ. ID. NOs.: 25-27, and 33-42) are also aspects of the invention.

Embodiments of the invention also include HCV peptides that are substantially identical to those described above. That is, HCV peptides that have one or more amino acid residues within SEQ. ID. NO.: 17 and fragments thereof that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

The HCV peptides described herein can be prepared by chemical synthesis methods (such as solid phase peptide synthesis) using techniques known in the art such as those set forth by Merrifield et al., *J. Am. Chem. Soc.* 85:2149 (1964), Houghten et al., *Proc. Natl. Acad. Sci. USA*, 82:51: 32 (1985), Stewart and Young (*Solid phase peptide synthesis*, Pierce Chem Co., Rockford, Ill. (1984), and Creighton, 1983, *Proteins: Structures and Molecular Principles*, W. H. Freeman & Co., N.Y., herein expressly incorporated by reference. Such polypeptides can be synthesized with or without a methionine on the amino terminus. Chemically synthesized HCV peptides can be oxidized using methods set forth in these references to form disulfide bridges.

While the HCV peptides described herein can be chemically synthesized, it can be more effective to produce these polypeptides by recombinant DNA technology. Such methods can be used to construct expression vectors containing the HCV nucleotide sequences described above, for example, and appropriate transcriptional and translational control signals. These methods include, for example, in vitro recombinant DNA techniques, synthetic techniques, and in vivo genetic recombination. Alternatively, RNA capable of encoding HCV nucleotide sequences can be chemically synthesized using, for example, synthesizers. See, for example, the techniques described in *Oligonucleotide Synthesis*, 1984, Gait, M. J. ed., IRL Press, Oxford, which is incorporated by reference herein in its entirety. Accordingly, several embodiments concern cell lines that have been engineered to express the embodied HCV peptides. For example, some cells are made to express the HCV peptides of (SEQ. ID. NOs.: 17, 29-32 and 43-49) or fragments of these molecules.

A variety of host-expression vector systems can be utilized to express the embodied HCV peptides. Suitable expression systems include, but are not limited to, microorganisms such as bacteria (e.g., *E. coli* or *B. subtilis*) transformed with recombinant bacteriophage DNA, plasmid DNA or cosmid DNA expression vectors containing HCV nucleotide sequences; yeast (e.g., *Saccharomyces, Pichia*) transformed with recombinant yeast expression vectors containing the HCV nucleotide sequences; insect cell systems infected with recombinant virus expression vectors (e.g., baculovirus) containing the HCV sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HCV sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the HCV gene product being expressed. For example, when a large quantity of such a protein is to be produced, for the generation of pharmaceutical compositions of HCV peptide or for raising antibodies to the HCV peptide, for example, vectors which direct the expression of high levels of fusion protein products that are readily purified can be desirable. Such vectors include, but are not limited, to the *E. coli* expression vector pUR278 (Ruther et al., *EMBO J.*, 2:1791 (1983), in which the HCV coding sequence can be ligated individually into the vector in frame with the lacZ coding region so that a fusion protein is produced; pIN vectors (Inouye & Inouye, *Nucleic Acids Res.*, 13:3101-3109 (1985); Van Heeke & Schuster, *J. Biol. Chem.*, 264: 5503-5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The HCV coding sequence can be cloned individually into non-essential regions (for example the polyhedrin gene) of the virus and placed under control of an AcNPV promoter (for example the polyhedrin promoter). Successful insertion of an HCV gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (See e.g., Smith et al., *J. Virol.* 46: 584 (1983); and Smith, U.S. Pat. No. 4,215,051, herein expressly incorporated by reference in their entirety).

In mammalian host cells, a number of viral-based expression systems can be utilized. In cases where an adenovirus is used as an expression vector, the HCV nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the HCV gene product in infected hosts. (See e.g., Logan & Shenk, *Proc. Natl. Acad. Sci. USA* 81:3655-3659 (1984)). Specific initiation signals can also be required for efficient translation of inserted HCV nucleotide sequences. These signals include the ATG initiation codon and adjacent sequences.

However, in cases where only a portion of the HCV coding sequence is inserted, exogenous translational control signals, including, perhaps, the ATG initiation codon, can be provided. Furthermore, the initiation codon can be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See Bittner et al., *Methods in Enzymol.*, 153:516-544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products are important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, and W138.

For long-term, high-yield production of recombinant proteins, stable expression is preferred. For example, cell lines that stably express the HCV peptides described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the HCV gene product.

A number of selection systems can be used, including but not limited to the herpes simplex virus thymidine kinase (Wigler, et al., *Cell* 11:223 (1977), hypoxanthine-guanine phosphoribosyltransferase (Szybalska & Szybalski, *Proc. Natl. Acad. Sci. USA* 48:2026 (1962), and adenine phosphoribosyltransferase (Lowy, et al., *Cell* 22:817 (1980) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980); O'Hare, et al., *Proc. Natl. Acad. Sci. USA* 78:1527 (1981); gpt, which confers resistance to mycophenolic acid (Mulligan & Berg, *Proc. Natl. Acad. Sci. USA* 78:2072 (1981); neo, which confers resistance to the aminoglycoside G-418 (Colberre-Garapin, et al., *J. Mol. Biol.* 150:1 (1981); and hygro, which confers resistance to hygromycin (Santerre, et al., *Gene* 30:147 (1984)).

Alternatively, any fusion protein can be readily purified by utilizing an antibody specific for the fusion protein being expressed. For example, a system described by Janknecht et al. allows for the ready purification of non-denatured fusion proteins expressed in human cell lines. (Janknecht, et al., *Proc. Natl. Acad. Sci. USA* 88: 8972-8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. The example below describes a method that was used to express the HCV peptides encoded by the embodied nucleic acids.

EXAMPLE 13

To characterize the NS3/4A fusion protein, and the truncated and mutated versions thereof, the vector constructs, described in Example 6, were transcribed and translated in vitro, and the resulting polypeptides were visualized by sodium dodecyl sulfate-polyacrylamide gel electrophoresis (SDS-PAGE). In vitro transcription and translation were performed using the T7 coupled reticulocyte lysate system (Promega, Madison, Wis.) according to the manufacturer's instructions. All in vitro translation reactions of the expression constructs were carried out at 30° C. with $^{35}$S-labeled methionine (Amersham International, Plc, Buckinghamshire, UK). The labeled proteins were separated on 12% SDS-PAGE gels and visualized by exposure to X-ray film (Hyper Film-MP, Amersham) for 6-18 hours.

The in vitro analysis revealed that all proteins were expressed to high amounts from their respective expression constructs. The rNS3 construct (NS3-pVAX vector) produced a single peptide of approximately 61 kDa, whereas, the TPT construct (NS3/4A-TPT-pVAX) and the RGT construct (NS3/4A-RGT-pVAX) produced a single polypeptide of approximately 67 kDa, which is identical to the molecular weight of the uncleaved NS3/4A peptide produced from the NS3/4A-pVAX construct. The cleaved product produced from the expressed NS3/4A peptide was approximately 61 kDa, which was identical in size to the rNS3 produced from the NS3-pVAX vector. These results demonstrated that the expression constructs were functional, the NS3/4A construct was enzymatically active, the rNS3 produced a peptide of the predicted size, and the TPT and RGT mutations completely abolished cleavage at the NS3-NS4A junction.

The sequences, constructs, vectors, clones, and other materials comprising the embodied HCV nucleic acids and peptides can be in enriched or isolated form. As used herein, "enriched" means that the concentration of the material is at least about 2, 5, 10, 100, or 1000 times its natural concentration (for example), advantageously 0.01%, by weight, preferably at least about 0.1% by weight. Enriched preparations from about 0.5%, 1%, 5%, 10%, and 20% by weight are also contemplated. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated.

The HCV gene products described herein can also be expressed in plants, insects, and animals so as to create a transgenic organism. Desirable transgenic plant systems having an HCV peptide include *Arabadopsis*, maize, and *Chlamydomonas*. Desirable insect systems having an HCV peptide include, but are not limited to, *D. melanogaster* and *C. elegans*. Animals of any species, including, but not limited to, amphibians, reptiles, birds, mice, hamsters, rats, rabbits, guinea pigs, pigs, micro-pigs, goats, dogs, cats, and non-human primates, e.g., baboons, monkeys, and chimpanzees can be used to generate transgenic animals having an embodied HCV molecule. These transgenic organisms desirably exhibit germline transfer of HCV peptides described herein.

Any technique known in the art is preferably used to introduce the HCV transgene into animals to produce the founder lines of transgenic animals or to knock out or replace existing HCV genes. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al.,

*Proc. Natl. Acad. Sci., USA* 82:6148-6152 (1985); gene targeting in embryonic stem cells (Thompson et al., *Cell* 56:313-321 (1989); electroporation of embryos (Lo, *Mol Cell. Biol.* 3:1803-1814 (1983); and sperm-mediated gene transfer (Lavitrano et al., *Cell* 57:717-723 (1989); see also Gordon, *Transgenic Animals, Intl. Rev. Cytol.* 115:171-229 (1989), all references are hereby incorporated by reference herein in their entirety. The section below describes the manufacture of antibodies that interact with the HCV peptides described herein.

Anti-HCV Antibodies

Following synthesis or expression and isolation or purification of the HCV peptides, the isolated or purified peptide can be used to generate antibodies. Depending on the context, the term "antibodies" can encompass polyclonal, monoclonal, chimeric, single chain, Fab fragments and fragments produced by a Fab expression library. Antibodies that recognize the HCV peptides have many uses including, but not limited to, biotechnological applications, therapeutic/prophylactic applications, and diagnostic applications.

For the production of antibodies, various hosts including goats, rabbits, rats, mice, and humans etc. can be immunized by injection with an HCV peptide. Depending on the host species, various adjuvants can be used to increase immunological response. Such adjuvants include, but are not limited to, ribavirin, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are also potentially useful adjuvants.

Peptides used to induce specific antibodies can have an amino acid sequence consisting of at least four amino acids, and preferably at least 10 to 15 amino acids. By one approach, short stretches of amino acids encoding fragments of NS3/4A are fused with those of another protein such as keyhole limpet hemocyanin such that an antibody is produced against the chimeric molecule. Additionally, a composition comprising ribavirin and NS3/4A (SEQ. ID. NO.: 17), a fragment thereof at least 4, 6, 8, 10, 12, 15, or 20 amino acids in length, or a nucleic acid encoding one or more of these moleucles is administered to an animal. While antibodies capable of specifically recognizing HCV can be generated by injecting synthetic 3-mer, 10-mer, and 15-mer peptides that correspond to an HCV peptide into mice, a more diverse set of antibodies can be generated by using recombinant HCV peptides, prepared as described above.

To generate antibodies to an HCV peptide, substantially pure peptide is isolated from a transfected or transformed cell. The concentration of the peptide in the final preparation is adjusted, for example, by concentration on an Amicon filter device, to the level of a few micrograms/ml. Monoclonal or polyclonal antibody to the peptide of interest can then be prepared as follows:

Monoclonal antibodies to an HCV peptide can be prepared using any technique that provides for the production of antibody molecules by continuous cell lines in culture. These include, but are not limited to, the hybridoma technique originally described by Koehler and Milstein (*Nature* 256:495-497 (1975), the human B-cell hybridoma technique (Kosbor et al. *Immunol Today* 4:72 (1983); Cote et al *Proc Natl Acad Sci* 80:2026-2030 (1983), and the EBV-hybridoma technique Cole et al. *Monoclonal Antibodies and Cancer Therapy,* Alan R. Liss Inc, New York N.Y., pp 77-96 (1985). In addition, techniques developed for the production of "chimeric antibodies", the splicing of mouse antibody genes to human antibody genes to obtain a molecule with appropriate antigen specificity and biological activity can be used. (Morrison et al. *Proc Natl Acad Sci* 81:6851-6855 (1984); Neuberger et al. Nature 312:604-608(1984); Takeda et al. *Nature* 314:452-454(1985). Alternatively, techniques described for the production of single chain antibodies (U.S. Pat. No. 4,946,778) can be adapted to produce HCV-specific single chain antibodies. Antibodies can also be produced by inducing in vivo production in the lymphocyte population or by screening recombinant immunoglobulin libraries or panels of highly specific binding reagents as disclosed in Orlandi et al., *Proc Natl Acad Sci* 86: 3833-3837 (1989), and Winter G. and Milstein C; *Nature* 349:293-299 (1991).

Antibody fragments that contain specific binding sites for an HCV peptide can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity. (Huse W. D. et al. *Science* 256:1275-1281 (1989)).

By one approach, monoclonal antibodies to an HCV peptide are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections are given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of HCV in biological samples). The section below describes some of the diagnostic embodiments in greater detail.

Diagnostic Embodiments

Generally, the embodied diagnostics are classified according to whether a nucleic acid or protein-based assay is used. Some diagnostic assays detect the presence or absence of an embodied HCV nucleic acid sequence in a sample obtained from a patient, whereas, other assays seek to identify whether an embodied HCV peptide is present in a biological sample obtained from a patient. Additionally, the manufacture of kits that incorporate the reagents and methods described herein that allow for the rapid detection and identification of HCV are also embodied. These diagnostic kits can include, for example, an embodied nucleic acid probe or antibody, which specifically detects HCV. The detection component of these kits will typically be supplied in combination with one or more of the following reagents. A support capable of absorbing or otherwise binding DNA, RNA, or protein will often be supplied. Available supports include membranes of nitrocellulose, nylon or derivatized nylon that can be characterized by bearing an array of positively charged substituents. One or more restriction enzymes, control reagents, buffers, amplification enzymes, and non-human polynucleotides like calf-thymus or salmon-sperm DNA can be supplied in these kits.

Useful nucleic acid-based diagnostics include, but are not limited to, direct DNA sequencing, Southern Blot analysis, dot blot analysis, nucleic acid amplification, and combinations of these approaches. The starting point for these analysis is isolated or purified nucleic acid from a biological sample obtained from a patient suspected of contracting HCV or a patient at risk of contracting HCV. The nucleic acid is extracted from the sample and can be amplified by RT-PCR and/or DNA amplification using primers that correspond to regions flanking the embodied HCV nucleic acid sequences (e.g., NS3/4A (SEQ. ID. NO.: 16)).

In some embodiments, nucleic acid probes that specifically hybridize with HCV sequences are attached to a support in an ordered array, wherein the nucleic acid probes are attached to distinct regions of the support that do not overlap with each other. Preferably, such an ordered array is designed to be "addressable" where the distinct locations of the probe are recorded and can be accessed as part of an assay procedure. These probes are joined to a support in different known locations. The knowledge of the precise location of each nucleic acid probe makes these "addressable" arrays particularly useful in binding assays. The nucleic acids from a preparation of several biological samples are then labeled by conventional approaches (e.g., radioactivity or fluorescence) and the labeled samples are applied to the array under conditions that permit hybridization.

If a nucleic acid in the samples hybridizes to a probe on the array, then a signal will be detected at a position on the support that corresponds to the location of the hybrid. Since the identity of each labeled sample is known and the region of the support on which the labeled sample was applied is known, an identification of the presence of the polymorphic variant can be rapidly determined. These approaches are easily automated using technology known to those of skill in the art of high throughput diagnostic or detection analysis.

Additionally, an opposite approach to that presented above can be employed. Nucleic acids present in biological samples can be disposed on a support so as to create an addressable array. Preferably, the samples are disposed on the support at known positions that do not overlap. The presence of HCV nucleic acids in each sample is determined by applying labeled nucleic acid probes that complement nucleic acids, which encode HCV peptides, at locations on the array that correspond to the positions at which the biological samples were disposed. Because the identity of the biological sample and its position on the array is known, the identification of a patient that has been infected with HCV can be rapidly determined. These approaches are also easily automated using technology known to those of skill in the art of high throughput diagnostic analysis.

Any addressable array technology known in the art can be employed. One particular embodiment of polynucleotide arrays is known as Genechips™, and has been generally described in U.S. Pat. No. 5,143,854; PCT publications WO 90/15070 and 92/10092, all of which are herein expressly incorporated by reference in their entireties. These arrays are generally produced using mechanical synthesis methods or light directed synthesis methods, which incorporate a combination of photolithographic methods and solid phase oligonucleotide synthesis. (Fodor et al., *Science*, 251:767-777, (1991)). The immobilization of arrays of oligonucleotides on solid supports has been rendered possible by the development of a technology generally identified as "Very Large Scale Immobilized Polymer Synthesis" (VLSPIS™) in which, typically, probes are immobilized in a high density array on a solid surface of a chip. Examples of VLSPIS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques, all of which are herein expressly incorporated by reference in their entireties. In designing strategies aimed at providing arrays of nucleotides immobilized on solid supports, further presentation strategies were developed to order and display the oligonucleotide arrays on the chips in an attempt to maximize hybridization patterns and diagnostic information. Examples of such presentation strategies are disclosed in PCT Publications WO 94/12305, WO 94/11530, WO 97/29212, and WO 97/31256, all of which are herein expressly incorporated by reference in their entireties.

A wide variety of labels and conjugation techniques are known by those skilled in the art and can be used in various nucleic acid assays. There are several ways to produce labeled nucleic acids for hybridization or PCR including, but not limited to, oligolabeling, nick translation, end-labeling, or PCR amplification using a labeled nucleotide. Alternatively, a nucleic acid encoding an HCV peptide can be cloned into a vector for the production of an mRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

The presence of an HCV peptide in a protein sample obtained from a patient can also be detected by using conventional assays and the embodiments described herein. For example, antibodies that are immunoreactive with the disclosed HCV peptides can be used to screen biological samples for the presence of HCV infection. In preferred embodiments, antibodies that are reactive to the embodied HCV peptides are used to immunoprecipitate the disclosed HCV peptides from biological samples or are used to react with proteins obtained from a biological sample on Western or Immunoblots. Favored diagnostic embodiments also include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies specific for the disclosed HCV peptides. Exemplary sandwich assays are described by David et al., in U.S. Pat. Nos. 4,376,110 and 4,486,530, hereby incorporated by reference. Other embodiments employ aspects of the immune-strip technology disclosed in U.S. Pat. Nos. 5,290,678; 5,604,105; 5,710,008; 5,744,358; and 5,747,274, herein incorporated by reference.

In another preferred protein-based diagnostic, the antibodies described herein are attached to a support in an ordered array, wherein a plurality of antibodies are attached to distinct regions of the support that do not overlap with each other. As with the nucleic acid-based arrays, the protein-based arrays are ordered arrays that are designed to be "addressable" such that the distinct locations are recorded and can be accessed as part of an assay procedure. These probes are joined to a support in different known locations. The knowledge of the precise location of each probe makes these "addressable" arrays particularly useful in binding assays. For example, an addressable array can comprise a support having several regions to which are joined a plurality of antibody probes that specifically recognize HCV peptides present in a biological sample and differentiate the isotype of HCV identified herein.

By one approach, proteins are obtained from biological samples and are then labeled by conventional approaches (e.g., radioactivity, calorimetrically, or fluorescently). The labeled samples are then applied to the array under conditions that permit binding. If a protein in the sample binds to an antibody probe on the array, then a signal will be detected at a position on the support that corresponds to the location of the antibody-protein complex. Since the identity of each labeled sample is known and the region of the support on which the labeled sample was applied is known, an identification of the presence, concentration, and/or expression level can be rapidly determined. That is, by employing labeled standards of a known concentration of HCV peptide, an investigator can accurately determine the protein concentration of the particular peptide in a tested sample and can also assess the expression level of the HCV peptide. Conventional methods in densitometry can also be used to more accurately determine the concentration or expression level of the HCV peptide. These approaches are easily automated using technology known to those of skill in the art of high throughput diagnostic analysis.

In another embodiment, an opposite approach to that presented above can be employed. Proteins present in biological samples can be disposed on a support so as to create an addressable array. Preferably, the protein samples are disposed on the support at known positions that do not overlap. The presence of an HCV peptide in each sample is then determined by applying labeled antibody probes that recognize epitopes specific for the HCV peptide. Because the identity of the biological sample and its position on the array is known, an identification of the presence, concentration, and/or expression level of an HCV peptide can be rapidly determined.

That is, by employing labeled standards of a known concentration of HCV peptide, an investigator can accurately determine the concentration of peptide in a sample and from this information can assess the expression level of the peptide. Conventional methods in densitometry can also be used to more accurately determine the concentration or expression level of the HCV peptide. These approaches are also easily automated using technology known to those of skill in the art of high throughput diagnostic analysis. As detailed above, any addressable array technology known in the art can be employed. The section below describes some of the compositions that can have one or more of the embodied HCV nucleic acids or HCV peptides.

Compositions Comprising the Embodied HCV Nucleic Acids or Peptides

Some embodiments contain at least one of the HCV nucleic acids or peptides joined to a support. Preferably, these supports are manufactured so as to create a multimeric agent. These multimeric agents provide the HCV peptide or nucleic acid in such a form or in such a way that a sufficient affinity to the molecule is achieved. A multimeric agent having an HCV nucleic acid or peptide can be obtained by joining the desired molecule to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An HCV nucleic acid or peptide can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the HCV nucleic acid or peptide by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, HCV nucleic acid or peptide can be covalently bound to carriers including proteins and oligo/polysaccarides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the HCV nucleic acid or peptide. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Colo.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042-1045 (1995)). For some embodiments, a "naked" carrier (i.e., lacking an attached HCV nucleic acid or peptide) that has the capacity to attach an HCV nucleic acid or peptide in the body of a organism is administered. By this approach, a "prodrug-type" therapy is envisioned in which the naked carrier is administered separately from the HCV nucleic acid or peptide and, once both are in the body of the organism, the carrier and the HCV nucleic acid or peptide are assembled into a multimeric complex.

The insertion of linkers, such as linkers (e.g., "λ linkers" engineered to resemble the flexible regions of λ phage) of an appropriate length between the HCV nucleic acid or peptide and the support are also contemplated so as to encourage greater flexibility of the HCV peptide, hybrid, or binding partner and thereby overcome any steric hindrance that can be presented by the support. The determination of an appropriate length of linker that allows for an optimal cellular response or lack thereof, can be determined by screening the HCV nucleic acid or peptide with varying linkers in the assays detailed in the present disclosure.

A composite support comprising more than one type of HCV nucleic acid or peptide is also envisioned. A "composite support" can be a carrier, a resin, or any macromolecular structure used to attach or immobilize two or more different HCV nucleic acids or peptides. As above, the insertion of linkers, such as λ linkers, of an appropriate length between the HCV nucleic acid or peptide and the support is also contemplated so as to encourage greater flexibility in the molecule and thereby overcome any steric hindrance that can occur. The determination of an appropriate length of linker that allows for an optimal cellular response or lack thereof, can be determined by screening the HCV nucleic acid or peptide with varying linkers in the assays detailed in the present disclosure.

In other embodiments, the multimeric and composite supports discussed above can have attached multimerized HCV nucleic acids or peptides so as to create a "multimerized-multimeric support" and a "multimerized-composite support", respectively. A multimerized ligand can, for example, be obtained by coupling two or more HCV nucleic acids or peptides in tandem using conventional techniques in molecular biology. The multimerized form of the HCV nucleic acid or peptide can be advantageous for many applications because of the ability to obtain an agent with a higher affinity, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized HCV nucleic acid or peptide and the support can encourage greater flexibility and limit steric hindrance presented by the support. The determination of an appropriate length of linker can be determined by screening the HCV nucleic acids or peptides in the assays detailed in this disclosure.

Embodiments of the invention also include genetic vaccines, as described above. Preferably these compositions contain ribavirin and a nucleic acid encoding NS3/4A (SEQ. ID. NO.: 17), NS3 (SEQ. ID. NO.: 29), or a mutant (e.g., SEQ. ID. NOs.: 30-32 and 43-49) or a fragment thereof (e.g., SEQ. ID. NOs.: 25-27, and 33-42). The following example describes the preparation of a genetic vaccine suitable for use in humans.

EXAMPLE 14

An HCV expression plasmid is designed to express the NS3/4A peptide. The NS3/4A coding sequence of NS3/4A-pVAX is removed by digestion with EcoRI and XbaI, and the isolated fragment is inserted into plasmid A so that it is under the transcriptional control of the CMV promoter and the RSV enhancer element. (See U.S. Pat. No. 6,235,888 to Pachuk, et al., herein expressly incorporated by reference in its entirety). Plasmid backbone A is 3969 base pairs in length; it contains a PBR origin of replication for replicating in *E. coli* and a kanamycin resistance gene. Inserts such as the NS3/4A, are cloned into a polylinker region, which places the insert between and operably linked to the promoter and polyadenylation signal. Transcription of the cloned inserts is under the control of the CMV promoter and the RSV enhancer elements. A polyadenylation signal is provided by the presence of an SV40 poly A signal situated just 3' of the cloning site. An NS3/4A containing vaccine composition is then made by mixing 500 μg of the rNS3/4A construct with 1 mg of ribavirin.

Said vaccine composition can be used to raise antibodies in a mammal (e.g., mice or rabbits) or can be injected intramuscularly into a human so as to to raise antibodies, preferably a human that is chronically infected with the HCV virus. The recipient preferably receives three immunization boosts of the mixture at 4-week intervals, as well. By the third boost, the titer of antibody specific for HCV will be significantly increased. Additionally, at this time, said subject will experience an enhanced antibody and T-cell mediated immune response against NS3, as evidenced by an increased fraction of NS3 specific antibodies as detected by EIA, and a reduction in viral load as detected by RT-PCR.

Embodiments also include NS3/4A fusion proteins or nucleic acids encoding these molecules. For instance, production and purification of recombinant protein may be facilitated by the addition of auxiliary amino acids to form a "tag". Such tags include, but are not limited to, His-6, Flag, Myc and GST. The tags may be added to the C-terminus, N-terminus, or within the NS3/4A amino acid sequence. Further embodiments include NS3/4A fusion proteins with amino or carboxy terminal truncations, or internal deletions, or with additional polypeptide sequences added to the amino or carboxy terminal ends, or added internally. Other embodiments include NS3/4A fusion proteins, or truncated or mutated versions thereof, where the residues of the NS3/4A proteolytic cleavage site have been substituted. Such substitutions include, but are not limited to, sequences where the P1' site is a Ser, Gly, or Pro, or the P1 position is an Arg, or where the P8 to P4' sequence is Ser-Ala-Asp-Leu-Glu-Val-Val-Thr-Ser-Thr-Trp-Val (SEQ. ID. NO.: 28).

Other embodiments concern an immunogen comprising the NS3/4A fusion protein, or a truncated or modified version thereof, capable of eliciting an enhanced immune response against NS3. The immunogen can be provided in a substantially purified form, which means that the immunogen has been rendered substantially free of other proteins, lipids, carbohydrates or other compounds with which it naturally associates. Embodiments also include vaccine compositions comprising the NS3/4A fusion protein (SEQ. ID. NO.: 17), or a truncated or mutated version thereof (e.g., SEQ. ID. NOS.: 29-32 and 43-49) or a fragment thereof (e.g., SEQ. ID. NOs.: 25-27, and 33-42), and an adjuvant, such as ribavirin. The following example describes one approach to prepare a vaccine composition comprising the NS3/4A fusion protein and an adjuvant.

EXAMPLE 15

To generate a tagged NS3/4A construct, the NS3/4A coding sequence of NS3/4A-pVAX is removed by digestion with EcoRI and XbaI, and the isolated fragment is inserted into an Xpress vector (Invitrogen). The Xpress vector allows for the production of a recombinant fusion protein having a short N-terminal leader peptide that has a high affinity for divalent cations. Using a nickel-chelating resin (Invitrogen), the recombinant protein can be purified in one step and the leader can be subsequently removed by cleavage with enterokinase. A preferred vector is the pBlueBacHis2 Xpress. The pBlueBacHis2 Xpress vector is a Baculovirus expression vector containing a multiple cloning site, an ampicillin resistance gene, and a lac z gene. Accordingly, the digested amplification fragment is cloned into the pBlueBacHis2 Xpress vector and SF9 cells are infected. The expression protein is then isolated or purified according to the maufacturer's instructions. An NS3/4A containing vaccine composition is then made by mixing 100 μg of the rNS3/4A with 1 mg of ribavirin.

Said vaccine composition can be used to raise antibodies in a mammal (e.g., mice or rabbits) or can be injected intramuscularly into a human so as to to raise antibodies, preferably a human that is chronically infected with the HCV virus. The recipient preferably receives three immunization boosts of the mixture at 4-week intervals. By the third boost, the titer of antibody specific for HCV will be significantly increased. Additionally, at this time, said subject will experience an enhanced antibody and T-cell mediated immune response against NS3, as evidenced by an increased fraction of NS3 specific antibodies as detected by EIA, and a reduction in viral load as detected by RT-PCR. The section below provides more explanation concerning the methods of using the compositions described herein.

Methods of Using Compositions Comprising Ribavirin and an Antigen

Routes of administration of the vaccines described herein include, but are not limited to, transdermal, parenteral, gastrointestinal, transbronchial, and transalveolar. Transdermal administration can be accomplished by application of a cream, rinse, gel, or other compounds capable of allowing ribavirin and antigen to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having ribavirin and an antigen that are suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein expressly incorporated by reference in its entirety.

Compositions having ribavirin and an antigen that are suitable for parenteral administration include, but are not limited to, pharmaceutically acceptable sterile isotonic solutions. Such solutions include, but are not limited to, saline, phosphate buffered saline and oil preparations for injection into a central venous line, intravenous, intramuscular, intraperitoneal, intradermal, or subcutaneous injection.

Compositions having ribavirin and an antigen that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver vaccines having ribavirin and an antigen.

Compositions having ribavirin and an antigen that are suitable for gastrointestinal administration include, but not limited to, pharmaceutically acceptable powders, pills or liquids for ingestion and suppositories for rectal administration.

The gene constructs described herein, in particular, may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise nonimmunogenic cells that have gene constructs incorporated therein can be implanted into the individual even if the vaccinated cells were originally taken from another individual.

According to some embodiments, the gene construct is administered to an individual using a needleless injection device. According to some embodiments, the gene construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

The vaccines containing ribavirin and an antigen can be used to treat and prevent a vast spectrum of diseases and can enhance the immune response of an animal to an antigen. As one of skill in the art will appreciate, conventional vaccines have been administered to subjects in need of treatment or prevention of bacterial diseases, viral diseases, fungal diseases, and cancer. Because the vaccines described herein include conventional vaccines, which have been modified by the addition of ribavirin, the methods described herein include the treatment and prevention of a disease using a vaccine that comprises an antigen and ribavirin.

Preferred embodiments concern methods of treating or preventing hepatitis infection. In these embodiments, an animal in need is provided a hepatitis antigen (e.g., a peptide antigen or nucleic acid-based antigen) and an amount of ribavirin sufficient to exhibit an adjuvant activity in said animal. Accordingly, an animal can be identified as one in need by using currently available diagnostic testing or clinical evaluation. The range of hepatitis viral antigens that can be used with these embodiments is diverse. Preferred hepatitis viral antigens include an HBV antigen, an HAV antigen, an HCV antigen, nucleic acids encoding these antigens, or any combination thereof. Highly preferred embodiments include an HBV antigen selected from the group consisting of hepatitis B surface antigen (HBsAg), hepatitis core antigen (HBcAg), and hepatitis E antigen (HBeAg), in particular, the peptide and nucleic acid-based antigens described supra. The ribavirin and antigen can be provided separately or in combination, and other adjuvants (e.g., oil, alum, or other agents that enhance an immune response) can also be provided to the animal in need. Thus, preferred embodiments include methods of treating or preventing hepatitis in an animal (e.g., HBV) by identifying an infected animal or an animal at risk of infection and providing said animal a hepatitis antigen (e.g., HBsAg, HBcAg, and HBeAg) and an amount of ribavirin sufficient to exhibit adjuvant activity.

Other embodiments include methods of enhancing an immune response to an antigen by providing an animal in need with an amount of ribavirin that is effective to enhance said immune response. In these embodiments, an animal in need of an enhanced immune response to an antigen is identified by using currently available diagnostic testing or clinical evaluation. Oftentimes these individuals will be suffering from a disease (e.g., bacterial, fungal, mold, viral, or cancer) or are at risk from contracting the disease. However, an animal in need of an enhanced immune response can be an animal that has been poisoned (e.g., bit by a poisonous insect or animal) or that has been exposed to a toxin or other toxic compound. Once identified, these animals are provided an appropriate antigen and an amount of ribavirin effective to enhance an immune response in the animal.

As above, the hepatitis viral antigens that can be used with these embodiments include, but are not limited to, an HBV antigen, an HAV antigen, an HCV antigen, a nucleic acid encoding these molecules, or any combination thereof. Highly preferred embodiments include an HBV antigen selected from the group consisting of hepatitis B surface antigen (HBsAg), hepatitis core antigen (HBcAg), and hepatitis E antigen (HBeAg), in particular, the peptide and nucleic acid-based antigens described supra. The ribavirin and antigen can be provided separately or in combination, and other adjuvants (e.g., oil, alum, or other agents that enhance an immune response) can also be provided to the animal in need. Thus, preferred embodiments include methods of enhancing an immune response to a hepatitis antigen (e.g., HBV) by identifying an animal in need and providing the animal a hepatitis antigen (e.g., HBsAg, HBcAg, and HBeAg) and an amount of ribavirin that is effective to enhance an immune response in the animal.

By one approach, for example, an uninfected individual is provided with the above mentioned vaccine compositions in an amount sufficient to elicit a cellular and humoral immune response to NS3 so as to protect said individual from becoming infected with HCV. In another embodiment, an HCV-infected individual is identified and provided with a vaccine composition comprising ribavirin and NS3 in an amount sufficient to enhance the cellular and humoral immune response against NS3 so as to reduce or eliminate the HCV infection. Such individual may be in the chronic or acute phase of the infection. In yet another embodiment, an HCV-infected individual suffering from HCC is provided with a composition comprising ribavirin and the NS3/4A fusion gene in an amount sufficient to elicit a cellular and humoral immune response against NS3-expressing tumor cells.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of enhancing the production of hepatitis-specific antibodies in a subject in need thereof consisting essentially of:
    identifying a subject in need of an enhancement of the production of hepatitis-specific antibodies; and
    providing, in a single administration, an immunogenic composition that comprises an effective amount of ribavirin and a nucleic acid molecule that encodes a hepatitis antigen to said subject.

2. The method of claim 1, wherein said hepatitis antigen is a hepatitis C virus (HCV) antigen.

3. The method of claim 1, wherein said nucleic acid molecule encodes a hepatitis antigen that comprises a hepatitis C virus NS3 protein.

4. The method of claim 1, wherein said immunogenic composition is formulated for use with an injection device.

5. The method of claim 4, wherein said injection device is an electrical injection device.

6. The method of claim 4, wherein said injection device is a needleless injection device.

7. The method of claim 1, further comprising measuring IgG levels following administration of said immunogenic composition.

8. The method of claim 2, wherein said immunogenic composition is formulated for use with an injection device.

9. The method of claim 8, wherein said injection device is an electrical injection device.

10. The method of claim 8, wherein said injection device is a needleless injection device.

11. The method of claim 2, further comprising measuring IgG levels following administration of said immunogenic composition.

12. The method of claim 3, wherein said immunogenic composition is formulated for use with an injection device.

13. The method of claim 12, wherein said injection device is an electrical injection device.

14. The method of claim 12, wherein said injection device is a needleless injection device.

15. The method of claim 3, further comprising measuring IgG levels following administration of said immunogenic composition.

16. The method of claim 1, wherein said immunogenic composition is provided to said subject intranasally.

17. The method of claim 1, wherein said immunogenic composition is provided to said subject transdermally.

18. The method of claim 1, wherein said immunogenic composition comprises an oil.

* * * * *

UNITED STATES PATENT AND TRADEMARK OFFICE
CERTIFICATE OF CORRECTION

PATENT NO.        : 7,244,715 B2
APPLICATION NO.   : 11/411493
DATED             : July 17, 2006
INVENTOR(S)       : Sallberg et al.

It is certified that error appears in the above-identified patent and that said Letters Patent is hereby corrected as shown below:

Title page 2, in column 1, under Foreign Patent Documents, line 36, delete "2001" and insert -- 2002 --, therefor.

Title page 2, in column 1, under Other Publications, line 1, delete "Pathogogen," and insert -- Pathogen, --, therefor.

In Column 2, line 24, after "4,950,647)" delete "," and insert -- . --, therefor.

In Column 8, line 65, delete "does" and insert -- doses --, therefor.

In Column 22, line 33, delete "1,8" and insert -- 1.8 --, therefor.

In Column 39, line 7, delete "W138." and insert -- WI38. --, therefor.

In Column 45, line 44, delete "calorimetrically," and insert -- colorimetrically, --, therefor.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,244,715 B2
APPLICATION NO. : 11/411493
DATED : July 17, 2006
INVENTOR(S) : Sallberg et al.

It is certified that error appears in the above-identified patent and that said Letters Patent is hereby corrected as shown below:

Title page 2, in column 1, under Foreign Patent Documents, line 36, delete "2001" and insert -- 2002 --, therefor.

Title page 2, in column 1, under Other Publications, line 1, delete "Pathogogen," and insert -- Pathogen, --, therefor.

In Column 2, line 24, after "4,950,647)" delete "," and insert -- . --, therefor.

In Column 8, line 65, delete "does" and insert -- doses --, therefor.

In Column 22, line 33, delete "1,8" and insert -- 1.8 --, therefor.

In Column 39, line 7, delete "W138." and insert -- WI38. --, therefor.

In Column 45, line 44, delete "calorimetrically," and insert -- colorimetrically, --, therefor.

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,244,715 B2
APPLICATION NO. : 11/411493
DATED : July 17, 2007
INVENTOR(S) : Sallberg et al.

It is certified that error appears in the above-identified patent and that said Letters Patent is hereby corrected as shown below:

Title page 2, in column 1, under Foreign Patent Documents, line 36, delete "2001" and insert -- 2002 --, therefor.

Title page 2, in column 1, under Other Publications, line 1, delete "Pathogogen," and insert -- Pathogen, --, therefor.

In Column 2, line 24, after "4,950,647)" delete "," and insert -- . --, therefor.

In Column 8, line 65, delete "does" and insert -- doses --, therefor.

In Column 22, line 33, delete "1,8" and insert -- 1.8 --, therefor.

In Column 39, line 7, delete "W138." and insert -- WI38. --, therefor.

In Column 45, line 44, delete "calorimetrically," and insert -- colorimetrically, --, therefor.

This certificate supersedes the Certificate of Correction issued December 11, 2007.

Signed and Sealed this

First Day of January, 2008

JON W. DUDAS
*Director of the United States Patent and Trademark Office*

UNITED STATES PATENT AND TRADEMARK OFFICE
CERTIFICATE OF CORRECTION

PATENT NO.          : 7,244,715 B2
APPLICATION NO.     : 11/411493
DATED               : July 17, 2007
INVENTOR(S)         : Sallberg et al.

It is certified that error appears in the above-identified patent and that said Letters Patent is hereby corrected as shown below:

Title page 2, in column 1, under Foreign Patent Documents, line 36, delete "2001" and insert -- 2002 --, therefor.

Title page 2, in column 1, under Other Publications, line 1, delete "Pathogogen," and insert -- Pathogen, --, therefor.

In Column 2, line 24, after "4,950,647)" delete "," and insert -- . --, therefor.

In Column 8, line 65, delete "does" and insert -- doses --, therefor.

In Column 22, line 33, delete "1,8" and insert -- 1.8 --, therefor.

In Column 39, line 7, delete "W138." and insert -- WI38. --, therefor.

In Column 45, line 44, delete "calorimetrically," and insert -- colorimetrically, --, therefor.

This certificate supersedes all previously issued Certificates of Correction.

Signed and Sealed this

Twenty-ninth Day of January, 2008

JON W. DUDAS
*Director of the United States Patent and Trademark Office*